US012594277B2

(12) United States Patent
Cosford et al.

(10) Patent No.: US 12,594,277 B2
(45) Date of Patent: Apr. 7, 2026

(54) MACROCYCLIC ULK1/2 INHIBITORS

(71) Applicants: SALK INSTITUTE FOR BIOLOGICAL STUDIES, La Jolla, CA (US); SANFORD BURNHAM PREBYS MEDICAL DISCOVERY INSTITUTE, La Jolla, CA (US)

(72) Inventors: Nicholas D. P. Cosford, La Jolla, CA (US); Nicole A. Bakas, La Jolla, CA (US); Reuben J. Shaw, La Jolla, CA (US); Allison S. Limpert, La Jolla, CA (US); Sonja N. Brun, La Jolla, CA (US)

(73) Assignees: SALK INSTITUTE FOR BIOLOGICAL STUDIES, La Jolla, CA (US); SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 581 days.

(21) Appl. No.: 17/799,634

(22) PCT Filed: Feb. 12, 2021

(86) PCT No.: PCT/US2021/018038
§ 371 (c)(1),
(2) Date: Aug. 12, 2022

(87) PCT Pub. No.: WO2021/163627
PCT Pub. Date: Aug. 19, 2021

(65) Prior Publication Data

US 2023/0099804 A1 Mar. 30, 2023

Related U.S. Application Data

(60) Provisional application No. 62/977,039, filed on Feb. 14, 2020.

(51) Int. Cl.
*A61K 31/529* (2006.01)
*A61K 31/282* (2006.01)
*A61K 45/06* (2006.01)
*C07D 498/08* (2006.01)

(52) U.S. Cl.
CPC .......... *A61K 31/529* (2013.01); *A61K 31/282* (2013.01); *A61K 45/06* (2013.01); *C07D 498/08* (2013.01)

(58) Field of Classification Search
CPC .... A61K 31/529; A61K 31/282; A61K 45/06; C07D 498/08; A61P 35/00
See application file for complete search history.

(56) References Cited

U.S. PATENT DOCUMENTS 4,652,441 A 3/1987 Okada et al.
4,675,189 A 6/1987 Kent et al.
4,677,191 A 6/1987 Tanaka et al.
4,728,721 A 3/1988 Yamamoto et al.
4,917,893 A 4/1990 Okada et al.
2005/0256111 A1 11/2005 Kath
2006/0069110 A1 3/2006 Anderson et al.
2010/0081679 A1 4/2010 Greul et al.
2010/0249092 A1 9/2010 Singh et al.
2012/0196870 A1 8/2012 Arbiser
2013/0040310 A1 2/2013 Shaw et al.
2013/0252950 A1 9/2013 Blenis et al.
2017/0038387 A1 2/2017 Gandhi et al.
2017/0114073 A1 4/2017 Alexander et al.
2017/0342088 A1 11/2017 Shaw et al.
2023/0130766 A1 4/2023 Shaw et al.
2023/0135635 A1 5/2023 Shaw et al.
2023/0332243 A1 10/2023 Shaw et al.

FOREIGN PATENT DOCUMENTS

CA 3139120 11/2020
CA 3139708 11/2020
CA 3143489 12/2020
CN 103059030 4/2013
CN 105524045 4/2016
CN 105 801 603 A 7/2016
CN 106188029 12/2016
EP 3159338 4/2017
JP 6684700 8/2014
WO WO 03/078404 9/2003
WO WO 2004/056789 7/2004
WO WO 2004/074244 9/2004
WO WO 2004/080980 9/2004
WO WO 2005/009443 2/2005
WO WO 2005/049021 6/2005
WO WO-2006061415 A1 * 6/2006 ................ A61P 3/10
WO WO 2006/124874 11/2006

(Continued)

OTHER PUBLICATIONS

International Search Report and Written Opinion issued in corresponding PCT Application No. PCT/US2021/018038, mailed May 18, 2021.
PubChem, SID 375982596; BDBM50210177. <URL: https://pubchem.ncbi.nlm.nih.gov/substance/375982596>.
Egan Daniel F et al: "Small Molecule 1-15 Inhibition of the Autophagy Kinase ULK1 and Identification of ULK1 Substrates", Molecular Cell, vol. 59, No. 2, Jul. 16, 2015 (Jul. 16, 2015), pp. 285-297, xXP002776079, ISSN: 1097-4164, DOI: 10.1016/J.MOLCEL.2015.05.031.
EP Extended Supplementary Search Report and Opinion, Jan. 15, 2024, 10 pages.
Achary et al., "Discover of Novel Tetrahyroisoquinoline-Containing Pyrimidines as ALK Inhibitors", Bioorganic & Medicinal Chemistry, Elsevier, Amsterdam, NL, vol. 24, No. 2, Dec. 7, 2015, pp. 207-219.

(Continued)

*Primary Examiner* — Jeffrey S Lundgren
*Assistant Examiner* — W. Justin Youngblood
(74) *Attorney, Agent, or Firm* — NORTON ROSE FULBRIGHT US LLP

(57) ABSTRACT

The present disclosure is directed to compounds, compositions, formulations and methods of use thereof in the treatment and prevention of ULK mediated diseases, including cancer.

8 Claims, No Drawings

(56) References Cited

FOREIGN PATENT DOCUMENTS

| | | | |
|---|---|---|---|
| WO | WO 2006/129100 | 12/2006 | |
| WO | WO 2007/028445 | 3/2007 | |
| WO | WO 2008/049123 | 4/2008 | |
| WO | WO 2008/125839 | 10/2008 | |
| WO | WO-2008140421 A2 * | 11/2008 | ............. A61P 35/00 |
| WO | WO 2009/071535 | 6/2009 | |
| WO | WO 2009/083185 | 7/2009 | |
| WO | WO 2009/132202 | 10/2009 | |
| WO | WO 2009/145856 | 12/2009 | |
| WO | WO 2009/158431 | 12/2009 | |
| WO | WO 2010/002846 A1 | 1/2010 | |
| WO | WO 2010/129622 | 11/2010 | |
| WO | WO 2010/146132 | 12/2010 | |
| WO | WO 2011/084108 | 7/2011 | |
| WO | WO 2011/133668 | 10/2011 | |
| WO | WO 2012/006635 | 1/2012 | |
| WO | WO 2012/045195 | 4/2012 | |
| WO | WO 2012/119095 | 9/2012 | |
| WO | WO 2012/120048 | 9/2012 | |
| WO | WO 2013/072392 | 5/2013 | |
| WO | WO 2013/126132 | 8/2013 | |
| WO | WO 2013/173506 | 11/2013 | |
| WO | WO 2014/062621 | 4/2014 | |
| WO | WO 2014/071109 | 5/2014 | |
| WO | WO 2014/098932 | 6/2014 | |
| WO | WO 2014/116973 | 7/2014 | |
| WO | WO 2014/197680 | 12/2014 | |
| WO | WO 2015/158310 | 10/2015 | |
| WO | WO 2016/033100 | 3/2016 | |
| WO | WO 2016/049201 | 3/2016 | |
| WO | WO 2016/090079 | 6/2016 | |
| WO | WO 2016/196393 | 12/2016 | |
| WO | WO 2018/075608 | 4/2018 | |
| WO | WO 2018/102366 | 6/2018 | |
| WO | WO 2018/203691 | 11/2018 | |
| WO | WO 2021/216440 A1 | 10/2021 | |

OTHER PUBLICATIONS

Anonymous: "A549",Dec. 31, 2021 (Dec. 31, 2021), XP093122400, Retrieved from the Internet: URL: https://depmap.org/portal/cell_line/A549_LUNG?tab=overview[retrieved on Jan. 22, 2024].

Anonymous: "H460", 1-15 Oct. 5, 2023 (Oct. 5, 2023), XP093122556, Retrieved from the Internet: URL: https: //www.cellosaurus.org/CVCL_0459 [retrieved on Jan. 23, 2024].

Averous et al. "Regulation of cyclin D1 expression by Mtorc1 signaling requires eukaryotic initiation factor 4e-binding protein 1," Oncogene, vol. 27, pp. 1106-1113, 2008.

Babak et al. "mTOR inhibition in glioblastoma: requiem for a dream?", Neuro-Oncology, vol. 20(5), pp. 584-585, Mar. 28, 2018.

Bactrim Spec Sheet, AR Scientific, 2010.

Battelli et al. "mTOR inhibitors in renal cell carcinoma," Therapy, Jul. 2011, 8(4):359-367.

Bellare et al., "Targeting autophagy reverses de novo resistance in homologous recombination repair proficient breast cancers to PARP inhibition," Br J Cancer. Jan. 21, 2021.

Berge et al., "Pharmaceutical Salts," Journal of Pharmaceutical Sciences 66(1):1-19 (Jan. 1977).

Brun et al., "The autophagy initiating kinase ULK1 is required for pancreatic cancer cell growth and survival," bioRxiv, pp. 1-26, May 23, 2021.

Cambridge MedChem [online], "Bioisosteric Replacements," 2013, <https://www.cambridgemedchemconsulting.com/resources/bioisoteres/>, retrieved on Feb. 10, 2024, 5 pages.

Chan et al., "MTORC1 phosphorylates the ULK1-mAtg13-FIP2OO autophagy regulatory complex," Science Signaling 2(84):pe51 (2009).

Chen et al., "mTORC1 inhibitor RAD001 (everolimus) enhances non-small cell lung cancer cell radiosensitivity in vitro via suppressing epithelial-mesenchymal transition", Acta Pharmacologica Sinica, vol. 40, pp. 1085-1094, 2019.

Choi et al., "Design and synthesis of 7H-pyrrolo[2,3-d]pyrimidines as focal adhesion kinase inhibitors. Part 1", *Bioorganic & Medicinal Chemistry Letters*, vol. 16, No. 8; pp. 2173-2176, 2006.

Choueiri et al. "The Role of mTOR Inhibitors and P13K Pathway Blockade in Rcc", Kidney Cancer, pp. 209-223, 2011.

Din et al. "Aspirin Inhibits mTOR Signaling, Activates AMP-Activated Protein Kinase, and Induces Autophagy in Colorectal Cancer Cells," Gastroenterology, vol. 142, No. 7, pp. 1504-1515, Jun. 2012.

Egan et al., "Phosphorylation of ULK1 (hATG1) by AMP-activated protein kinase connects energy sensing to mitophagy," Science, 2011, 331 :456-461.

Egan et al., "The autophagy initiating kinase ULK1 is regulated via opposing phosphorylation by AMPK and mTOR," Autophagy, 2011, 7:643-644.

Egan, "Identification and Characterization of the Autophagy Initiating Kinase ULK1 as a substrate of AMP-Activation Protein Kinase (AMPK)," UC San Diego Electronic Theses and Dissertations, 2014.

Elkabets et al. "mTORC1 Inhibition is required for sensitivity to P13K p110a inhibitors in PIK3CA-Mutant breast cancer," Science Translation Medicine, vol. 5, Issue 196, pp. 196-199, Jul. 31, 2013.

Fabian et al., "A small molecule-kinase interaction map for clinical kinase inhibitors," Nature Biotechnology, 23(3): 329-336 (2005).

Fichert et al., "A new strategy for the preparation of secondary amines via o-(tetrahydropyranyloxymethyl)-benzamides," Tetrahedron Letters 39:5017-5018 (1998).

Fiedler et al., "Identification of dual Mtorc1 and Mtorc2 inhibitors in melanoma cells: Prodigiosin vs. obatoclax", Biochemical Pharmacology, vol. 83, Issue 4, pp. 489-496, 2012.

Gammoh et al. "Role of autophagy in histone deacetylase inhibitor-induced apoptotic and nonapoptotic cell death," PNAS, vol. 109 No. 17, pp. 6561-6565, Apr. 24, 2012.

Ghadimi et al. "Targeting the P13K/mTOR Axis, Alone and in Combination with Autophagy Blockade, for the Treatment of Malignant Peripheral Nerve Sheath Tumors," Mol Cancer Ther, 2012, vol. 11 No. 8, pp. 1758-1769.

Gill et al., "Current Status of mTOR Inhibitors as Novel Therapeutic Agents", Journal of Global Pharma Technology, 2017; 06(9): 14-34.

Green et al., "To be or not to be? How selective autophagy and cell death govern cell fate," Cell, 157:65-75 (2014).

Guo et al., "Activated Ras requires autophagy to maintain oxidative metabolism and tumorigenesis," Genes Dev. 25:460-470 (2011).

Guo et al., "Autophagy-mediated tumor promotion," Cell 155:1216-1219 (2013).

Gwinn et al., "AMPK Phosphorylation of Raptor Mediates a Metabolic Checkpoint," Molecular Cell 30(2):214-226 (2008).

Hara et al., "FIP2OO, a ULK-interacting protein, is required for autophagosome formation in mammalian cells," J Cell Biol 181 (3):497-510 (2008).

Hare et al. "mTOR function and therapeutic targeting in breast cancer," Am J. Cancer Res. vol. 7(3), pp. 383-404, Mar. 15, 2017.

Hasumi et al. "Homozygous loss of BHD causes early embryonic lethality and kidney tumor development with activation of Mtorc1 and Mtorc2," PNAS, vol. 106. No. 44, pp. 18722-18727, 2009.

He et al., "In vitro study of FUZ as a novel potential therapeutic target in non-small-cell lung cancer," Life Sciences, Feb. 6, 2018, vol. 197, pp. 91-100.

Heng et al., "Research progress on the anti-tumor effect of mTOR inhibitors mediated by autophagy," China Pharmacy, 27, Oct. 3, 2012, 6 Pages (with Machine translation).

Hornbeck et al., "PhosphoSite: A bioinformatics resource dedicated to physiological protein phosphorylation," Proteomics 4(6):1551-1561 (2004).

Hosokawa et al., "Atg1O1, a novel mammalian autophagy protein interacting with Atg13," Autophagy 5:973-979 (2009).

Huang et al., "Identification of melanoma biomarkers based on network modules by integrating the human signaling network with microarrays," Journal of Cancer Research and Therapeutics, vol. 10, Special Issue 2, 2014, 15 pages.

Huang et al., "Inhibition of mTOR Kinase by AZD8055 Can Antagonize Chemotherapy-induced Cell Death through Autophagy

(56) References Cited

OTHER PUBLICATIONS

Induction and Down-regulation of p62/Sequestosome1*," JBC vol. 286, No. 46, pp. 40002-40012. (Year: 2011).
Hutti et al., "A rapid method for determining protein kinase phosphorylation specificity," Nature Methods 1, 27-29 (2004).
Iksen et al. "Targeting the PI3K/AKT/mTOR Signaling Pathway in Lung Cancer: An Update Regarding Potential Drugs and Natural Products," Molecules 2021, 26, 4100 pp. 1-27.
Jaber et al., "Class III PI3K Vps34 plays an essential role in autophagy and in heart and liver function," PNAS USA 109:2003-2008 (2012).
Jin et al., "Blockage of Stat3 enhances the sensitivity of NSCLC cells to PI3K/mTOR inhibition," Biochemical and Biophysical Research Communications, vol. 444, Issue 4, Feb. 21, 2014, pp. 502-508.
Jones et al. "Therapeutic Targeting of Autophagy for Renal Cell Carcinoma Therapy," Cancers, vol. 12, pp. 1-16, 2020.
Jung et al., "ULK-Atg13-FIP2OO Complexes Mediate mTOR Signaling to the Autophagy Machinery," Mol Biol Cell 20(7):1992-2003 (2009).
Kang et al. "Autophagy in pancreatic cancer pathogenesis and treatment," Am J Cancer Res, vol. 2, No. 4, pp. 383-396, 2012.
Kang et al., "mTORC1 phosphorylation sites encode their sensitivity to starvation and rapamycin," Science 341 : 1236566 (2013).
Karaman et al., "A quantitative analysis of kinase inhibitor selectivity," Nat. Biotechnol. 26:127-132 (2008).
Kim et al. "Targeting the AMP-activated protein kinase for cancer prevention and therapy," Frontiers in Oncology, vol. 3, Article 175, pp. 1-12, 2013.
Kim et al., "AMPK and mTOR regulate autophagy through direct phosphorylation of Ulk1," Nat. Cell Biol. 13:132-141 (2011).
Kim et al., "Differential regulation of distinct Vps34 complexes by AMPK in nutrient stress and autophagy," Cell 152:290-303 (2013).
Kinoshita et al., "Phosphate-binding tag, a new tool to visualize phosphorylated proteins," Mol. Cell. Proteomics 5:749-757 (2006).
Kumar et al., "A Review: Status of Genetic Modulated Non-Small Cell Lung Cancer Targets and Treatment (Current Updates in Drugs for Non-Small Cell Lung Center Treatment)," Asian Journal of Pharmaceutical and Clinical Research, vol. 11, No. 8, Aug. 7, 2018, pp. 40-55.
Lazarus et al., "Discovery and structure of a new inhibitor scaffold of the autophagy initiating kinase ULK1," Bioorg Med Chem 23(17): 5483-5488 (2015).
Lazarus et al., "Structure of the Human Autophagy Initiating Kinase ULK1 in Complex with Potent Inhibitors", ACS Chemical Biology, vol. 10, No. 1, Jan. 6, 2015, pp. 257-261.
Le et al., "Design and synthesis of a novel pyrrolidinyl pyrido pyrimidinone derivative as a potent inhibitor of PIKα and mTOR," Bioorganic & Medicinal Chemistry Letters 2012, vol. 22, pp. 5098-5103.
Lee et al. "The nuclear receptor TR3 regulated Mtorc1 signaling in lung cancer cells expressing wild-type p53," Oncogene, vol. 31, pp. 3265-3276, 2012.
Lee et al., "Triple negative breast cancer: Emerging therapeutic modalities and novel combination therapies," Cancer Treatment Reviews 62 (2018) 110-122.
Lin et al. "Benzyl isothiocyanate induces protective autophagy in human prostate cancer cells via inhibition of mTOR signaling", Carcinogenesis, vol. 34, No. 2, pp. 406-414, 2013.
Lin et al. "Inhibition of CAMKK2 impairs autophagy and castration-resistant prostate cancer via suppression of AMPK-ULK1 signaling," bioRxiv, pp. 1-51, Jun. 3, 2020.
Liu et al., "The AMPK inhibitor Compound C is a potent AMPK-independent anti-glioma agent," National Library of Medicine, Mol Cancer Ther, Mar. 2014, 13(3): 596-605.
Lotze et al. "Inhibiting Autophagy A Novel Approach for the Treatment of Renal Cell Carcinoma", The Cancer Journal, vol. 19, No. 4, pp. 341-347, 2013.
Lu et al. "Overexpression of ULK1 Represents a Potential Diagnostic Marker for Clear Cell Renal Carcinoma and the Antitumor Effects of SB1-0206965", EBioMedicine, vol. 34, pp. 85-93, 2018.
Lu et al., "Design of novel focal adhesion kinase inhibitors using 3D-QSAR and molecular docking," Med Chem Res, Sep. 28, 2013, 23(4):1976-1997.
MedChem Express [online], "mTOR Signaling Pathway," 2024, retrieved on Feb. 10, 2024, <https://www.medchemexpress.com/Targets/mTOR/mtor-signaling-pathway.html>, 3 pages.
Melnik et al. "The impact of cow's milk-mediated Mtorc1-signaling in the initiation and progression of prostate cancer," Nutrition & Metabolism, vol. 9, No. 74, pp. 1-24, 2012.
Mercer et al., "A novel, human Atg13 binding protein, Atg1O1, interacts with ULK1 and is essential for macroautophragy," Autophagy 5:649-662 (2009).
Michel et al. The effect of site of administration in the gastrointestinal tract on the absorption of insulin from nanocapsules in diabetic rats. J Pharm Pharmacol 43:1-5 (1991).
Miller et al., "Synthesis and Phenotypic Screening of Guanine-Mimetic Library", *ChemBioChem*, vol. 5, No. 7; pp. 1010-1012, 2004.
Molhoek et al., "Synergistic inhibition of human melanoma proliferation by combination treatment with B-Raf inhibitor BAY43-9OO6 and mTOR inhibitor Rapamycin," J Trans Med 3:39 (2005).
Obenauer et al., "Scansite 2.0: Proteome-wide prediction of cell signaling interactions using short sequence motifs," Nucleic Acids Res. 31:3635-3641 (2003).
Papinski et al., "Early steps in autophagy depend on direct phosphorylation of Atg9 by the Atg1 kinase," Mol. Cell 53:471-483 (2014).
Pubchem, SID 146791551, Modify date: Jun. 2, 2019 [retrieved on Mar. 19, 2021 from the Internet: URL: https://pubchem .ncbi .nlm .nih.gov/substance/146791551.
Pubchem, SID 328097028, Available date: Jan. 31, 2017 [retrieved on Mar. 19, 2021 from the Internet: URL: https://pubchem.ncbi.nlm.nih.gov/substance/328097028.
Pubchem, SID 354161717, Available date: Jan. 29, 2018 [retrieved on Mar. 19, 2021 from the Internet: URL:https://pubchem .ncbi .nlm .nih.gov/substance/354161717.
Pubchem, SID 354167691, Available date: Jan. 29, 2018 [retrieved on Mar. 19, 2021 from the Internet: URL: https://pubchem .ncbi .nlm.nih.gov/substance/354167691.
Pubchem, SID 384264815, Available date: May 24, 2019 [retrieved on May 20, 2021 from the Internet: URL: https://pubchem.ncbi.nlm.nih.gov/substance/384264815.
Qi et al., "Synthesis and biological evaluation of novel pazopanib derivatives as antitumor agents," Bioorganic & Medicinal Chemistry Letters, 2014, vol. 24, pp. 1108-1110.
Rajesh et al., "Binding to syntenin-1 protein defines a new mode of ubiquitin-based interactions regulated by phosphorylation," J Biol Chem 286:39606-39614 (2011).
Rao et al., "A dual role for autophagy in a murine model of lung cancer," Nat Commun 5, 3056 (2014).
Ren et al., "Design, Synthesis and Characterization of an Orally Active Dual-Specific ULK1/2 Autophagy Inhibitor that Synergizes with the PARP Inhibitor Olaparib for the Treatment of Triple-Negative Breast Cancer," J. Med. Chem. 53:14609-14625 (2020).
Rosenfeldt et al., "p53 status determines the role of autophagy in pancreatic tumour development," Nature. Dec. 12, 2013; 504(7479):296-300.
Rothschild et al. "Autophagy protects against Src tyrosine kinase inhibitor treatment in non-small cell lung cancer cells via a novel miR-106a/ULK1 pathway," Cancer Res (2012) 72 (8_Supplement): 2263.
Rothschild et al., "Src tyrosine kinase inhibitors activate protective, ULK1-dependent autophagy by downregulating oncomir-106-393-cluster expression in non-small cell lung cancer cells," Clin Cancer Res (2012) 18 (3_Supplement): B30.
Roudsari et al., "Inhibitors of the PI3K/Akt/mTOR Pathway in Prostate Cancer Chemoprevention and Intervention," Pharmaceutics, vol. 13, pp. 1-34, 2021.

(56) References Cited

OTHER PUBLICATIONS

Russell et al., "ULK1 induces autophagy by phosphorylating Beclin-1 and activating VPS34 lipid kinase," Nat. Cell Biol. 15:741-750 (2013).
Sanitago-O'Farrill et al., "Poly(adenosine diphosphate ribose) polymerase inhibitors induce autophagy-mediated drug resistance in ovarian cancer cells, xenografts, and patient-derived xenograft models," Cancer. Feb. 15, 2020;126(4):894-907.
Sarkaria et al., "Combination of Temsirolimus (CCI-779) with Chemoradiation in Newly Diagnosed Glioblastoma Multiforme (GBM) (NCCTG trial N027D) Is Associated with Increased Infectious Risks," Clinical Cancer Res. 2010, 16(22), 5573-5580.
Singh et al., "Genomic profiling in pancreatic ductal adenocarcinoma and a pathway towards therapy individualization: A scoping review," Cancer Treatment Revies, vol. 75, Mar. 22, 2019, pp. 27-38.
Smith et al., "Metformin inhibition of Mtorc1 Activation DNA synthesis and proliferation in pancreatic cancer cells: dependence on glucose concentration and role of AMPK," Biochem Biophys Res Commun., vol. 430, Issue. 1, pp. 352-357, 2013.
STN Registry [online], CAS Registration No. 1283101-41-6.
STN Registry [online], CAS Registration No. 1283489-57-5.
STN Registry [online], CAS Registration No. 1285619-55-7.
STN Registry [online], CAS Registration No. 1348559-94-4.
STN Registry [online], CAS Registration No. 1349400-82-3.
STN Registry [online], CAS Registration No. 1445726-43-1.
STN Registry [online], CAS Registration No. 794466-21-0.
STN Registry [online], CAS Registration No. 794466-22-1.
Tang et al. "Low expression of ULK1 is associated with operable breast cancer progression and is adverse prognostic marker of survival for patients," Breast Cancer Research and Treatment, vol. 134, pp. 549-560, 2012.
Tang et al., "SBI0206965, a novel inhibitor of Ulk1, suppresses non-small cell lung cancer cell growth by modulating both autophagy and apoptosis pathways," Oncology Reports 37: 3449-3458, 2017.
Thijssen et al., "Dual TORK/DNA-PK inhibition blocks critical signaling pathways in chronic lymphocytic leukemia", Blood, vol. 28, pp. 574-583, Jul. 28, 2016.
Tian et al., "mTOR Signaling in Cancer and mTOR Inhibitors in Solid Tumor Targeting Therapy", Int. J. Mol. Sci., vol. 20. pp. 1-34, Feb. 11, 2019.
Tsukada et al., "Isolation and characterization of autophagy-defective mutants of *Saccharomyces cerevisiae*," FEBS Lett. 333: 169-17 4 (1993).
Ubersax et al., "Mechanisms of specificity in protein phosphorylation," Nat Rev Mol Cell Biol 8(7): 530-541 (2007).
Wagle et al., "Activating mTOR Mutations in a Patient with an Extraordinary Response on a Phase I Trial of Everolimus and Pazopanib," Cancer Discov, 2014, 4(5); 546-53.
Wang et al. "Targeting mTOR signaling overcomes acquired resistance to combined BRAF and MEK inhibition in BRAF-mutant melanoma", Oncogene, vol. 40, pp. 5590-5599, 2021.
What is Cancer [online]. NCI 2017 [retrieved 2017]. Retrieved from the internet: <https://www.cancer.gov/about-cancer/understanding/what-is-cancer>. (Year: 2017).
Xie et al., "Coordinate Autophagy and mTOR Pathway Inhibition Enhances Cell Death in Melonoma", Plos one, vol. 8. Issue 1, pp. 1-11, 2013.
Yang et al., "Inhibition of Mtorc1 by RAD001 (everolimus) potentiates the effects of 1,25-dihydroxyvitamin d3 to induce growth arrest and differentiation of AML cells in vitro and in vivo", Experimental Hematology, vol. 38, Issue 8, pp. 666-676, 2010.
Jung et al., "ULK1 inhibits the kinase activity of mTORC1 and cell proliferation," Autophagy 2011, vol. 7, No. 10, pp. 1212-1221.
Bush et al., "In Vitro Elucidation of Drug Combination Synergy in Treatment of Pancreatic Ductal Adenocarcinoma," Anticancer Research, 2018, vol. 38, pp. 1967-1977.
Obasaju et al., "Gemcitabine/Carboplatin in Patients with Metastatic Non-Small-Cell Lung Cancer: Phase II Study of 28-Day and 21-Day Schedules," Clinical Lung Cancer, 2005, vol. 7, No. 3, pp. 202-207.
Zhao et al., "Antitumor effedts and mechanisms of olaparib in combination with carboplatin and BKM120 on human triple-negative breast cancer cells," Oncol Rep, 2018, vol. 40, No. 6, pp. 3223-3234.

* cited by examiner

MACROCYCLIC ULK1/2 INHIBITORS

CROSS-REFERENCE TO RELATED APPLICATIONS

This application is a national stage application filed under 35 U.S.C. § 371 of International Patent Application No. PCT/US2021/018038 filed Feb. 12, 2021, entitled "MACROCYCLIC ULK1/2 INHIBITORS," which claims priority to U.S. Provisional Application No. 62/977,039 filed Feb. 14, 2020, entitled "Macrocyclic ULK1/2 Inhibitors," the disclosures of which are each hereby incorporated by reference in their entireties.

STATEMENT AS TO FEDERALLY SPONSORED RESEARCH

This invention was made with government support under T32 grant number 1T32CA211036 awarded by NIH/NCI. The government has certain rights in the invention.

BACKGROUND OF THE INVENTION

Autophagy is a central cellular mechanism for elimination of damaged proteins, protein complexes, and organelles. This conserved process plays crucial roles in the cellular response to nutrient deprivation and other stresses, in addition to being required for proper cellular and tissue homeostasis during embryonic development and in defense against pathogens. Defects in autophagy pathways are associated with certain human pathologies, including infectious diseases, neurodegenerative disorders, and cancer. In spite of these highly conserved fundamental cellular functions, the molecular and biochemical details of how autophagy is initiated for different cargoes, and the coordination of steps starting from autophagosome initiation to ultimate fusion with the lysosome remain poorly understood.

SUMMARY OF THE INVENTION

Provided herein are inhibitors of unc-51 like autophagy activating kinase (ULK) proteins. In some embodiments, the inhibitors inhibit ULK11. In some embodiments, the inhibitors are specific for ULK11. In some embodiments, the inhibitors inhibit both ULK1 and ULK2. In some instances, the inhibitors provided herein are useful for the treatment of various diseases, including cancer.

In many instances, ULK1 and ULK2 are important proteins that regulate autophagy in mammalian cells. In certain instances, ULK1 and ULK2 are activated under conditions of nutrient deprivation by several upstream signals, which is followed by the initiation of autophagy. The requirement for ULK1 and ULK2 in autophagy initiation has been studied in the context of nutrient deprivation. While ULK1 appears to be the most essential for autophagy, in some instances, ULK1 and ULK2 show high functional redundancy. The kinase domains of ULK1 and ULK2 share 78% sequence homology, suggesting, in some instances, ULK2 may compensate for the loss of ULK1 in some instances. In some instances, nutrient dependent autophagy may only be eliminated if both ULK1 and ULK2 are inhibited. In some instances, inhibition of ULK1 alone is sufficient, e.g. for providing a therapeutic benefit, such as in any method provided herein, for normalizing autophagy in a cancer cell, or other beneficial result. In other instances, inhibition of ULK1 and ULK2 results in a therapeutic benefit, such as tumor shrinkage, tumor cell death, or slowed rate of tumor growth.

In some embodiments, the compounds provided herein are inhibitors of ULK. In some embodiments, the compounds inhibit ULK11. In some embodiments, the compounds are ULK1 inhibitors. In some embodiments, the compounds are specific for ULK11. In some embodiments, the compounds inhibit both ULK1 and ULK2. In some embodiments, the diseases provided herein are treatable with an inhibitor specific for ULK11. In some instances, ULK2 may compensate for loss of ULK1 function. In some embodiments, the diseases provided herein require treatment with a compound that inhibits both ULK1 and ULK2.

Provided herein in certain embodiments are compounds useful as ULK inhibitors. In some embodiments, the compounds are useful for the treatment of various diseases, including cancer. Provided in certain embodiments herein is a compound having a structure of Formula (I):

Formula (I)

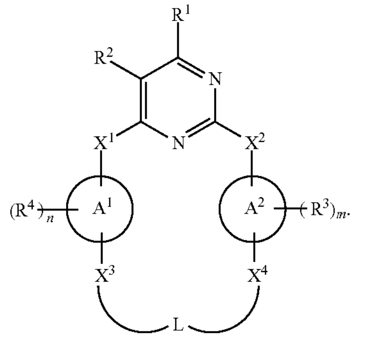

In some embodiments, $R^1$ is hydrogen, substituted or unsubstituted alkyl, substituted or unsubstituted heteroalkyl, or halogen;

$R^2$ is hydrogen, halogen, —CN, —OR, —SR, —S(=O)R, —$S(=O)_2R$, —$NO_2$, —NRR, —$NRS(=O)_2R$, —$S(=O)_2NRR$, —C(=O)R, —OC(=O)R, —C(=O)C(=O)R, —C(=O)OR, —C(=O)NROR, —OC(=O)OR, —C(=O)NRR, —OC(=O)NRR, —NRC(=O)NRR, —$NRS(=O)_2NRR$, —NRC(=O)R, —NRC(=O)O R, substituted or unsubstituted alkyl, substituted or unsubstituted heteroalkyl, substituted or unsubstituted aryl, or substituted or unsubstituted heteroaryl;

$X^1$, $X^2$, $X^3$, and $X^4$ are each independently absent, alkylene, —O—, —$NR^5$—, or —S—;

$A^1$ and $A^2$ are each independently carbocycle or heterocycle (e.g. aryl or heteroaryl);

each $R^3$ and $R^4$ is independently halogen, —CN, —OR, —SR, —S(=O)R, —$S(=O)_2R$, —$NO_2$, —NRR, —$NRS(=O)_2R$, —$S(=O)_2NRR$, —C(=O)R, —OC(=O)R, —C(=O)C(=O)R, —C(=O)OR, —C(=O)NROR, —OC(=O)OR, —C(=O)NRR, —OC(=O)NRR, —NRC(=O)NRR, —$NRS(=O)_2NRR$, —NRC(=O)R, —NRC(=O)OR, substituted or unsubstituted alkyl, substituted or unsubstituted heteroalkyl, substituted or unsubstituted aryl, or substituted or unsubstituted heteroaryl;

each $R^5$ is independently hydrogen, substituted or unsubstituted alkyl, substituted or unsubstituted heteroalkyl, substituted or unsubstituted aryl, or substituted or unsubstituted heteroaryl;

L is a chain of 3-12 (e.g., 3-8) atoms, wherein the chain is a substituted or unsubstituted alkylene or a substituted or unsubstituted heteroalkylene;

each R is independently hydrogen, substituted or unsubstituted alkyl, substituted or unsubstituted heteroalkyl, substituted or unsubstituted aryl, or substituted or unsubstituted heteroaryl;

n is an integer from 0-4 (or 0 to the ring size of $A^1$ minus 2); and m is an integer from 0-4 (or 0 to the ring size of $A^2$ minus 2), or pharmaceutically acceptable salt thereof.

In certain embodiments, any group that is optionally substituted is optionally substituted with one or more substituent. In some embodiments, any group that is substituted herein is substituted with one or more substituents. In certain embodiments herein, each substituent is independently selected from a halogen, oxo, —CN, —OR, —S(═O)$_2$R, —NRR, —S(═O)$_2$NRR, —C(═O)R, —OC(═O)R, —C(═O)OR, —OC(═O)OR, —C(═O)NRR, —OC(═O)NRR, —NRC(═O)NRR, —NRC(═O)R, alkyl, haloalkyl, heteroalkyl, hydroxyalkyl, and phenyl. In specific embodiments, the R group(s) of a substituent is not further substituted.

In some embodiments, in a compound of Formula (I), $R^1$ is hydrogen, alkyl optionally substituted with one or more $R^{10}$, or halogen.

In certain embodiments, $R^2$ is hydrogen, halogen, —CN, —OR$^{21}$, —SR$^{21}$, —S(═O)R$^{22}$, —S(═O)$_2$R$^{22}$, —NO$_2$, —NR$^{23}$R$^{24}$, —NR$^{21}$S(═O)$_2$R$^{22}$, —S(═O)$_2$NR$^{23}$R$^{24}$, —C(═O)R$^{22}$, —OC(═O)R$^{22}$, —C(═O)C(═O)R$^{22}$, —C(═O)OR$^{21}$, —C(═O)NR$^{21}$OR$^{21}$, —OC(═O)OR$^{21}$, —C(═O)NR$^{23}$R$^{24}$, —OC(═O)NR$^{23}$R$^{24}$, —NR$^{21}$C(═O)NR$^{23}$R$^{24}$, —NR$^{21}$S(═O)$_2$NR$^{23}$R$^{24}$, —NR$^{21}$C(═O)R$^{22}$, —NR$^{21}$C(═O)OR$^{21}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{20}$.

In some embodiments, $X^1$, $X^2$, $X^3$, and $X^4$ are each independently —O—, —NR$^5$—, or —S.

In certain embodiments, $A^1$ and $A^2$ are each independently aryl or heteroaryl. In certain embodiments, $A^1$ and $A^2$ are each independently 6-membered aryl or 6-membered heteroaryl.

In some embodiments, each $R^3$ is independently halogen, —CN, —OR$^{31}$, —SR$^{31}$, —S(═O)R$^{32}$, —S(═O)$_2$R$^{32}$, —NO$_2$, —NR$^{33}$R$^{34}$, —NR$^{31}$S(═O)$_2$R$^{32}$, —S(═O)$_2$NR$^{33}$R$^{34}$, —C(═O)R$^{32}$, —OC(═O)R$^{32}$, —C(═O)C(═O)R$^{32}$, —C(═O)OR$^{31}$, —C(═O)NR$^{31}$OR$^{31}$, —OC(═O)OR$^{31}$, —C(═O)NR$^{33}$R$^{34}$, —OC(═O)NR$^{33}$R$^{34}$, —NR$^{31}$C(═O)NR$^{33}$R$^{34}$, —NR$^{31}$S(═O)$_2$NR$^{33}$R$^{34}$, —NR$^{31}$C(═O)R$^{32}$, —NR$^{31}$C(═O)OR$^{31}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{30}$.

In some embodiments, each $R^4$ is independently halogen, —CN, —OR$^{41}$, —SR$^{41}$, —S(═O)R$^{42}$, —S(═O)$_2$R$^{42}$, —NO$_2$, —NR$^{43}$R$^{44}$, —NR$^{41}$S(═O)$_2$R$^{42}$, —S(═O)$_2$NR$^{43}$R$^{44}$, —C(═O)R$^{42}$, —OC(═O)R$^{42}$, —C(═O)C(═O)R$^{42}$, —C(═O)OR$^{41}$, —C(═O)NR$^{41}$OR$^{41}$, —OC(═O)OR$^{41}$, —C(═O)NR$^{43}$R$^{44}$, —OC(═O)NR$^{43}$R$^{44}$, —NR$^{41}$C(═O)NR$^{43}$R$^{44}$, —NR$^{41}$S(═O)$_2$NR$^{43}$R$^{44}$, —NR$^{41}$C(═O)R$^{42}$, —NR$^{41}$C(═O)OR$^{41}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{40}$.

In certain embodiments, each $R^5$ is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{50}$.

In some embodiments, L is a chain of 3-8 atoms. In specific embodiments, the chain is an alkylene chain or a heteroalkylene chain, either of which is optionally substituted with one or more $R^{60}$. In some embodiments, each atom in the heteroalkylene chain is independently selected from —CR$^6$R$^7$—, —NR$^8$—, —O—, or —S—.

In certain embodiments, each $R^6$ and $R^7$ are independently hydrogen, halogen, $C_1$-$C_6$ alkyl, cycloalkyl, heterocycloalkyl, aryl, or heteroaryl. In specific embodiments, wherein the alkyl, cycloalkyl, heterocycloalkyl, aryl, and heteroaryl are independently optionally substituted with one or more $R^{60}$. In some embodiments, $R^6$ and $R^7$ are taken together with the carbon to which they are attached to form a cycloalkyl or heterocycloalkyl optionally substituted with one or more $R^{60}$. In certain embodiments, $R^6$ and $R^7$ are taken together to form an oxo, or adjacent $R^6$ are taken together to form a double bond, or $R^6$ joins with an $R^6$ or $R^8$ from a different atom in the chain to form a cycloalkyl or heterocycloalkyl optionally substituted with one or more $R^{60}$;

In certain embodiments, each $R^1$ is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{80}$. In some embodiments, $R^8$ joins with an $R^6$ or $R^8$ from a different atom in the chain to form a heterocycloalkyl optionally substituted with one or more $R^{80}$ In certain embodiments, each $R^{10}$ is independently halogen, —CN, —OR$^a$, —S(═O)$_2$R$^b$, —NR$^c$R$^d$, —S(═O)$_2$NR$^c$R$^d$, —C(═O)R$^b$, —OC(═O)R$^b$, —C(═O)OR$^a$, —OC(═O)OR$^a$, —C(═O)NR$^c$R$^d$, —OC(═O)NR$^c$R$^d$, —NR$^a$C(═O)NR$^c$R$^d$, —NR$^a$C(═O)R$^b$, $C_1$-$C_6$ alkyl, $C_1$-$C_6$ haloalkyl, $C_1$-$C_6$ hydroxyalkyl, or phenyl. In some embodiments, each $R^{20}$ is independently halogen, —CN, —OR$^a$, —S(═O)$_2$ R$^b$, —NR$^c$R$^d$, —S(═O)$_2$NR$^c$R$^d$, —C(═O)R$^b$, —OC(═O)R$^b$, —C(═O)OR$^a$, —OC(═O)OR$^a$, —C(═O)NR$^c$R$^d$, —OC(═O)NR$^c$R$^d$, —NR$^a$C(═O)NR$^c$R$^d$, —NR$^a$C(═O)R$^b$, $C_1$-$C_6$ alkyl, $C_1$-$C_6$ haloalkyl, $C_1$-$C_6$ hydroxyalkyl, or phenyl.

In certain embodiments, each $R^{21}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one $R^{1a}$. In some embodiments, $R^{22}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1b}$.

In certain embodiments, $R^{23}$ and $R^{24}$ are each independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1c}$. In some embodiments, $R^{23}$ and $R^{24}$ are taken together with the nitrogen atom to which they are attached to form a heterocycloalkyl optionally substituted with one or more $R^{1d}$;

In some embodiments, each $R^{30}$ is independently halogen, —CN, —OR$^a$, —S(═O)$_2$R$^b$, —NR$^c$R$^d$, —S(═O)$_2$NR$^c$R$^d$, —C(═O)R$^b$, —OC(═O)R$^b$, —C(═O)OR$^a$, —OC(═O)OR$^a$, —C(═O)NR$^c$R$^d$, —OC(═O)NR$^c$R$^d$, —NR$^a$C(═O)NR$^c$R$^d$, —NR$^a$C(═O)R$^b$, $C_1$-$C_6$ alkyl, $C_1$-$C_6$ haloalkyl, $C_1$-$C_6$ hydroxyalkyl, or phenyl.

In certain embodiments, each $R^{31}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1a}$.

In some embodiments, each $R^{32}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1b}$. In certain embodiments, each $R^{33}$ and $R^{34}$ are each independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1c}$. In some embodiments, $R^{33}$ and $R^{34}$ are taken together with the nitrogen atom to which they are attached to form a heterocycloalkyl optionally substituted with one or more $R^{1d}$.

In certain embodiments, each $R^{40}$ is independently halogen, —CN, —$OR^a$, —S(═O)$_2R^b$, —$NR^cR^d$, —S(═O)$_2$ $NR^cR^d$, —C(═O)$R^b$, —OC(═O)$R^b$, —C(═O)$OR^a$, —OC(═O)$OR^a$, —C(═O)$NR^cR^d$, —OC(═O)$NR^cR^d$, —$NR^a$C(═O)$NR^cR^d$, —$NR^a$C(═O)$R^b$, $C_1$-$C_6$ alkyl, $C_1$-$C_6$ haloalkyl, $C_1$-$C_6$ hydroxyalkyl, or phenyl. In some embodiments, each $R^{41}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1a}$. In certain embodiments, each $R^{42}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more Rib. In some embodiments, each $R^{41}$ and $R^{44}$ are each independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1c}$. In certain embodiments, $R^{43}$ and $R^{44}$ are taken together with the nitrogen atom to which they are attached to form a heterocycloalkyl optionally substituted with one or more $R^{1d}$.

In some embodiments, each $R^{50}$ is independently halogen, —CN, —$OR^a$, —S(═O)$_2R^b$, —$NR^cR^d$, —S(═O)$_2NR^cR^d$, —C(═O)$R^b$, —OC(═O)$R^b$, —C(═O)$OR^a$, —OC(═O)$OR^a$, —C(═O)$NR^cR^d$, —OC(═O)$NR^cR^d$, —$NR^a$C(═O)$NR^cR^d$, —$NR^a$C(═O)$R^b$, $C_1$-$C_6$ alkyl, $C_1$-$C_6$ haloalkyl, $C_1$-$C_6$ hydroxyalkyl, or phenyl. In certain embodiments, each $R^{60}$ is independently halogen, —CN, —$OR^a$, —S(═O)$_2R^b$, —$NR^cR^d$, —S(═O)$_2NR^cR^d$, —C(═O)$R^b$, —OC(═O)$R^b$, —C(═O)$OR^a$, —OC(═O)$OR^a$, —C(═O)$NR^cR^d$, —OC(═O)$NR^cR^d$, —$NR^a$C(═O)$NR^cR^d$, —$NR^a$C(═O)$R^b$, $C_1$-$C_6$ alkyl, $C_1$-$C_6$ haloalkyl, $C_1$-$C_6$ hydroxyalkyl, or phenyl. In some embodiments, each $R^{80}$ is independently halogen, —CN, —$OR^a$, —S(═O)$_2R^b$, —$NR^cR^d$, —S(═O)$_2NR^cR^d$, —C(═O)$R^b$, —OC(═O)$R^b$, —C(═O)$OR^a$, —OC(═O)$OR^a$, —C(═O)$NR^cR^d$, —OC(═O)$NR^cR^d$, —$NR^a$C(═O)$NR^cR^d$, —$NR^a$C(═O)$R^b$, $C_1$-$C_6$ alkyl, $C_1$-$C_6$ haloalkyl, $C_1$-$C_6$ hydroxyalkyl, or phenyl.

In certain embodiments, each $R^{1a}$, $R^{1b}$, $R^{1c}$, and $R^{1d}$ are independently oxo, halogen, —CN, —$OR^a$, —S(═O)$_2R^b$, —$NR^cR^d$, —S(═O)$_2NR^cR^d$, —C(═O)$R^b$, —OC(═O)$R^b$, —C(═O)$OR^a$, —OC(═O)$OR^a$, —C(═O)$NR^cR^d$, —OC(═O)$NR^cR^d$, —$NR^a$C(═O)$NR^cR^d$, —$NR^a$C(═O)$R^b$, $C_1$-$C_6$ alkyl, $C_1$-$C_6$ haloalkyl, $C_1$-$C_6$ hydroxyalkyl, or phenyl. In some embodiments, each Ra is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more halogen, —OH, —$NH_2$, or $C_1$-$C_6$ alkyl. In certain embodiments, each $R^b$ is independently $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more halogen, —OH, —$NH_2$, or $C_1$-$C_6$ alkyl. In some embodiments, each $R^c$ and $R^d$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more halogen, —OH, —$NH_2$, or $C_1$-$C_6$ alkyl. In certain embodiments, $R^c$ and $R^d$ are taken together with the nitrogen atom to which they are attached to form a heterocycloalkyl optionally substituted with one or more halogen, —OH, —$NH_2$, or $C_1$-$C_6$ alkyl. In certain embodiments, n is an integer from 0-4. In some embodiments, m is an integer from 0-4.

In specific embodiments, the compound is a pharmaceutically acceptable salt of a compound of Formula (I).

In some embodiments, $R^1$ is hydrogen or halogen. In some embodiments, $R^1$ is hydrogen or fluorine. In some embodiments, $R^1$ is hydrogen. In some embodiments, each $R^{10}$ is independently halogen, —CN, —$OR^a$, $NR^cR^d$, —C(═O)$R^b$, —C(═O)$OR^a$, $C_1$-$C_6$ alkyl, $C_1$-$C_6$ haloalkyl, $C_1$-$C_6$ hydroxyalkyl, or phenyl. In some embodiments, each $R^{10}$ is independently halogen, —CN, or —OH.

In some embodiments, $R^2$ is halogen, —CN, —S(═O)$R^{22}$, —S(═O)$_2R^{22}$, —$NO_2$, —S(═O)$_2NR^{23}R^{24}$, —C(═O)$R^{22}$, —C(═O)$OR^{21}$, —C(═O)$NR^{21}OR^{21}$, —C(═O)$NR^{23}R^{24}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{20}$. In some embodiments, $R^2$ is halogen, —CN, —$NO_2$, or $C_1$-$C_6$ alkyl, wherein the alkyl is optionally substituted with one or more $R^{20}$. In some embodiments, $R^2$ is halogen, —CN, or —$CF_3$. In some embodiments, $R^2$ is Br, Cl, or —$CF_3$. In some embodiments, $R^2$ is —$CF_3$.

In some embodiments, each $R^{20}$ is independently halogen, —CN, —$OR^a$, $NR^cR^d$, —C(═O)$R^b$, —C(═O)$OR^a$, $C_1$-$C_6$ alkyl, $C_1$-$C_6$ haloalkyl, $C_1$-$C_6$ hydroxyalkyl, or phenyl. In some embodiments, each $R^{20}$ is independently halogen, —CN, or —OH.

In some embodiments, $A^1$ is phenyl or pyridyl substituted. In some embodiments, $A^1$ is phenyl substituted with n $R^4$ substituents. In some embodiments, $A^1$ is:

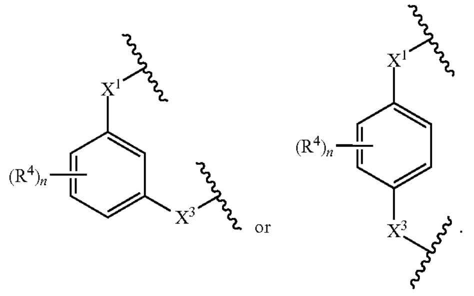

In specific embodiments, n is 1 or 2. In more specific embodiments, n is 1.

In some embodiments, each $R^4$ is independently halogen, —CN, —$OR^{41}$, —S(═O)$R^{42}$, —S(═O)$_2R^{42}$, —$NR^{41}$S(═O)$_2R^{42}$, —S(═O)$_2NR^{43}R^{44}$, —C(═O)$R^{42}$, —OC(═O)$R^{42}$, —C(═O)$OR^{41}$, —C(═O)$NR^{43}R^{44}$, —$NR^{41}$S(═O)$_2$ $NR^{43}R^{44}$, —$NR^{41}C$(═O)$R^{42}$, $C_1$-$C_6$ alkyl, or cycloalkyl wherein the alkyl and cycloalkyl are independently optionally substituted with one or more $R^{40}$. In some embodiments, each $R^4$ is independently halogen, —CN, —S(═O)$_2$ $R^{42}$, —$NR^{41}$S(═O)$_2R^{42}$, —S(═O)$_2NR^{43}R^{44}$, —C(═O) $NR^{43}R^{44}$, $C_1$-$C_6$ alkyl, or cycloalkyl. In some embodiments, each $R^4$ is independently fluorine, —C(═O)$NR^{43}R^{44}$ or $C_1$-$C_6$ alkyl. In some embodiments, each $R^4$ is independently, —C(═O)$NHR^{43}$ or $C_1$-$C_6$ alkyl. In some embodiments, n is 1 and $R^4$ is —C(═O)NH($C_1$-$C_6$ alkyl). In some embodiments, $R^4$ is

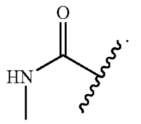

In some embodiments, each $R^{40}$ is independently halogen, —CN, —$OR^a$, $NR^cR^d$, —C(═O)$R^b$, —C(═O)$OR^a$, $C_1$-$C_6$ alkyl, $C_1$-$C_6$ haloalkyl, $C_1$-$C_6$ hydroxyalkyl, or phenyl. In some embodiments, wherein each $R^{40}$ is independently halogen, —CN, or —OH.

In some embodiments, $A^1$ is

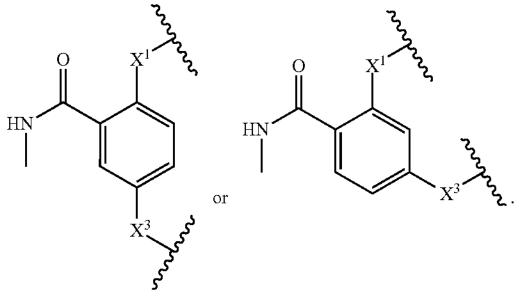

In some embodiments, $A^2$ is phenyl or pyridyl. In some embodiments, $A^2$ is phenyl. In some embodiments, $A^2$ is

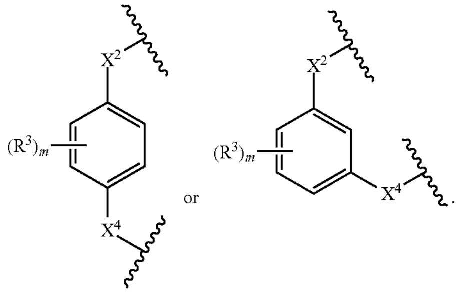

In some embodiments, each $R^3$ is independently halogen, —CN, —$OR^{31}$, —$SR^1$, —$NO_2$, —$NR^{33}R^{34}$, —S(═O)$_2$ $NR^{33}R^{34}$, —OC(═O)$R^{32}$, —C(═O)$OR^{31}$, —OC(═O) $OR^{31}$, —C(═O)$NR^{33}R^{34}$, —OC(═O)$NR^{33}R^{34}$, —$NR^{31}C$ (═O)$NR^{33}R^{34}$, —$NR^{31}C$(═O)$R^{32}$, —$NR^{31}C$(═O)$OR^{31}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{30}$. In some embodiments, each $R^3$ is independently halogen, —CN, —$OR^{31}$, —$SR^{31}$, —$NR^{33}R^{34}$, —OC(═O)$R^{32}$, —C(═O)$NR^{33}R^{34}$, —$NR^{31}C$ (═O)$R^{32}$, —$NR^{31}C$(═O)$OR^{31}$, $C_1$-$C_6$ alkyl, cycloalkyl, or aryl, wherein the alkyl, cycloalkyl, and aryl are independently optionally substituted with one or more $R^{30}$. In some embodiments, wherein each $R^3$ is independently halogen, —$OR^{31}$, —$NR^{33}R^{34}$, —OC(═O)$R^{32}$, —$NR^{31}C$(═O)$R^{32}$, —$NR^{31}C$(═O)$OR^{31}$, or $C_1$-$C_6$ alkyl. In some embodiments, each $R^3$ is independently fluorine, chlorine, bromine, —O($C_1$-$C_6$alkyl), —OH, —$NH_2$, or $C_1$-$C_6$ alkyl. In some embodiments, each $R^3$ is independently fluorine, chlorine, bromine, or —OMe. In some embodiments, each $R^3$ is —OMe.

In some embodiments, m is 1 or 2. In some embodiments, m is 1.

In some embodiments, each $R^{30}$ is independently halogen, —CN, —$OR^a$, $NR^cR^d$, —C(═O)$R^b$, —C(═O)$OR^a$, $C_1$-$C_6$ alkyl, $C_1$-$C_6$ haloalkyl, $C_1$-$C_6$ hydroxyalkyl, or phenyl. In some embodiments, each $R^{30}$ is independently halogen, —CN, or —OH. In some embodiments, $A^2$ is

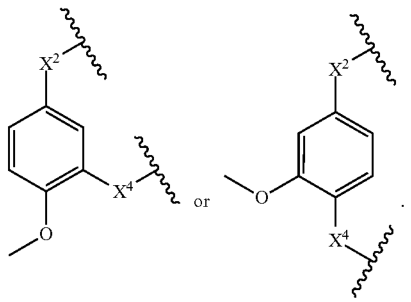

In some embodiments, $X^1$ is —O— or —$NR^5$—. In some embodiments, $X^1$ is —NH— or —N(Me)-. In some embodiments, $X^1$ is —NH—.

In some embodiments, $X^2$ is —O— or —$NR^5$—. In some embodiments, $X^2$ is —NH— or —N(Me)-. In some embodiments, $X^2$ is —NH—.

In some embodiments, $X^3$ is —O—. In some embodiments, $X^4$ is —O—.

In some embodiments, L is a chain of 3-8 atoms, wherein each atom in the chain is independently selected from —$CR^6R^7$— or —O—. In some embodiments, each $R^6$ and $R^7$ is independently hydrogen, $C_1$-$C_6$ alkyl, cycloalkyl, or heterocycloalkyl; wherein the alkyl, cycloalkyl, and heterocycloalkyl, are independently optionally substituted with one or more $R^{60}$; or adjacent $R^6$ are taken together to form a double bond. In some embodiments, each $R^6$ and $R^7$ is independently hydrogen, $C_1$-$C_6$ alkyl, or cycloalkyl; or adjacent $R^6$ are taken together to form a double bond. In specific embodiments, L is selected from (substituted or unsubstituted)

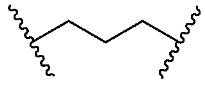,
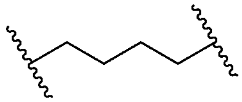,
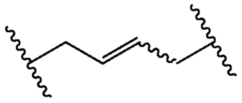,
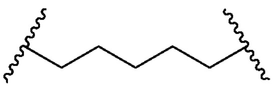,
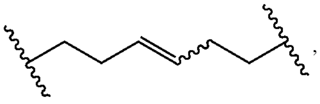,

-continued

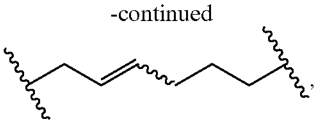
,
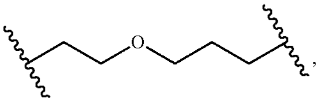
,
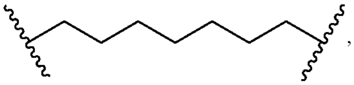
,
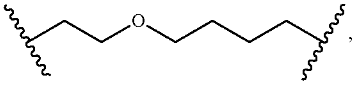
,
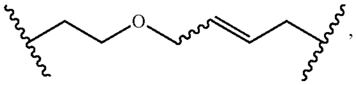
,
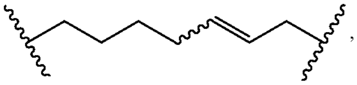
,
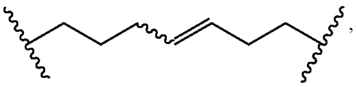
, and
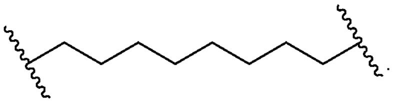
.

In one aspect, provided herein, is a pharmaceutical composition comprising the compound or pharmaceutically acceptable salt thereof of any one of the compounds provided herein and a pharmaceutically acceptable carrier. In some embodiments, the pharmaceutical composition is formulated for intravenous or intraperitoneal injection.

In one aspect, provided herein, is a method of treating a ULK1 or ULK2 mediated disease in a subject in need thereof, the method comprising administering to the subject a compound or pharmaceutical composition of any one of the compounds provided herein. In some embodiments, the ULK1 or ULK2 mediated disease is characterized by abnormal autophagy. In some embodiments, the abnormal autophagy has been therapeutically induced.

In some embodiments, the disease is cancer. In some embodiments, the cancer is lung cancer, breast cancer or pancreatic cancer. In some embodiments, the lung cancer is non-small cell lung cancer (NSCLC). In some embodiments, the cancer is pancreatic cancer. In some embodiments, the pancreatic cancer is pancreatic ductal adenocarcinoma. In some embodiments, the cancer is breast cancer. In some embodiments, the breast cancer is triple-negative breast cancer (TNBC).

In some embodiments, the disease is Tuberous Sclerosis Complex (TSC) or lymphangioleiomyomatosis (LAM).

In some embodiments, the compound is co-administered with an additional therapeutic agent. In some embodiments, the additional therapeutic agent is an mechanistic target of rapamycin (mTOR) inhibitor. In some embodiments, the additional therapeutic agent is carboplatin. In some embodiments, the additional therapeutic agent is a mitogen-activated protein kinase (MEK) inhibitor. In some embodiments, the additional therapeutic agent is trametinib. In some embodiments, the additional therapeutic agent is a poly (ADP-ribose) polymerase (PARP) inhibitor. In some embodiments, the additional therapeutic agent is olaparib. In some embodiments, the additional therapeutic agent is a standard of care therapy.

In some embodiments, administering the compound degrades autophagy-related protein 13 (ATG13) in the subject.

DETAILED DESCRIPTION OF THE INVENTION

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

"Alkyl" refers to a straight or branched hydrocarbon chain radical consisting solely of carbon and hydrogen atoms, which may optionally be unsaturated with one or more double or triple bonds, and preferably having from one to fifteen carbon atoms (i.e., $C_1$-$C_{15}$ alkyl). In certain embodiments, an alkyl comprises one to six carbon atoms (i.e., $C_1$-$C_6$ alkyl). In other embodiments, an alkyl comprises one to three carbon atoms (i.e., $C_1$-$C_3$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless otherwise specified, the term "alkyl" and its equivalents encompass linear, branched, and/or cyclic alkyl groups. In some instances, an "alkyl" comprises both cyclic and acyclic (linear and/or branched) alkyl components. When an alkyl group is described as "linear," the referenced alkyl group is not substituted with additional alkyl groups and is unbranched. When an alkyl group is described as "saturated," the referenced alkyl group does not contain any double or triple carbon-carbon bonds (e.g. alkene or alkyne).

"Alkylene" or "alkylene chain" refers to a divalent alkyl group, which may be saturated or unsaturated with one or more double or triple bonds.

"Aryl" refers to an aromatic monocyclic or aromatic multicyclic hydrocarbon ring system. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene.

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_{x-y}$alkyl" refers to saturated or unsaturated hydrocarbon groups, including straight-chain alkyl and branched-chain alkyl groups that contain from x to y carbons in the chain.

The terms "$C_{x-y}$alkenyl" and "$C_{x-y}$alkynyl" refer to unsaturated aliphatic groups analogous in length and possible substitution to the alkyls described above, but that contain at least one double or triple bond respectively.

"Cycloalkyl" refers to a saturated ring in which each atom of the ring is carbon. Cycloalkyl may include monocyclic and polycyclic rings such as 3- to 10-membered monocyclic rings, 6- to 12-membered fused bicyclic rings, 6- to 12-membered spirocyclic rings, and 6- to 12-membered bridged rings. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo [2.2.1]heptanyl), norbornenyl, decalinyl, 7,7-dimethyl-bicyclo[2.2.1]heptanyl, and the like.

"Halo" or, alternatively, "halogen" or "halide," means fluoro, chloro, bromo or iodo. In some embodiments, halo is fluoro, chloro, or bromo.

"Haloalkyl" refers to an alkyl radical, as defined above, that is substituted by one or more halo radicals, for example, trifluoromethyl, dichloromethyl, bromomethyl, 2,2,2-trifluoroethyl, 1-chloromethyl-2-fluoroethyl, and the like. In some embodiments, the alkyl part of the haloalkyl radical is optionally substituted as described herein.

"Heteroalkyl" refers to an alkyl group wherein one or more of the carbons of the alkyl group is replaced with a heteroatom. Exemplary heteroatoms include N, O, Si, P, B, and S atoms, preferably N, O and S. Note that valency of heteroatoms may not be identical to that of a carbon atom, so, for example, a methylene ($CH_2$) of an alkyl may be replaced with an NH group, S group, O group, or the like in a heteroalkyl.

"Heteroalkylene" refers to an alkylene group wherein one or more of the carbons of the alkylene group is replaced with a heteroatom. Exemplary heteroatoms include N, O, Si, P, B, and S atoms, preferably N, O and S.

"Heterocycloalkyl" refers to a saturated or unsaturated (e.g., non-aromatic) ring with carbon atoms and at least one heteroatom (e.g., a cycloalkyl wherein one or more of the carbon groups is substituted with a heteroatom). Exemplary heteroatoms include N, O, Si, P, B, and S atoms.

Heterocycloalkyl may include monocyclic and polycyclic rings such as 3- to 10-membered monocyclic rings, 6- to 12-membered fused bicyclic rings, 6- to 12-membered spirocyclic rings, and 6- to 12-membered bridged rings. The heteroatoms in the heterocycloalkyl radical are optionally oxidized. One or more nitrogen atoms, if present, are optionally quaternized. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heteroaryl" refers to an aromatic ring comprising carbon atoms and one or more heteroatoms. Exemplary heteroatoms include N, O, Si, P, B, and S atoms. As used herein, the heteroaryl ring may be selected from monocyclic or bicyclic and fused or bridged ring systems rings wherein at least one of the rings in the ring system is aromatic, i.e., it contains a cyclic, delocalized $(4n+2)$ $\pi$-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl).

The term "salt" or "pharmaceutically acceptable salt" refers to salts derived from a variety of organic and inorganic counter ions well known in the art. Pharmaceutically acceptable acid addition salts may be formed with inorganic acids and organic acids. Inorganic acids from which salts are derived include, for example, hydrochloric acid, hydrobromic acid, sulfuric acid, nitric acid, phosphoric acid, and the like. Organic acids from which salts are derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts may be formed with inorganic and organic bases. Inorganic bases from which salts are derived include, for example, sodium, potassium, lithium, ammonium, calcium, magnesium, iron, zinc, copper, manganese, aluminum, and the like. Organic bases from which salts are derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier is "acceptable" in the sense of being compatible with the other ingredients of the formulation and not injurious to the patient. Some examples of materials which serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. In embodiments where it is unspecified whether a group is substituted or unsubstituted, it is intended that the group is unsubstituted.

Substituents may include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro ($—NO_2$), imino (=N—H), oximo (=N—OH), hydrazino ($=N—NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_1R^a$ (where t is 1 or 2), $—R^b—S(O)_1R^a$ (where t is 1 or 2), $—R^b—S(O)_tOR^a$ (where t is 1 or 2), and $—R^b—S(O)_1N(R^a)_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro ($—NO_2$), imino (=N—H), oximo (=N—OH), hydrazine ($=N—NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_1R^a$ (where t is 1 or 2), $—R^b—S(O)_1R^a$ (where t is 1 or 2), $—R^b—S(O)_1OR^a$ (where t is 1 or 2) and $—R^b—S(O)_1N(R^a)_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro ($—NO_2$), imino (=N—H), oximo (=N—OH), hydrazine ($=N—NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(Ra)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_1R^a$ (where t is 1 or 2), $—R^b—S(O)_1R^a$ (where t is 1 or 2), $—R^b—S(O)_tOR^a$ (where t is 1 or 2) and $—R^b—S(O)_1N(R^a)_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain.

The terms "treat," "treating" or "treatment," as used herein, may include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

In various instances, "may" refers to optional alternatives to be used in the alternative or in addition to other specified components.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Autophagy

In certain instances, autophagy is a cellular response to loss of nutrients in which cells catabolize various proteins and organelles to provide building blocks and critical metabolites needed for cell survival. In some instances, autophagy plays an important homeostatic role in many tissues by removing protein aggregates and defective organelles that accumulate with cellular damage over time. While genetics first defined the core components of autophagy conserved across all eukaryotes, the molecular details of how the different autophagy complexes regulate one another and the precise temporal and spatial ordering of biochemical events involved in autophagy induction are typically considered to be poorly understood currently.

In healthy individuals, normal autophagy is, in certain instances, an important process for balancing sources of energy at critical times in development and in response to nutrient stress. In certain instances, autophagy also plays a housekeeping role in removing misfolded or aggregated proteins, clearing damaged organelles, such as mitochondria, endoplasmic reticulum and peroxisomes, as well as eliminating intracellular pathogens. Thus, autophagy is often thought of as a survival mechanism. In various instances, autophagy is either non-selective or selective in the removal of specific organelles, ribosomes and protein aggregates. In addition to elimination of intracellular aggregates and damaged organelles, in certain instances, autophagy promotes cellular senescence and cell surface antigen presentation, protects against genome instability and prevents or inhibits necrosis, giving it an important role in preventing, treating, or inhibiting diseases such as cancer, neurodegeneration, cardiomyopathy, diabetes, liver disease, autoimmune diseases and infections.

In some instances, defects in autophagy pathways are associated with a number of human pathologies, including infectious diseases, neurodegenerative disorders, and cancer. In some instances, the role of autophagy differs in different stages of cancer development; for example, in some instances, initially, autophagy has a preventive effect against cancer, but once a tumor develops, the cancer cells, in certain instances, utilize autophagy for their own cytoprotection. In some cancers, the mutations that cause uncontrolled cell growth which results in the formation of tumors or other cancerous tissue also effectuates changes in autophagy. In some instances, these changes in the autophagic pathways in the cancer cells results in increased survivability and durability of cancer cells. In some instances, this leads to the cells resisting apoptosis and cell death in response to standard cancer treatments, thus reducing the efficacy of cancer therapeutics. In certain instances, rather than killing the cancer cells, the therapeutics merely have the effect of arresting cancer tissue growth, with the cancer tissue entering a cystostatic phase upon treatment. Consequently, in some instances, the cancerous tissue is not killed during treatment, the growth is simply arrested. Upon cessation of treatment, the cancerous tissue is able to resume growth, thus increasing symptoms and complications for the patient. In light of this, in some instances, the addition of a therapeutic that disrupts autophagy has the effect of converting the cytostatic response of the cancer cells to cancer cell death.

In certain cancers, the changes in autophagy caused by the cancer are important for the survival of the cancer cells. As the mutations that cause cancer result in uncontrolled cell growth, in some instances, these cells rely on autophagy to properly regulate the consumption of nutrients to ensure the survival of the cells in conditions that would cause the death of a healthy cell. Thus, methods of inhibiting autophagy in cells present, in certain instances, a method of treating cancer without the need of an additional cancer therapeutic. Thus, methods of inhibiting autophagy in cells present, in certain instances, a method of treating cancer without the need of an additional cancer therapeutic.

ULK1 and ULK2

In many instances, ULK1 and/or ULK2 are important proteins in regulating autophagy in mammalian cells. In certain instances, ULK1 and/or ULK2 are activated under conditions of nutrient deprivation by several upstream signals, which is followed by the initiation of autophagy. The requirement for ULK1 and/or ULK2 in autophagy initiation has been studied in the context of nutrient deprivation.

In certain instances, ULK1 complex, combining ULK1, ATG13, FIP200 (focal adhesion kinase family interacting protein of 200 kDa), and autophagy-related protein 101 (ATG101) is one of the first protein complexes that comes in to play in the initiation and formation of autophagosomes when an autophagic response is initiated. Additionally, ULK1 is considered to be unique as a core conserved component of the autophagy pathway which is a serine/threonine kinase, making it a particularly unique target of opportunity for the development of compounds to control autophagy. Equally importantly for a clinical therapeutic index for agents inhibiting ULK1, mice genetically engineered to completely lack ULK1 are viable without significant pathology. Thus, in many instances, a ULK1 selective kinase inhibitor is well tolerated by normal tissues, but not by tumor cells that have become reliant on ULK1 mediated autophagy for survival.

In some instances, ULK2 takes over the functional role of ULK1 when ULK1 function has been inhibited. Thus, in some cases, an inhibitor that is effective for both ULK1 and ULK2 is desirable to mitigate this effect.

Compounds

The present disclosure provides compounds and salts, and formulations thereof, for use in treating various diseases. In some embodiments, the compounds are ULK inhibitors. In some embodiments, the compounds of the present disclosure are ULK1 inhibitors. In some embodiments, the compounds of the present disclosure are specific ULK1 inhibitors. In some embodiments, the compounds are inhibitors of both ULK1 and ULK2.

In one aspect, the present disclosure provides a compound having a structure of Formula (I):

Formula (I)

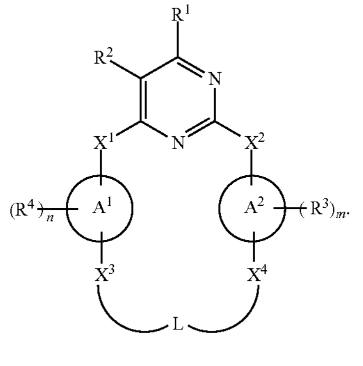

The substituents of such compounds are described herein, such as wherein;

$R^1$ is hydrogen, alkyl optionally substituted with one or more $R^{10}$, or halogen;

$R^2$ is hydrogen, halogen, —CN, —$OR^{21}$, —$SR^{21}$, —S(═O)$R^{22}$, —S(═O)$_2R^{22}$, —$NO_2$, —$NR^{23}R^{24}$, —$NR^{21}$S(═O)$_2R^{22}$, —S(═O)$_2NR^{23}R^{24}$, —C(═O)$R^{22}$, —OC(═O)$R^{22}$, —C(═O)C(═O)$R^{22}$, —C(═O)$OR^{21}$, —C(═O)$NR^{21}OR^{21}$, —OC(═O)$OR^{21}$, —C(═O)$NR^{23}R^{24}$, —OC(═O)$NR^{23}R^{24}$, —$NR^{21}$C(═O)$NR^{23}R^{24}$, —$NR^{21}$S(═O)$_2NR^{23}R^{24}$, —$NR^{21}$C(═O)$R^{22}$, —$NR^{21}$C(═O)$OR^{21}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{20}$, $X^1$, $X^2$, $X^3$, and $X^4$ are each independently absent, alkylene, —O—, —$NR^5$—, or —S—;

$A^1$ and $A^2$ are each independently carbocycle or heterocarbocycle (e.g. aryl or heteroaryl);

each $R^3$ is independently halogen, —CN, —$OR^{31}$, —$SR^{31}$, —S(═O)$R^{32}$, —S(═O)$_2R^{32}$, —$NO_2$, —$NR^{33}R^{34}$, —$NR^{31}$S(═O)$_2R^{32}$, —S(═O)$_2NR^{33}R^{34}$, —C(═O)$R^{32}$, —OC(═O)$R^{32}$, —C(═O)C(═O)$R^{32}$, —C(═O)$OR^{31}$, —C(═O)$NR^{31}OR^{31}$, —OC(═O)$OR^{31}$, —C(═O)$NR^{33}R^{34}$, —OC(═O)$NR^{33}R^{34}$, —$NR^{31}$C(═O)$NR^{33}R^{34}$, —$NR^{31}$S(═O)$_2NR^{33}R^{34}$, —$NR^{31}$C(═O)$R^{32}$, —$NR^{31}$C(═O)$OR^{31}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{30}$;

each $R^4$ is independently halogen, —CN, —$OR^{41}$, —$SR^{41}$, —S(═O)$R^{42}$, —S(═O)$_2R^{42}$, —$NO_2$, —$NR^{43}R^{44}$, —$NR^{41}$S(═O)$_2R^{42}$, —S(═O)$_2NR^{43}R^{44}$, —C(═O)$R^{42}$, —OC(═O)$R^{42}$, —C(═O)C(═O)$R^{42}$, —C(═O)$OR^{41}$, —C(═O)$NR^{41}OR^{41}$, —OC(═O)$OR^{41}$, —C(═O)$NR^{43}R^{44}$, —OC(═O)$NR^{43}R^{44}$, —$NR^{41}$C(═O)$NR^{43}R^{44}$, —$NR^{41}$S(═O)$_2NR^{43}R^{44}$, —$NR^{41}$C(═O)$R^{42}$, —$NR^{41}$C(═O)$OR^{41}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{40}$;

each $R^1$ is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{50}$;

L is a chain of 3-12 atoms, wherein the chain is an alkylene chain or a heteroalkylene chain, wherein each atom in the heteroalkylene chain is independently selected from —$CR^6R^7$—, —$NR^8$—, —O—, or —S—;

each $R^6$ and $R^7$ is independently hydrogen, halogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{60}$;

or $R^6$ and $R^7$ are taken together with the carbon to which they are attached to form a cycloalkyl or heterocycloalkyl optionally substituted with one or more $R^{60}$;

or $R^6$ and $R^7$ are taken together to form an oxo, or adjacent $R^6$ are taken together to form a double bond, or $R^6$ joins with an $R^6$ or $R^8$ from a different atom in the chain to form a cycloalkyl or heterocycloalkyl optionally substituted with one or more $R^{60}$;

each $R^8$ is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{80}$;

or $R^8$ joins with an $R^6$ or $R^8$ from a different atom in the chain to form a heterocycloalkyl optionally substituted with one or more $R^{80}$;

each $R^{10}$ is independently halogen, —CN, —$OR^a$, —S(═O)$_2R^b$, —$NR^cR^d$, —S(═O)$_2NR^cR^d$, —C(═O)$R^b$, —OC(═O)$R^b$, —C(═O)$OR^a$, —OC(═O)$OR^a$, —C(═O)$NR^cR^d$, —OC(═O)$NR^cR^d$, —$NR^a$C(═O)$NR^cR^d$, —$NR^a$C(═O)$R^b$, $C_1$-$C_6$ alkyl, $C_1$-$C_6$ haloalkyl, $C_1$-$C_6$ hydroxyalkyl, or phenyl;

each $R^{20}$ is independently halogen, —CN, —$OR^a$, —S(═O)$_2R^b$, —$NR^cR^d$, —S(═O)$_2NR^cR^d$, —C(═O)$R^b$, —OC(═O)$R^b$, —C(═O)$OR^a$, —OC(═O)$OR^a$, —C(═O)$NR^cR^d$, —OC(═O)$NR^cR^d$, —$NR^a$C(═O)$NR^cR^d$, —$NR^a$C(═O)$R^b$, $C_1$-$C_6$ alkyl, $C_1$-$C_6$ haloalkyl, $C_1$-$C_6$ hydroxyalkyl, or phenyl;

each $R^{21}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one $R^{1a}$;

$R^{22}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1b}$;

$R^{23}$ and $R^{24}$ are each independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1c}$;

or $R^{23}$ and $R^{24}$ are taken together with the nitrogen atom to which they are attached to form a heterocycloalkyl optionally substituted with one or more $R^{1d}$;

each $R^{30}$ is independently halogen, —CN, —$OR^a$, —S(═O)$_2R^b$, —$NR^cR^d$, —S(═O)$_2NR^cR^d$, —C(═O)$R^b$, —OC(═O)$R^b$, —C(═O)$OR^a$, —OC(═O)$OR^a$, —C(═O)$NR^cR^d$, —OC(═O)$NR^cR^d$, —$NR^a$C(═O)$NR^cR^d$, —$NR^a$C(═O)$R^b$, $C_1$-$C_6$ alkyl, $C_1$-$C_6$ haloalkyl, $C_1$-$C_6$ hydroxyalkyl, or phenyl;

each $R^{31}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1a}$;

each $R^{32}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1b}$;

each $R^{33}$ and $R^{34}$ are each independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1b}$;

or $R^{33}$ and $R^{34}$ are taken together with the nitrogen atom to which they are attached to form a heterocycloalkyl optionally substituted with one or more $R^{1d}$;

each $R^{40}$ is independently halogen, —CN, —$OR^a$, —S(═O)$_2R^b$, —$NR^cR^d$, —S(═O)$_2NR^cR^d$, —C(═O)$R^b$, —OC(═O)$R^b$, —C(═O)$OR^a$, —OC(═O)$OR^a$, —C(═O)$NR^cR^d$, —OC(═O)$NR^cR^d$, —$NR^a$C(═O)

$NR^cR^d$, $-NR^aC(=O)R^b$, $C_1$-$C_6$ alkyl, $C_1$-$C_6$ haloalkyl, $C_1$-$C_6$ hydroxyalkyl, or phenyl each $R^{41}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1a}$;

$R^{42}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1b}$;

$R^{43}$ and $R^{44}$ are each independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{1c}$;

or $R^{43}$ and $R^{44}$ are taken together with the nitrogen atom to which they are attached to form a heterocycloalkyl optionally substituted with one or more $R^d$;

each $R^{50}$ is independently halogen, —CN, $-OR^a$, $-S(=O)_2R^b$, $-NR^cR^d$, $-S(=O)_2NR^cR^d$, $-C(=O)R^b$, $-OC(=O)R^b$, $-C(=O)OR^a$, $-OC(=O)OR^a$, $-C(=O)NR^cR^d$, $-OC(=O)NR^cR^d$, $-NR^aC(=O)NR^cR^d$, $-NR^aC(=O)R^b$, $C_1$-$C_6$ alkyl, $C_1$-$C_6$ haloalkyl, $C_1$-$C_6$ hydroxyalkyl, or phenyl;

each $R^{60}$ is independently halogen, —CN, $-OR^a$, $-S(=O)_2R^b$, $-NR^cR^d$, $-S(=O)_2NR^cR^d$, $-C(=O)R^b$, $-OC(=O)R^b$, $-C(=O)OR^a$, $-OC(=O)OR^a$, $-C(=O)NR^cR^d$, $-OC(=O)NR^cR^d$, $-NR^aC(=O)NR^cR^d$, $-NR^aC(=O)R^b$, $C_1$-$C_6$ alkyl, $C_1$-$C_6$ haloalkyl, $C_1$-$C_6$ hydroxyalkyl, or phenyl;

each $R^{80}$ is independently halogen, —CN, $-OR^a$, $-S(=O)_2R^b$, $-NR^cR^d$, $-S(=O)_2NR^cR^d$, $-C(=O)R^b$, $-OC(=O)R^b$, $-C(=O)OR^a$, $-OC(=O)OR^a$, $-C(=O)NR^cR^d$, $-OC(=O)NR^cR^d$, $-NR^aC(=O)NR^cR^d$, $-NR^aC(=O)R^b$, $C_1$-$C_6$ alkyl, $C_1$-$C_6$ haloalkyl, $C_1$-$C_6$ hydroxyalkyl, or phenyl;

each $R^{1a}$, $R^{1b}$, $R^{1c}$, and $R^{1d}$ are independently oxo, halogen, —CN, $-OR^a$, $-S(=O)_2R^b$, $-NR^cR^d$, $-S(=O)_2NR^cR^d$, $-C(=O)R^b$, $-OC(=O)R^b$, $-C(=O)OR^a$, $-OC(=O)OR^a$, $-C(=O)NR^cR^d$, $-OC(=O)NR^cR^d$, $-NR^aC(=O)NR^cR^d$, $-NR^aC(=O)R^b$, $C_1$-$C_6$ alkyl, $C_1$-$C_6$ haloalkyl, $C_1$-$C_6$ hydroxyalkyl, or phenyl;

each $R^a$ is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more halogen, —OH, $-NH_2$, or $C_1$-$C_6$ alkyl;

each $R^b$ is independently $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more halogen, —OH, $-NH_2$, or $C_1$-$C_6$ alkyl;

each $R^c$ and $R^d$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more halogen, —OH, $-NH_2$, or $C_1$-$C_6$ alkyl;

or $R^c$ and $R^d$ are taken together with the nitrogen atom to which they are attached to form a heterocycloalkyl optionally substituted with one or more halogen, —OH, $-NH_2$, or $C_1$-$C_6$ alkyl;

n is an integer from 0-4; and m is an integer from 0-4, or pharmaceutically acceptable salt thereof.

In some embodiments, $R^1$ is hydrogen or halogen. In some embodiments, $R^1$ is hydrogen or fluorine. In some embodiments, $R^1$ is hydrogen.

In some embodiments, each $R^{10}$ is independently halogen, —CN, $-OR^a$, $NR^cR^d$, $-C(=O)R^b$, $-C(=O)OR^a$, $C_1$-$C_6$ alkyl, $C_1$-$C_6$ haloalkyl, $C_1$-$C_6$ hydroxyalkyl, or phenyl. In some embodiments, each $R^{10}$ is halogen, —CN, —OH, —OMe, or $-NH_2$. In some embodiments, each $R^{10}$ is independently halogen, —CN, or —OH.

In some embodiments, $R^2$ is halogen, —CN, $-S(=O)R^{22}$, $-S(=O)_2R^{22}$, $-NO_2$, $-S(=O)_2NR^{23}R^{24}$, $-C(=O)R^{22}$, $-C(=O)OR^{21}$, $-C(=O)NR^{21}OR^{21}$, $-C(=O)NR^{23}R^{24}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{20}$. In some embodiments, $R^2$ is halogen, —CN, $-NO_2$, or $C_1$-$C_6$ alkyl, wherein the alkyl is optionally substituted with one or more $R^{20}$. In some embodiments, $R^2$ is halogen, —CN, or $-CF_3$. In some embodiments, $R^2$ is Br, Cl, or $-CF_3$. In some embodiments, $R^2$ is $-CF_3$.

In some embodiments, each $R^{20}$ is independently halogen, —CN, $-OR^a$, $NR^cR^d$, $-C(=O)R^b$, $-C(=O)OR^a$, $C_1$-$C_6$ alkyl, $C_1$-$C_6$ haloalkyl, $C_1$-$C_6$ hydroxyalkyl, or phenyl. In some embodiments, each $R^{20}$ is independently halogen, —CN, or —OH.

In some embodiments, $A^1$ is aryl or heteroaryl. In some embodiments, $A^1$ is phenyl or pyridyl substituted with n $R^4$ substituents. In some embodiments, $A^1$ is phenyl substituted with n $R^4$ substituents. In some embodiments, $A^1$ is 6-membered heteroaryl substituted with n $R^4$ substituents. In some embodiments, $A^1$ is pyridyl substituted with n $R^4$ substituents. In some embodiments, $A^1$ is

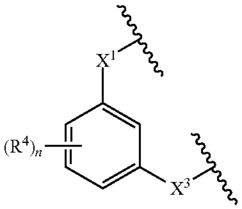

or

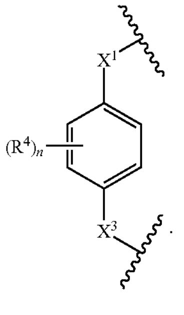

.

In some embodiments, n is 0, 1, or 2. In some embodiments, n is 1 or 2. In some embodiments, n is 1. In some embodiments, n is 0 or 1. In some embodiments, n is 0.

In some embodiments, each $R^4$ is independently halogen, —CN, $-OR^{41}$, $-S(=O)R^{42}$, $-S(=O)_2R^{42}$, $-NR^{41}S(=O)_2R^{42}$, $-S(=O)_2NR^{43}R^{44}$, $-C(=O)R^{42}$, $-OC(=O)R^{42}$, $-C(=O)OR^{41}$, $-C(=O)NR^{43}R^{44}$, $-NR^{41}S(=O)_2NR^{43}R^{44}$, $-NR^{41}C(=O)R^{42}$, $C_1$-$C_6$ alkyl, or cycloalkyl wherein the alkyl and cycloalkyl are independently optionally substituted with one or more $R^{40}$. In some embodiments, each $R^4$ is independently halogen, —CN, $-S(=O)_2R^{42}$, $-NR^{41}S(=O)_2R^{42}$, $-S(=O)_2NR^{43}R^{44}$, $-C(=O)NR^{43}R^{44}$, $C_1$-$C_6$ alkyl, or cycloalkyl. In some embodiments, each $R^4$ is independently fluorine, $-C(=O)NR^{43}R^{44}$, $-O(C_1$-$C_c$ alkyl) or $C_1$-$C_6$ alkyl. In some embodiments, each $R^4$ is independently fluorine, $-C(=O)NR^{43}R^{44}$ or $C_1$-$C_6$ alkyl. In some embodiments, each $R^4$ is independently, $-C(=O)NHR^{43}$ or $C_1$-$C_6$ alkyl. In some embodiments, $R^4$ is

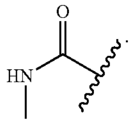

In some embodiments, n is 1 and $R^4$ is —C(═O)NH($C_1$-$C_6$ alkyl).

In some embodiments, each $R^{40}$ is independently halogen, —CN, —$OR^a$, $NR^cR^d$, —C(═O)$R^b$, —C(═O)$OR^a$, $C_1$-$C_6$ alkyl, $C_1$-$C_6$ haloalkyl, $C_1$-$C_6$ hydroxyalkyl, or phenyl. In some embodiments, each $R^{40}$ is independently halogen, —CN, or —OH.

In some embodiments, $A^1$ is

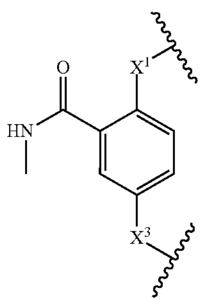

or

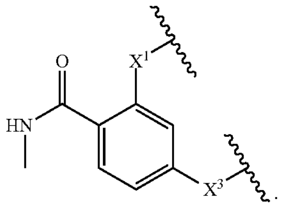

.

In some embodiments, $A^2$ is aryl or heteroaryl. In some embodiments, $A^2$ is phenyl or pyridyl substituted with m $R^3$ substituents. In some embodiments, $A^2$ is phenyl substituted with m $R^3$ substituents. In some embodiments, $A^2$ is pyridyl substituted with m $R^3$ substituents. In some embodiments, $A^2$ is 6-membered heteroaryl substituted with m $R^3$ substituents. In some embodiments, $A^2$ is

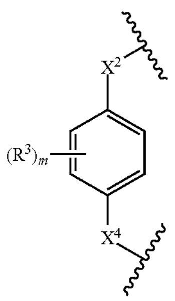

or

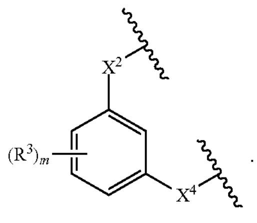

.

In some embodiments, each $R^3$ is independently halogen, —CN, —$OR^{31}$, —$SR^{31}$, —$NO_2$, —$NR^{33}R^{34}$, —S(═O)$_2$ $NR^{33}R^{34}$, —OC(═O)$R^{32}$, —C(═O)$OR^{31}$, —OC(═O)$OR^{31}$, —C(═O)$NR^{33}R^{34}$, —OC(═O)$NR^{33}R^{34}$, —$NR^1$C(═O)$NR^{33}R^{34}$, —$NR^{31}$C(═O)$R^{32}$, —$NR^{31}$C(═O)$OR^{31}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one or more $R^{30}$. In some embodiments, each $R^3$ is independently halogen, —CN, —$OR^{31}$, —$SR^{31}$, —$NR^{33}R^{34}$, —OC(═O)$R^{32}$, —C(═O)$NR^{33}R^{34}$, —$NR^{31}$C(═O)$R^{32}$, —$NR^{31}$C(═O)$OR^{31}$, $C_1$-$C_6$ alkyl, cycloalkyl, or aryl, wherein the alkyl, cycloalkyl, and aryl are independently optionally substituted with one or more $R^{30}$. In some embodiments, wherein each $R^3$ is independently halogen, —$OR^3$, —$NR^{33}R^{34}$, —OC(═O)$R^{32}$, —NR C(═O)$R^{32}$, —$NR^1$C(═)$OR^{31}$, or $C_1$-$C_6$ alkyl. In some embodiments, each $R^3$ is independently fluorine, chlorine, bromine, —O($C_1$-$C_6$alkyl), —OH, —$NH_2$, or $C_1$-$C_6$ alkyl. In some embodiments, each $R^3$ is independently fluorine, chlorine, bromine, or —OMe. In some embodiments, each $R^3$ is —OMe.

In some embodiments, m is 0, 1, or 2. In some embodiments, m is 1 or 2. In some embodiments, m is 0 or 1. In some embodiments, m is 1. In some embodiments, m is 0.

In some embodiments, each $R^{30}$ is independently halogen, —CN, —$OR^a$, $NR^cR^d$, —C(═O)$R^b$, —C(═O)$OR^a$, $C_1$-$C_6$ alkyl, $C_1$-$C_6$ haloalkyl, $C_1$-$C_6$ hydroxyalkyl, or phenyl. In some embodiments, each $R^{30}$ is independently halogen, —CN, or —OH. In some embodiments, $A^2$ is

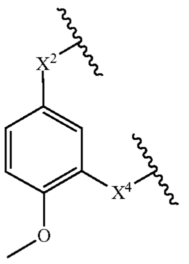

or

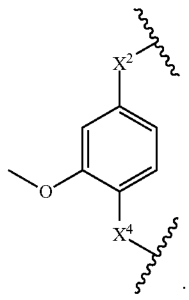

.

In some embodiments, $X^1$ is —S— —O— or —$NR^5$—. In some embodiments, $X^1$ is —O— or —$NR^5$—. In some embodiments, $X^1$ is —NH— or —N(Me)-. In some embodiments, $X^1$ is —NH—. In some embodiments, $X^1$ is —O—. In some embodiments, $X^1$ is absent. In some embodiments, $X^1$ is alkylene.

In some embodiments, $X^2$ is —S—, —O— or —$NR^5$—. In some embodiments, $X^2$ is —O— or —$NR^5$—. In some embodiments, $X^2$ is —NH— or —N(Me)-. In some embodiments, $X^2$ is —NH—. In some embodiments, $X^2$ is —O—. In some embodiments, $X^2$ is absent. In some embodiments, $X^2$ is alkylene.

In some embodiments, $X^3$ is —S—, —O— or —$NR^5$—. In some embodiments, $X^3$ is —O— or —$NR^5$—. In some embodiments, $X^3$ is —O— or —NH—. In some embodiments, $X^3$ is —O—. In some embodiments, $X^3$ is absent. In some embodiments, $X^3$ is alkylene.

In some embodiments, $X^4$ is —S—, —O— or —$NR^5$—. In some embodiments, $X^4$ is —O— or —$NR^5$—. In some embodiments, $X^4$ is —O— or —NH—. In some embodiments, $X^4$ is —O—. In some embodiments, $X^4$ is absent. In some embodiments, $X^4$ is alkylene.

In some embodiments, L is a chain of 3-12 atoms. In some embodiments, L is a chain of 3-12 atoms, wherein each atom in the chain is independently selected from —$CR^6R^7$— or —O—. In some embodiments, L is a chain of 3-8 atoms, wherein each atom in the chain is independently selected from —$CR^6R^7$— or —O—. In some embodiments, L is an alkylene chain of 3-8 atoms. In some embodiments, L is a chain of 3-6 atoms, wherein each atom in the chain is independently selected from —$CR^6R^7$— or —O—. In some embodiments, Lis an alkylene chance of 3-6 atoms. In some embodiments, L is an alkylene chain of 3-8 atoms containing a single double bond. In some embodiments, L is an alkylene chain of 3-8 atoms optionally containing a single double bond.

In some embodiments, each $R^6$ and $R^7$ is independently hydrogen, $C_1$-$C_6$ alkyl, cycloalkyl, or heterocycloalkyl; wherein the alkyl, cycloalkyl, and heterocycloalkyl, are independently optionally substituted with one or more $R^{60}$; or adjacent $R^6$ are taken together to form a double bond. In some embodiments, each $R^6$ and $R^7$ is independently hydrogen, $C_1$-$C_6$ alkyl, or cycloalkyl; or adjacent $R^6$ are taken together to form a double bond. In some embodiments, each $R^6$ and $R^7$ is independently hydrogen or adjacent $R^6$ are taken together to form a double bond.

In some embodiments, L is selected from (substituted or unsubstituted)

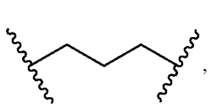, 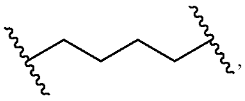,

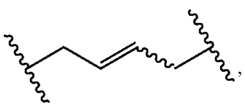, 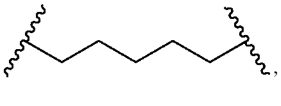,

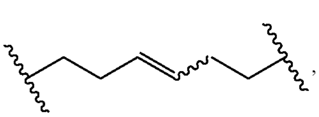,

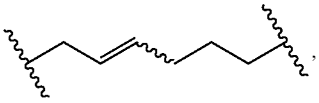,

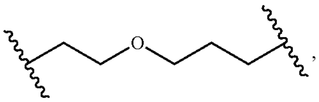,

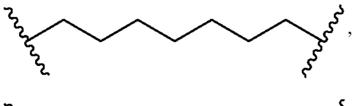,

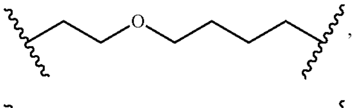,

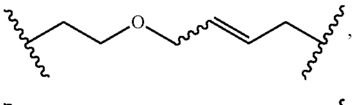,

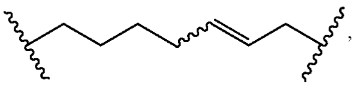,

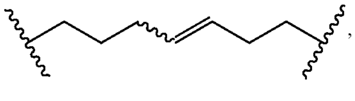, and

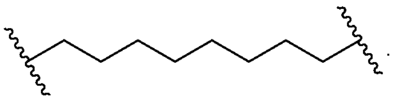.

In specific embodiments, provided herein are compounds of Formula (I) having a structure of Formula (Ia):

Formula (Ia)

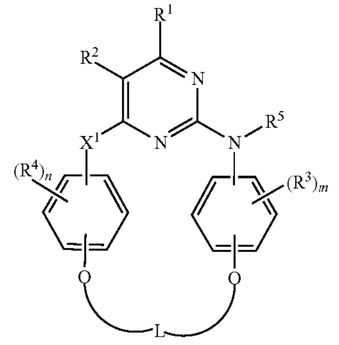

In some embodiments, $R^1$ is hydrogen, halogen, or haloalkyl (e.g., —$CF_3$);

$R^2$ is hydrogen, halogen, —CN, —$NO_2$, —C(═O)R, —C(═O)C(═O)R, substituted or unsubstituted alkyl, or substituted or unsubstituted heteroalkyl;

$X^1$ is —O—, —$NR^5$—, or —S—;

each $R^3$ and $R^4$ is independently halogen, —CN, —OR, —SR, —$NO_2$, —NRS(═O)$_2$R, —S(═O)$_2$NRR, —C(═O)R, —OC(═O)R, —C(═O)OR, —OC(═O)OR, —C(═O)NRR, —OC(═O)NRR, —NRC(═O)NRR, —NRS(═O)$_2$NRR, —NRC(═O)R, —NRC(═O)OR, substituted or unsubstituted alkyl, or substituted or unsubstituted heteroalkyl;

$R^5$ is substituted or unsubstituted alkyl, or substituted or unsubstituted heteroalkyl;

L is a chain $C_3$-$C_8$ substituted or unsubstituted alkylene;

each R is independently hydrogen, substituted or unsubstituted alkyl, substituted or unsubstituted heteroalkyl, substituted or unsubstituted aryl, or substituted or unsubstituted heteroaryl;

n is an integer from 0-4; and m is an integer from 0-4, or pharmaceutically acceptable salt thereof.

In certain embodiments, $R^1$ is hydrogen or halogen.

In some embodiments, $R^2$ is hydrogen, halogen, —$CF_3$, —CN, —$NO_2$, —C(═O)($C_1$-$C_6$ alkyl), —C(═O)C(═O)($C_1$-$C_6$ alkyl), —$C_1$-$C_6$ alkyl, or cycloalkyl; wherein the alkyl or cycloalkyl is independently optionally substituted with one or more $R^{20}$. In some embodiments, each $R^{20}$ is independently —OH, —O($C_1$-$C_6$ alkyl), $C_1$-$C_6$ haloalkyl, $C_1$-$C_6$ hydroxyalkyl, or $C_1$-$C_6$ alkyl.

In certain embodiments, $X^1$ is —O—, —$NR^5$—, or —S—. In some embodiments, $R^5$ is $C_1$-$C_6$ alkyl or $C_1$-$C_6$ haloalkyl.

In certain embodiments, each $R^3$ is independently halogen, —CN, —$OR^{31}$, —$SR^{31}$, —$NO_2$, —S(═O)$_2NR^{33}R^{34}$, —C(═O)$R^{32}$, —OC(═O)$R^{32}$, —C(═O)$OR^{31}$, —OC(═O)$OR^{31}$, —C(═O)$NR^{33}R^{34}$, —OC(═O)$NR^{33}R^{34}$, —$NR^{31}$C(═O)$NR^{33}R^{34}$, —$NR^{31}$S(═O)$_2NR^{33}R^{34}$, —$NR^{31}$C(═O)$R^{32}$, —$NR^{31}$C(═O)$OR^{31}$, $C_1$-$C_6$ alkyl, or cycloalkyl.

In some embodiments, each $R^4$ is independently halogen, —CN, —$OR^{41}$, —$SR^{41}$, —$NO_2$, —S(═O)$_2NR^{43}R^{44}$, —C(═O)$R^{42}$, —OC(═O)$R^{42}$, —C(═O)$OR^{41}$, —OC(═O)$OR^{41}$, —C(═O)$NR^{43}R^{44}$, —OC(═O)$NR^{43}R^{44}$, —$NR^{41}$C(═O)$NR^{43}R^{44}$, —$NR^{41}$S(═O)$_2NR^{43}R^{44}$, —$NR^{41}$C(═O)$R^{42}$, —$NR^{41}$C(═O)$OR^{41}$, $C_1$-$C_6$ alkyl, or cycloalkyl.

In certain embodiments, each $R^{31}$, $R^{32}$, $R^{33}$, $R^{34}$, $R^{41}$, $R^{42}$, $R^{43}$, and $R^{44}$ is independently hydrogen, $C_1$-$C_6$ haloalkyl, $C_1$-$C_6$ hydroxyalkyl, or $C_1$-$C_6$ alkyl.

In some embodiments, L is a $C_3$-$C_8$ alkylene chain.

In certain embodiments, m is 0, 1, or 2. In some embodiments, n is 0, 1 or 2.

In specific embodiments, the compound is a pharmaceutically acceptable salt of a compound of Formula (Ia).

In some embodiments, is a compound, pharmaceutically acceptably salt, solvate, or stereoisomer thereof, wherein the compound is selected from:

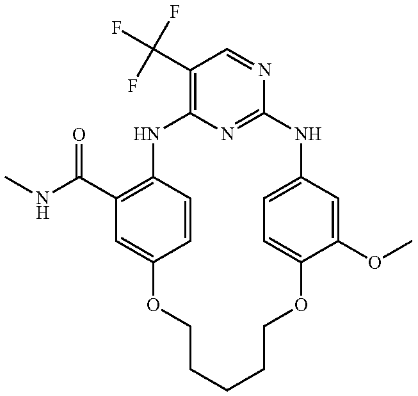
,

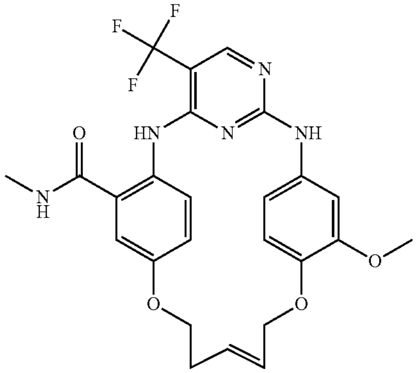
,

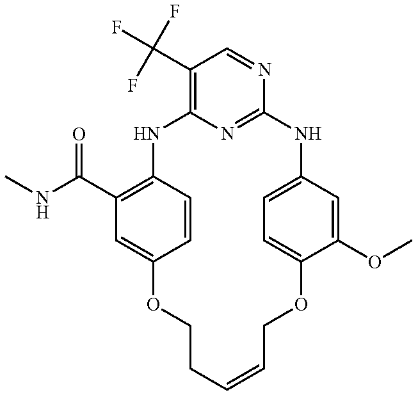
,

-continued

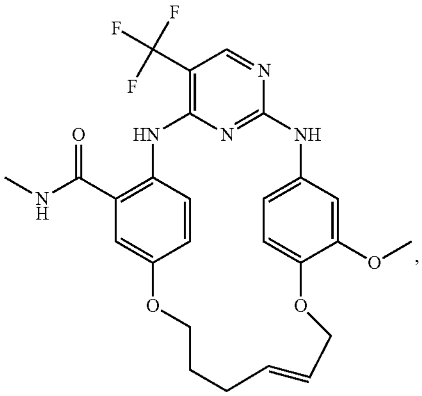
,

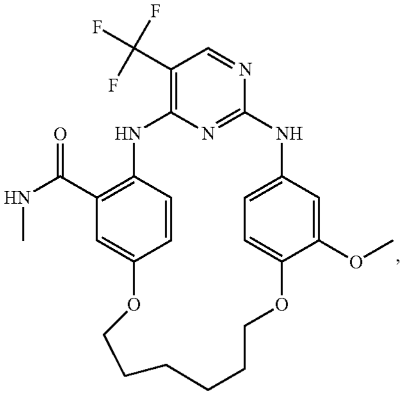
,

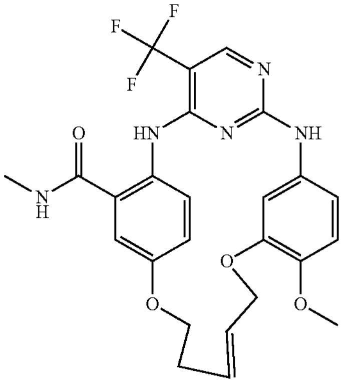
,

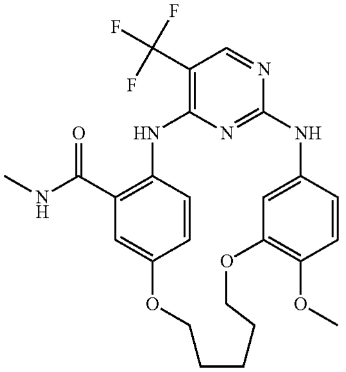
,

-continued
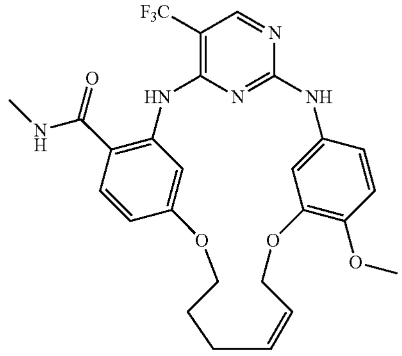
,
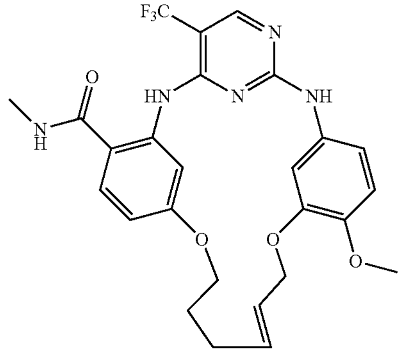
,
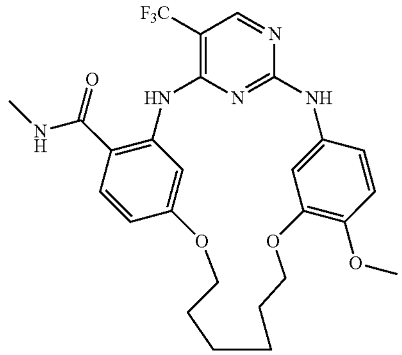
,
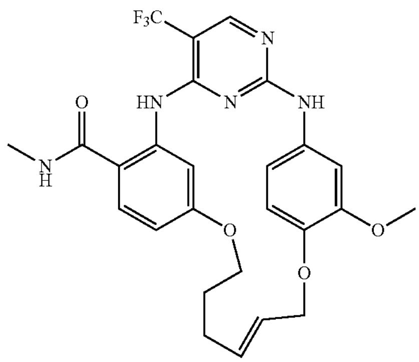
,
-continued
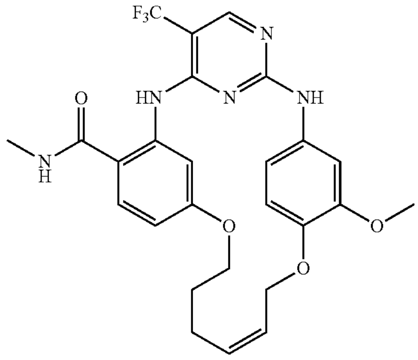
,
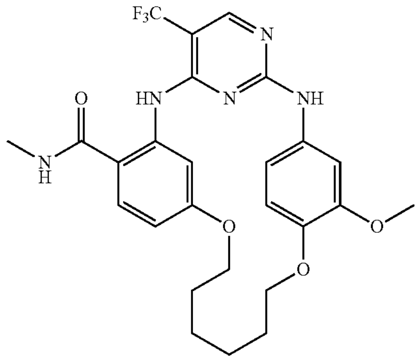
,
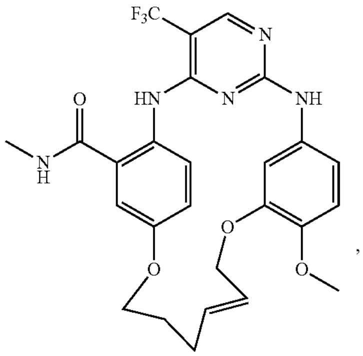
,
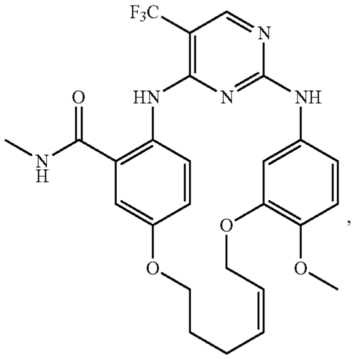
, -continued

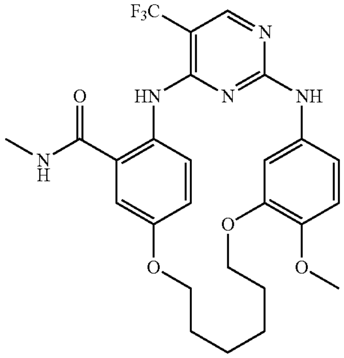

,

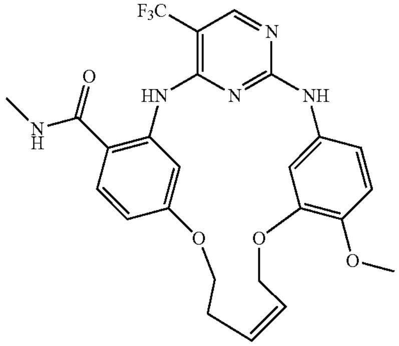

,

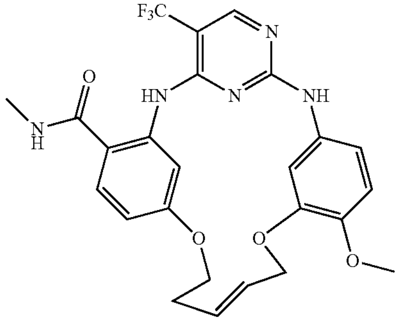

,

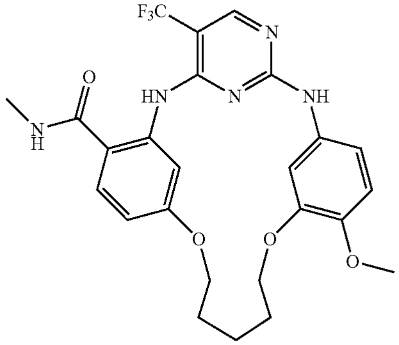

,

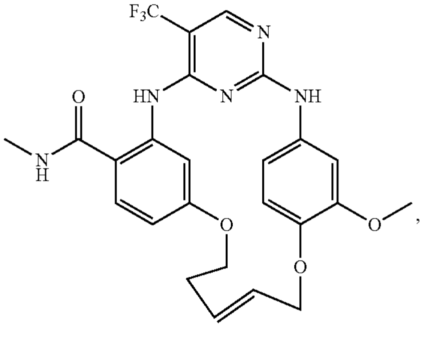

, and

-continued

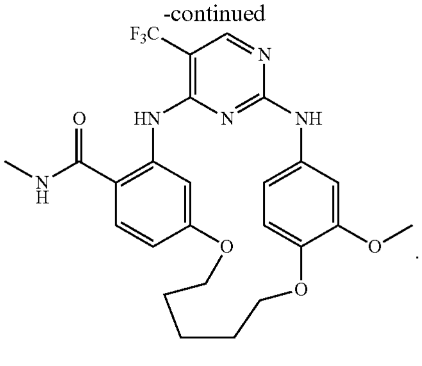

.

Any combination of the groups described above for the various variables is contemplated herein. Throughout the specification, groups and substituents thereof are chosen by one skilled in the field to provide stable moieties and compounds.

Illustrative compounds are shown in Table 1 (along with their respective $IC_{50}$ values for ULK1 inhibition assays).

$IC_{50}$s measured by ADP-Glo assay are represented nM, with A representing $IC_{50}$<20 nM, B representing $IC_{50}$>20 nM. NT indicates the compound was not tested. ULK1 inhibition assays were performed in a 5 uL reaction volume containing 2 ug/mL recombinant human ULK1 protein (1-649, SignalChem #U01-11G) and 80 ug/mL myelin basic protein (MBP, Sigma-Aldrich #M1891) in the presence of 25 uM ATP (Sigma-Aldrich A7699). ULK 1 inhibition was assessed after one hour. Compounds were tested in triplicate in a 16-dose $IC_{50}$ mode with 3-fold serial dilution and a starting dose of 30 uM. Staurosporine, a non-selective protein kinase inhibitor, was used in the assay as a positive control. Three separate experiments were carried out.

$IC_{50}$s were also measured by ULK1 NanoBRET assay according to the following protocol: Human embryonic kidney cells (HEK293T) were transfected with NanoLuc®-ULK1 Fusion Vector (Promega #NV2211) using jetPRIME transfection reagent (Polyplus Transfection #114-15). Following 24 h, cells were trypsinized and resuspended in Opti-MEM® I (1×), Reduced Serum Medium (Gibco, #11058-021). Approximately, 7,000 cells per well (in 34 μL total volume) were replated into non-binding surface 384 well plates. Complete NanoBRET 20× Tracer K-5 reagent was prepared according to the manufacturer's directions and 2 μL were added to each well of the 384 plate (assay plate). The assay plate was mixed on an orbital shaker for 15 seconds at 700 rpm. Compounds were serially diluted at 200× final concentration in 1000 DMSO, then diluted to 10× final concentration in assay media (Opti-MEM® I, Reduced Serum Medium). Next, 4 μL 10× test compounds were added to each well of the assay plate, followed by mixing at 700 rpm for 15 seconds. The assay plate was incubated for 2 h in a 37 C incubator with 500 CO2 and then equilibrated to RT for 15 min. The 3× Complete Substrate plus Inhibitor Solution was prepared according to the manufacturer's directions with a concentration of Extracellular NanoLuc® Inhibitor of 60 μM to be used at a working concentration of 20 μM. The 3× Complete Substrate plus Inhibitor Solution was mixed and 20 μL per well was added to the assay plate and incubated at RT for 2-3 min. Donor emission wavelength (450 nm) and acceptor emission wavelength (610 nm) were measured using an assay compatible luminometer (see manufacturer's specifications).

TABLE 1
| Compound Number | Structure | ULK1 IC50 (nM) ADP-Glo (A < 20 nM, B > 20 nM) | ULK1 IC50 (nM) nanoBRET (A < 1000 nM, B > 1000 nM) |
|---|---|---|---|
| 1 | 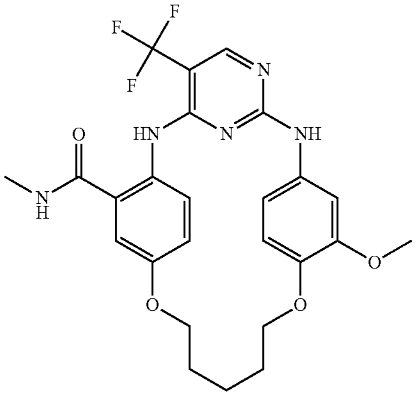 | A | B |
| 2 | 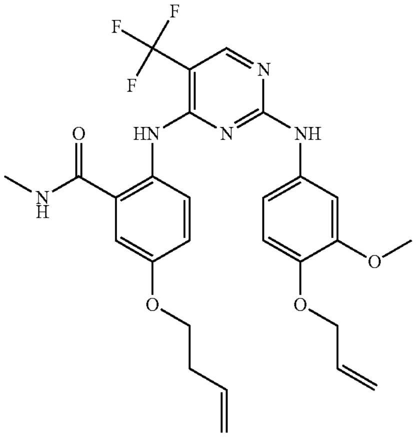 | B | NT |
| 3 | 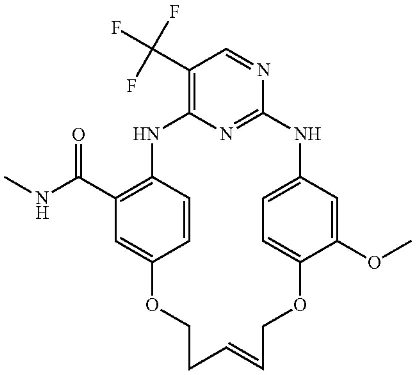 | B | A |

TABLE 1-continued
| Compound Number | Structure | ULK1 IC50 (nM) ADP-Glo (A < 20 nM, B > 20 nM) | ULK1 IC50 (nM) nanoBRET (A < 1000 nM, B > 1000 nM) |
|---|---|---|---|
| 4 | 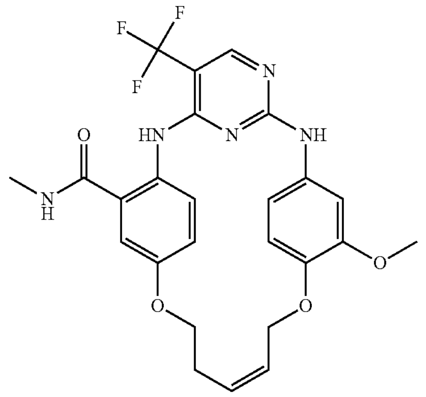 | B | A |
| 5 | 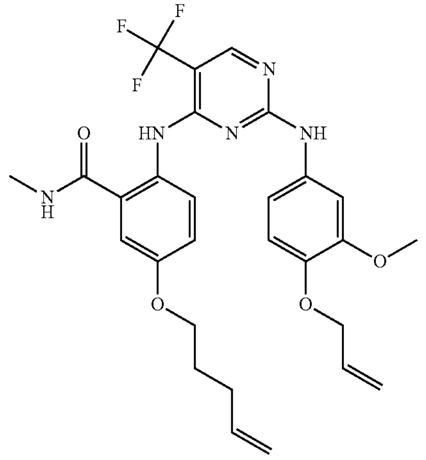 | B | B |
| 6 | 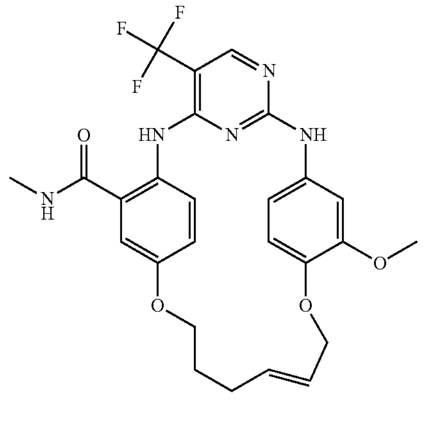 | A | A |

TABLE 1-continued
| Compound Number | Structure | ULK1 IC50 (nM) ADP-Glo (A < 20 nM, B > 20 nM) | ULK1 IC50 (nM) nanoBRET (A < 1000 nM, B > 1000 nM) |
| --- | --- | --- | --- |
| 7 | 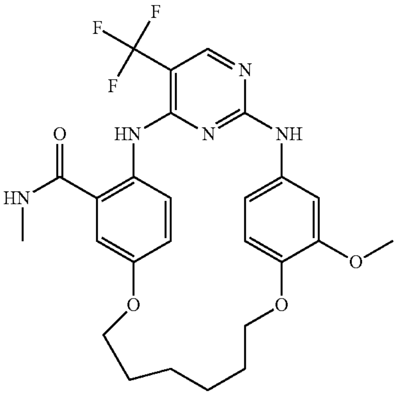 [SMILES: CNC(=O)c1cc2ccc1Nc1nc(ncc1C(F)(F)F)Nc1ccc(c(OC)c1)OCCCCCCO2] | A | NT |
| 8 | 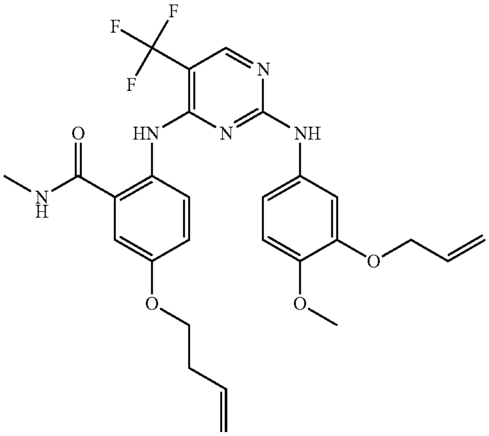 [SMILES: C=CCCOc1ccc(Nc2nc(Nc3ccc(OC)c(OCC=C)c3)ncc2C(F)(F)F)c(C(=O)NC)c1] | A | NT |
| 9 | 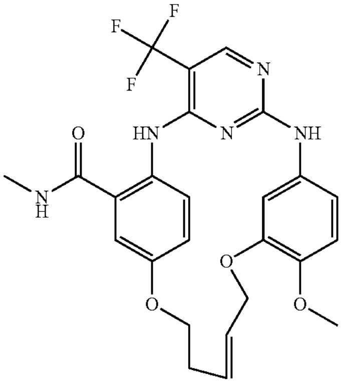 | A | A |

TABLE 1-continued
| Compound Number | Structure | ULK1 IC50 (nM) ADP-Glo (A < 20 nM, B > 20 nM) | ULK1 IC50 (nM) nanoBRET (A < 1000 nM, B > 1000 nM) |
|---|---|---|---|
| 10 | 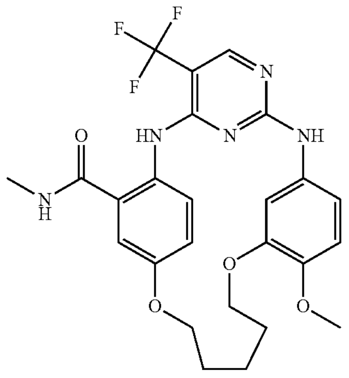 | A | B |
| 11 | 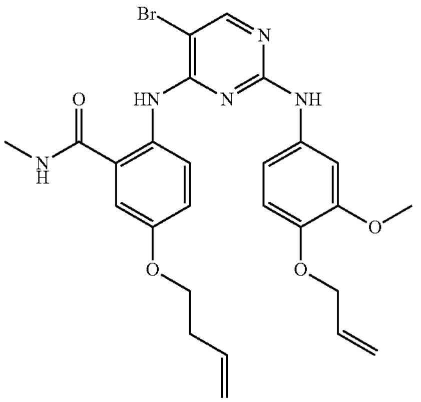 | B | NT |
| 12 | 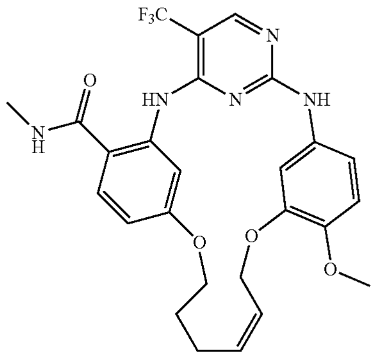 | B | B |
| 13 | 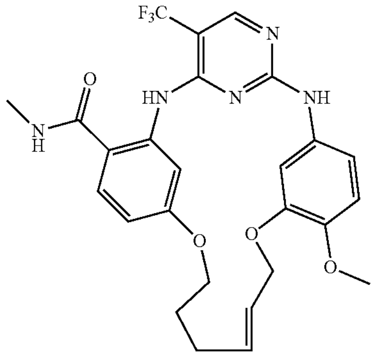 | B | B |

TABLE 1-continued
| Compound Number | Structure | ULK1 IC50 (nM) ADP-Glo (A < 20 nM, B > 20 nM) | ULK1 IC50 (nM) nanoBRET (A < 1000 nM, B > 1000 nM) |
|---|---|---|---|
| 14 | 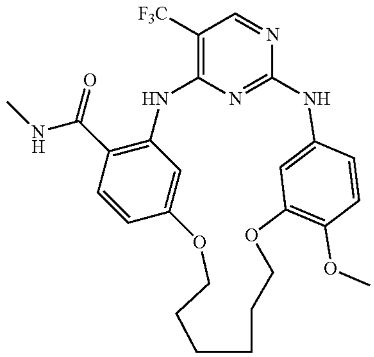 | B | B |
| 15 | 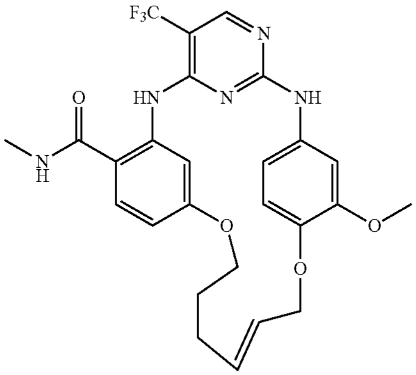 | B | B |
| 16 | 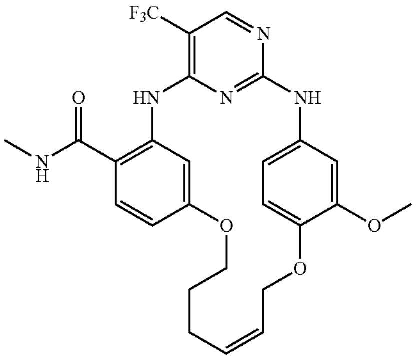 | B | B |
| 17 | 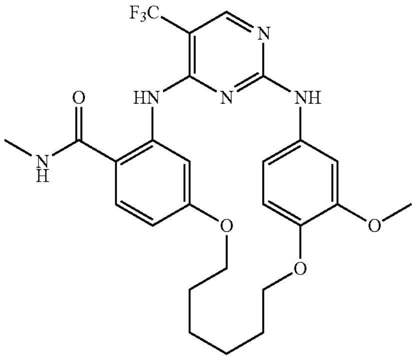 | B | B |

TABLE 1-continued
| Compound Number | Structure | ULK1 IC50 (nM) ADP-Glo (A < 20 nM, B > 20 nM) | ULK1 IC50 (nM) nanoBRET (A < 1000 nM, B > 1000 nM) |
|---|---|---|---|
| 18 | 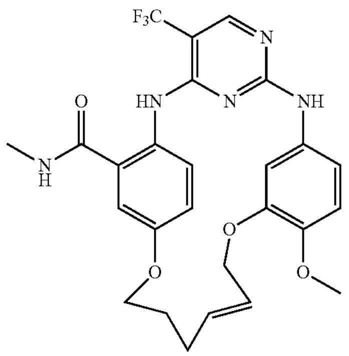 | A | B |
| 19 | 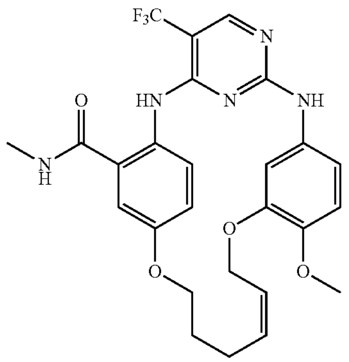 | A | A |
| 20 | 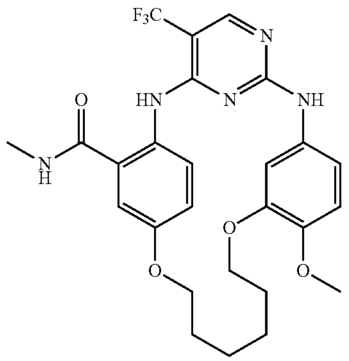 | A | B |
| 21 | 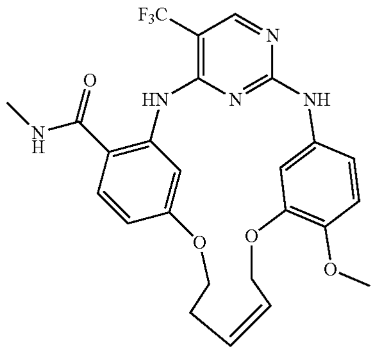 | B | B |

TABLE 1-continued

| Compound Number | Structure | ULK1 IC50 (nM) ADP-Glo (A < 20 nM, B > 20 nM) | ULK1 IC50 (nM) nanoBRET (A < 1000 nM, B > 1000 nM) |
|---|---|---|---|
| 22 | 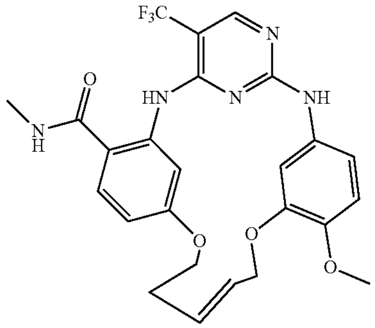 | B | B |
| 23 | 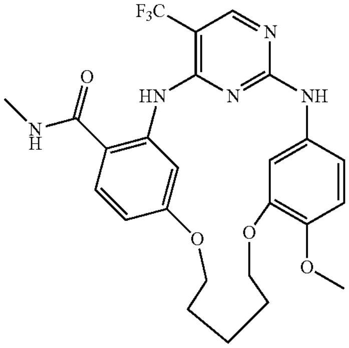 | B | B |
| 24 | 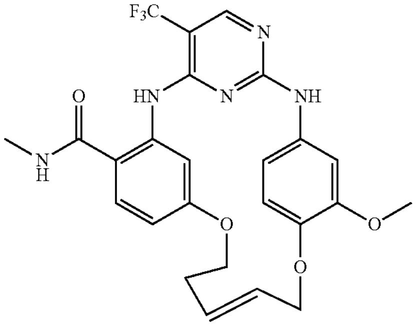 | B | B |
| 25 | 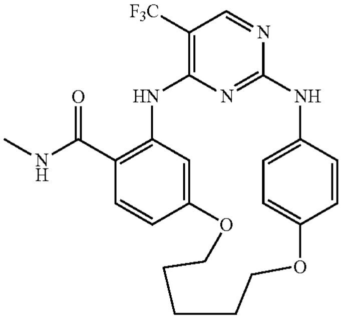 [SMILES: CNC(=O)c1ccc2cc1Nc1nc(ncc1C(F)(F)F)Nc1ccc(cc1)OCCCCCO2] | B | B |

The invention provides salts of any one of the compounds described herein. Pharmaceutically-acceptable salts include, for example, acid-addition salts and base-addition salts. In some embodiments, the acid that is added to the compound to form an acid-addition salt is an organic acid or an inorganic acid. In some embodiments, a base that is added to the compound to form a base-addition salt is an organic base or an inorganic base. In some embodiments, a pharmaceutically-acceptable salt is a metal salt.

In some embodiments, metal salts arise from the addition of an inorganic base to a compound of the invention. The inorganic base consists of a metal cation paired with a basic counterion, such as, for example, hydroxide, carbonate, bicarbonate, or phosphate. In some embodiments, the metal is an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

In some embodiments, ammonium salts arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, an imidazole salt, or a pyrazine salt.

In some embodiments, acid addition salts arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccharate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

The compounds described herein may in some cases exist as diastereomers, enantiomers, or other stereoisomeric forms. The compounds and salts presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

According to another embodiment, the present disclosure provides methods of producing the above-defined compounds. The compounds may be synthesized using any suitable techniques. Advantageously, these compounds are conveniently synthesized from readily available starting materials. Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).). In general, synthesis and measurements of ULK1 inhibitory activity of the compounds described herein was performed using method analogous to those previously described in PCT International Application No. PCT/US2015/046777 which is hereby incorporated by reference in its entirety.

Pharmaceutical Formulations

The compounds of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. In some embodiments, this combination therapy is sequential therapy where the patient is treated first with one drug and then the other or the two drugs are given simultaneously. In some embodiments, these are administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional agents. In some embodiments, the compounds are administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention may be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. In some embodiments, the compounds are administered alone or mixed with a pharmaceutically acceptable carrier. In some embodiments, this carrier is a solid or liquid, and the type of carrier is generally chosen based on the type of administration being used. In some embodiments, the active agent is co-administered in the form of a tablet or capsule, liposome, as an agglomerated powder or in a liquid form. Examples of suitable solid carriers include lactose, sucrose, gelatin and agar. Capsule or tablets are easily formulated and made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Aspects of the invention include articles of manufacture, or kits, comprising the active agents described herein, and formulations thereof, as well as instructions for use. An article of manufacture, or kit, can further contain at least one additional reagent, e.g., a chemotherapeutic drug, etc. Articles of manufacture and kits typically include a label indicating the intended use of their contents. The term “label” as used herein includes any writing, or recorded material supplied on or with a kit, or which otherwise accompanies a kit.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington’s Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

The compounds used in the method of the present invention may also be administered in the form of liposome delivery systems, such as small unilamellar vesicles, large unilamallar vesicles, and multilamellar vesicles. Liposomes may be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

Methods of the Disclosure

In some instances, ULK inhibitors are used and/or useful in the treatment of cancer and/or ULK mediated disorders. Surprisingly, in certain instances, ULK inhibitors are efficacious as a monotherapy. In some instances, the ULK inhibitor inhibits ULK1. In some instances, the ULK inhibitor is a ULK1 specific inhibitor. In some instances, the ULK inhibitor inhibits both ULK1 and ULK2. In other instances, it is also surprising that ULK inhibitors are used/useful in augmenting or improving standard of care therapies.

Monotherapy

In one aspect, provided herein, is a method of treating a disease or disorder with a ULK inhibitor. In various embodiments, the ULK inhibitor is administered alone to treat a disease or disorder. In some embodiments, the method comprises administering to a subject in need thereof a therapeutically effective amount of a ULK inhibitor. In some instances, the ULK inhibitor inhibits ULK11. In some instances, the ULK inhibitor is a ULK1 specific inhibitor. In some instances, the ULK inhibitor inhibits both ULK1 and ULK2.

In some embodiments, the ULK inhibitor is administered as a monotherapy. In some embodiments, the ULK inhibitor is the sole therapeutic agent administered to the patient for the treatment of the disease or disorder. In some embodiments, the ULK inhibitor is the sole anti-cancer agent administered to the patient. In some embodiments, the ULK inhibitor is administered as a monotherapy with additional inactive ingredients as part of a pharmaceutical formulation. In some instances, the ULK inhibitor inhibits ULK1. In some instances, the ULK inhibitor is a ULK1 specific inhibitor. In some instances, the ULK inhibitor inhibits both ULK1 and ULK2.

In some embodiments, the disease or disorder is characterized by abnormal autophagy. In some embodiments, the abnormal autophagy is therapeutically induced. In some embodiments, the disease or disorder is refractory. In some embodiments, the disease or disorder is refractory to treatment with a non-ULK inhibitor therapeutic agent. In embodiments, the disease or disorder is resistant to treatment with a non-ULK inhibitor therapeutic agent.

In some embodiments, the disease or disorder treated with a ULK inhibitor as a monotherapy is cancer. In some instances, the ULK inhibitor inhibits ULK11. In some instances, the ULK inhibitor is a ULK1 specific inhibitor. In some instances, the ULK inhibitor inhibits both ULK1 and ULK2. In some embodiments, the cancer is lung cancer. In specific embodiments, the lung cancer is NSCLC. In some embodiments, the cancer is an advanced stage NSCLC. In some embodiments, the cancer comprises a tumor. In some embodiments, the NSCLC comprises a tumor. In some embodiments, the NSCLC is characterized by abnormal autophagy. In some embodiments, the lung cancer is refractory. In some embodiments, the lung cancer is refractory to treatment with carboplatin. In some embodiments, the NSCLC is refractory. In some embodiments, the NSCLC is refractory to treatment with carboplatin. In some embodiments, the lung cancer is characterized by cytostasis.

In some embodiments, the cancer is pancreatic cancer. In some embodiments, the pancreatic cancer comprises a tumor. In some embodiments, the pancreatic cancer is characterized by abnormal autophagy. In some embodiments, the pancreatic cancer is refractory. In some embodiments, the pancreatic cancer is characterized by cytostasis. In some embodiments, the pancreatic cancer is PDAC.

In some embodiments, the cancer is breast cancer. In some embodiments, the breast cancer comprises a tumor. In some embodiments, the breast cancer is characterized by abnormal autophagy. In some embodiments, the breast cancer is refractory. In some embodiments, the breast cancer is characterized by cytostasis. In some embodiments, the breast cancer is TNBC.

In some embodiments, the disease or disorder treated with a ULK inhibitor as a monotherapy is LAM. In some embodiments, the disease or disorder treated with a ULK inhibitor as a monotherapy is TSC. In some instances, the ULK inhibitor inhibits ULK11. In some instances, the ULK inhibitor is a ULK1 specific inhibitor. In some instances, the ULK inhibitor inhibits both ULK1 and ULK2.

In some embodiments, administering a ULK inhibitor slows progression of the disease or disorder. In some embodiments, administering a ULK inhibitor slows progression of the disease or disorder by at least 10%, at least 20%, at least 30%, at least 40%, at least 50%, at least 60%, at least 70%, at least 80%, at least 90%, or at least 95%. In some embodiments, progression is measured by tumor growth. In some embodiments, administering a ULK inhibitor arrests cancer cell growth. In some embodiments, administering a ULK inhibitor reduces tumor volume. In some instances, the ULK inhibitor is a ULK1 specific inhibitor. In some instances, the ULK inhibitor inhibits both ULK1 and ULK2.

In some embodiments, the method of treatment comprises decreasing phosphorylation of ATG13 in the subject. In some embodiments, the method comprises degrading ATG13 in diseased tissue of the subject. In some embodiments, administering the ULK inhibitor degrades ATG13.

In some embodiments, the subject comprises a mutation in at least one of KRAS, PTEN, TSC1, TSC2, PIk3CA, P53, STK11 (a.k.a. LKB1), KEAP1, NRF2, ALK4, GNAS, or EGFR. In some embodiments, the subject comprises a mutation in at least one of SMAD4, p16/CDKM2A, or BRCA2.

Combination Therapy

The compounds, or the pharmaceutically acceptable salts thereof, provided herein may be administered in combination with one or more therapeutic agents.

Also described herein are combination therapies. In some instances, the combination therapies of the present invention comprise a ULK inhibitor and an additional therapeutic agent. In some instances, the ULK inhibitor inhibits ULK1. In some instances, the ULK inhibitor is a ULK1 specific inhibitor. In some instances, the ULK inhibitor inhibits both ULK1 and ULK2. In some embodiments, there is an additional therapeutic benefit when compared to treatment with the additional therapeutic agent alone. In some instances, the combination of the ULK inhibitor and the additional therapeutic agent shut down pathways of autophagy. This allows for enhanced cell death in diseased tissue, as the diseased cells will not be able to rely on autophagic processes for survival once the pathway is shut off with a ULK inhibitor. In some embodiments, the addition of a ULK inhibitor allows for successful treatment of a disease that is otherwise refractory to treatment of the additional therapeutic agent by itself. In some embodiments, the addition of the ULK inhibitor enhances the efficacy of the additional therapeutic agent. In some embodiments, the addition of the ULK inhibitor has a synergistic effect with the additional therapeutic agent. In some embodiments, the additional therapeutic agent is a standard of care therapy.

In one aspect, provided herein, is a method of treating a disease or disorder with a ULK inhibitor and an additional therapeutic agent. In some embodiments, the method comprises administering to a subject in need thereof a therapeutically effective amount of a ULK inhibitor. In some embodiments, the method comprises administering to a subject in need thereof a therapeutically effective amount of a ULK inhibitor and a therapeutically effective amount of an additional therapeutic agent. In some instances, the ULK inhibitor inhibits ULK1. In some instances, the ULK inhibitor is a ULK1 specific inhibitor. In some instances, the ULK inhibitor inhibits both ULK1 and ULK2.

In some embodiments, the disease or disorder is LAM. In some embodiments, the disease or disorder is TSC.

In some embodiments, the disease or disorder is cancer. In some embodiments, the disease or disorder is refractory cancer. In some embodiments, the cancer comprises a tumor. In some embodiments, the cancer is refractory to treatment with carboplatin. In some embodiments, the cancer is refractory to trametinib. In some embodiments, the cancer is refractory to an MEK inhibitor. In some embodiments, cancer is pancreatic cancer. In some embodiments, the cancer is lung cancer. In some embodiments, the lung cancer is NSCLC. In some embodiments, the cancer is refractory to an mTOR inhibitor. In some embodiments, the cancer is refractory to rapamycin. In some embodiments, the cancer is refractory to treatment with a rapamycin analog.

In some embodiments, the cancer is pancreatic cancer and the additional therapeutic agent is trametinb. In some embodiments, the cancer is pancreatic cancer and the additional therapeutic agent is an MEK inhibitor. In some embodiments, the MEK inhibitor is trametinib, cobimetinib, binimetinib, or selumetinib. In some embodiments, the cancer is pancreatic cancer and the additional therapeutic agent is gemcitabine. In some embodiments, the cancer is pancreatic cancer and the additional therapeutic agent is a nucleoside analog. In some embodiments, the cancer is pancreatic cancer and the additional therapeutic agent is gemcitabine, everolimus, erlotinib, or sunitinib. In some embodiments, the additional therapeutic agent is FOLFIRINOX (5-fluorouracil, leucovorin, irinotecan, and oxaliplatin), gemcitabine, or gemcitabine/abraxane. In some embodiments, the additional therapeutic agent is capeditabine, leucovorin, nab-pacitaxel, nanoliposomal irinotecan, gemcitabine/nab-pacitaxel, pembrolizumab, or cisplatin. In some embodiments, the additional therapeutic agent is capeditabine, leucovorin, nab-pacitaxel, nanoliposomal irinotecan, gemcitabine/nab-pacitaxel, pembrolizumab, or cisplatin. In some embodiments, the pancreatic cancer is PDAC. In some embodiments, the subject with pancreatic cancer comprises a mutation in at least one of SMAD4, p16/CDKM2A, or BRCA2. In some embodiments, the cancer is pancreatic cancer and the additional therapeutic agent is a standard of care therapy.

In some embodiments, the cancer is breast cancer. In some embodiments, the cancer is breast cancer and the additional therapeutic agent is a standard of care therapy. In some embodiments, the cancer is breast cancer and the additional therapeutic agent is anastrozole, exemestane, letrozole, or tamoxifen. In some embodiments, the cancer is breast cancer and the additional therapeutic agent is a PARP inhibitor. In some embodiments, the PARP inhibitor is olaparib, rucaparib, niraparib, or talazoparib. In some embodiments, the breast cancer is triple negative breast cancer (TNBC).

In some embodiments, the cancer is lung cancer and the additional therapeutic agent is carboplatin. In some embodiments, the cancer is lung cancer and the additional therapeutic agent is a carboplatin analog. In some embodiments, the cancer is NSCLC and the additional therapeutic agent is carboplatin. In some embodiments, the cancer is NSCLC and the additional therapeutic agent is a carboplatin analog. In some embodiments, the carboplatin analog is cisplatin or dicycloplatin. In some embodiments, the cancer is lung cancer and the additional therapeutic agent is erlotinib, gefitinib, osimertinib, or crizotinib. In some embodiments, the cancer is NSCLC and the additional therapeutic agent is erlotinib, gefitinib, osimertinib, or crizotinib. In some embodiments, the cancer is lung cancer and the additional therapeutic agent is pemetrexed, docetaxol, or pembroluzimab. In some embodiments, the cancer is NSCLC and the additional therapeutic agent is pemetrexed, docetaxol, or pembroluzimab. In some embodiments, the cancer is lung cancer and the additional therapeutic agent is gemcitabine, bortexomib, trastuzumab, vinorelbine, doxorubicin, irinotecan, temsirolimus, sunitinib, nivolumab, or bevacizumab. In some embodiments, the cancer is lung cancer and the additional therapeutic agent is carboplatin/gemcitabine, carboplatin/paclitaxel/cetuximua, cisplatin/pemetrexed, cisplatin/docetaxel, cisplatin/docetaxel/bevacizumab, everolimus/nab-paclitaxel, or tremelimumab/durvalumab. In some embodiments, the cancer is NSCLC and the additional therapeutic agent is gemcitabine, bortexomib, trastuzumab, vinorelbine, doxorubicin, irinotecan, temsirolimus, sunitinib, nivolumab, or bevacizumab. In some embodiments, the cancer is NSCLC and the additional therapeutic agent is carboplatin/gemcitabine, carboplatin/paclitaxel/cetuximua, cisplatin/pemetrexed, cisplatin/docetaxel, cisplatin/docetaxel/bevacizumab, everolimus/nab-pacitaxel, or tremelimumab/durvalumab. In some embodiments, the subject with lung cancer comprises a mutation in KRAS, PTEN, TSC1, TSC2, PIk3CA, P53, STK11 (a.k.a. LKB1), KEAP1, NRF2, ALK4, GNAS or EGFR.

In some embodiments, the additional therapeutic agent is carboplatin. In some embodiments, the additional therapeutic agent is carboplatin or a carboplatin analog. In some embodiments, the carboplatin analog is cisplatin or dicycloplatin.

In some embodiments, the additional therapeutic agent is erlotinib, gefitinib, osimertinib, or crizotinib. In some embodiments, the additional therapeutic agent is pemetrexed, docetaxol, or pembroluzimab. In some embodiments, the additional therapeutic agent is carboplatin/gemcitabine, carboplatin/pacitaxel/cetuximua, cisplatin/pemetrexed, cisplatin/docetaxel, cisplatin/docetaxel/bevacizumab, everolimus/nab-pacitaxel, or tremelimumab/durvalumab.

In some embodiments, the additional therapeutic agent is anastrozole, exemestane, letrozole, or tamoxifen. In some embodiments, the additional therapeutic agent is a PARP inhibitor. In some embodiments, the PARP inhibitor is olaparib, rucaparib, niraparib, or talazoparib.

In some embodiments, the additional therapeutic agent is gemcitabine, everolimus, erlotinib, or sunitinib. In some embodiments, the additional therapeutic agent is a nucleoside analog. In some embodiments, is FOLFIRINOX, gemcitabine, or gemcitabine/abraxane. In some embodiments, the additional therapeutic agent is capeditabine, leucovorin, nab-pacitaxel, nanoliposomal irinotecan, gemcitabine/nab-paclitaxel, pembrolizumab, or cisplatin.

In some embodiments, the additional therapeutic agent is an MEK inhibitor. In some embodiments, the additional therapeutic agent is trametinib. In some embodiments, the MEK inhibitor is trametinib, cobimetinib, binimetinib, or selumetinib.

In some embodiments, the additional therapeutic agent is gemcitabine. In some embodiments, the additional therapeutic agent is a nucleoside analog.

In some embodiments, the additional therapeutic agent is an mTOR inhibitor. In some embodiments, the additional therapeutic agent is rapamycin. In some embodiments, mTOR inhibitor is rapamycin, sirolimus, temsirolimus, everolimus, ridaforolimus, NVPBEZ235, BGT226, XL765, GDC0980, SF1 126, PK1587, PF04691502, GSK2126458, INK128, TORKiCC223, OSI027, AZD8055, AZD2014, and Palomid 529, metformin, or AICAR (5-amino-1-P-D-ribofuranosyl-imidazole-4-carboxamide). In some embodiments, the additional therapeutic agent is a rapamycin analog.

In some embodiments, the disease or disorder is lymphoangiomyoleiomatosis and the additional therapeutic agent is an mTOR inhibitor. In some embodiments, the disease or disorder is tuberous sclerosis complex and the additional therapeutic agent is an mTOR inhibitor.

In some embodiments, the additional therapeutic agent was previously administered to the subject without a ULK inhibitor. In some embodiments, the additional therapeutic agent induces a cytostatic response. In some embodiments, the additional therapeutic agent induces a cytostatic response when administered without a ULK inhibitor. In some embodiments, the additional therapeutic agent induces a cytostatic response in disease tissue. In some embodiments, the additional therapeutic agent induces a cytostatic response in the diseased tissue when the additional therapeutic agent was administered without a ULK inhibitor. In some instances, the ULK inhibitor inhibits ULK1. In some instances, the ULK inhibitor is a ULK1 specific inhibitor. In some instances, the ULK inhibitor inhibits both ULK1 and ULK2.

In some embodiments, the subject is treated with the additional therapeutic agent prior to treatment with the ULK inhibitor. In some embodiments, treatment with the additional therapeutic agent is ceased prior to administration of the ULK inhibitor. In some embodiments, treatment with the additional therapeutic agent produces a cytostatic response in diseased tissue.

In some embodiments, the ULK inhibitor and the additional therapeutic agent are administered concomitantly. In some embodiments, the ULK inhibitor and the additional therapeutic agent are administered together at the start of treatment. In some instances, the ULK inhibitor inhibits ULK11. In some instances, the ULK inhibitor is a ULK1 specific inhibitor. In some instances, the ULK inhibitor inhibits both ULK1 and ULK2.

In some embodiments, the disease or disorder is characterized by abnormal autophagy. In some embodiments, the abnormal autophagy is therapeutically induced. In some embodiments, the disease or disorder is refractory. In some embodiments, the disease or disorder is refractory to treatment with an additional therapeutic agent. In embodiments, the disease or disorder is resistant to treatment with an additional therapeutic agent.

In some embodiments, administering a ULK inhibitor slows progression of the disease or disorder. In some embodiments, administering a ULK inhibitor slows progression of the disease or disorder when compared to administration of the additional therapeutic agent with the ULK inhibitor. In some embodiments, administering a ULK inhibitor slows progression of the disease or disorder by at least 10%, at least 20%, at least 30%, at least 40%, at least 50%, at least 60%, at least 70%, at least 80%, at least 90%, or at least 95%. In some embodiments, administering a ULK slows the progression of the disease or disorder by at least 10%, at least 20%, at least 30%, at least 40%, at least 50%, at least 60%, at least 70%, at least 80%, at least 90%, or at least 95% when compared to administration of the additional therapeutic agent without the ULK inhibitor. In some embodiments, progression of the disease or disorder comprises growth of a tumor. In some embodiments, progression is measured by tumor growth. In some embodiments, administering a ULK inhibitor arrests cancer cell growth. In some embodiments, administering a ULK inhibitor reduces tumor volume. In some instances, the ULK inhibitor inhibits ULK1l. In some instances, the ULK inhibitor is a ULK1 specific inhibitor. In some instances, the ULK inhibitor inhibits both ULK1 and ULK2.

In some embodiments, administering a ULK inhibitor enhances the efficacy of the additional therapeutic agent by at least 10%, at least 20%, at least 30%, at least 40%, at least 50%, at least 60%, at least 70%, at least 80%, at least 90%, or at least 95%. In some embodiments, administering a ULK inhibitor enhances the efficacy of the additional therapeutic agent by at least 10%, at least 20%, at least 30%, at least 40%, at least 50%, at least 60%, at least 70%, at least 80%, at least 90%, or at least 95% when compared to administration of the additional therapeutic agent with the ULK inhibitor. In some embodiments, the efficacy is measured by a change in the rate of tumor growth. In some embodiments, efficacy is measured by reduction of tumor volume. In some instances, the ULK inhibitor inhibits ULK1. In some instances, the ULK inhibitor is a ULK1 specific inhibitor. In some instances, the ULK inhibitor inhibits both ULK1 and ULK2.

In some embodiments, the method of treatment comprises decreasing phosphorylation of ATG13 in the subject. In some embodiments, the method comprises degrading ATG13 in diseased tissue of the subject. In some embodiments, administering a ULK inhibitor causes degradation of ATG13.

In some embodiments, the subject comprises a mutation in at least one of KRAS, PTEN, TSC1, TSC2, PIk3CA, P53, STK11 (a.k.a. LKB1), KEAP1, NRF2, ALK4, GNAS, or EGFR. In some embodiments, the subject comprises a mutation in at least one of SMAD4, p16/CDKM2A, or BRCA2.

Additional indications for which ULK1 inhibitors are useful are described in PCT International Application No. PCT/US2015/046777, which is hereby incorporated by reference in its entirety.

EXAMPLES

Chemical Synthesis

Reactions were performed in oven-dried glassware under a nitrogen atmosphere with magnetic stirring. All solvents and chemicals were purchased from commercial sources and used without further purification unless specified. Reactions conducted under microwave irradiation were performed in a CEM Discover microwave reactor using 10 mL reaction vessels. Reaction progress was monitored by reverse-phase HPLC and/or thin-layer chromatography (TLC). Chromatographic purification was carried out using pre-packed silica or C18 cartridges (from RediSep and Luknova) and eluted using an ISCO Companion system. Reverse phase purifications were conducted using water and acetonitrile or methanol doped with 0.1% formic acid. Purity and characterization of compounds was established by a combination of liquid chromatography-mass spectroscopy (LC-MS) and Nuclear Magnetic Resonance (NMR) analytical techniques. HPLC-MS analyses were performed on a Shimadzu 2010EV LCMS using the following conditions: Kromisil C18 column (reverse phase, 4.6 mm_50 mm); a linear gradient from 10% acetonitrile and 90% water to 95% acetonitrile and 5% water over 4.5 min; flow rate of 1 mL/min; UV photodiode array detection from 200 to 300 nm. Proton (1H) and Carbon (13C) NMR spectra were obtained on a Joel 400 spectrometer at 400 MHz and 101 MHz, respectively. Chemical shifts are reported in δ (ppm) and were internally referenced to deuterated solvent signals. The data for 1H-NMR are reported in terms of chemical shift (δ ppm), multiplicity, coupling constant (Hz), and proton integration. The data for 13C-NMR are reported in terms of chemical shift (δ ppm) and coupling constant (Hz).

Abbreviations used: mass spectrometry (MS), palladium on carbon (Pd—C), acetonitrile (MeCN), dichloromethane (DCM), diethyl ether ($Et_2O$), ethyl acetate (EtOAc), ethanol (EtOH), methanol (MeOH), tetrahydrofuran (THF).

The following abbreviations and terms have the indicated meanings throughout:

BOC or Boc=tert-butoxycarbonyl
DCM=dichloromethane
DIPEA or DIEA=N,N-diisopropylethylamine
EDCI·HCl=1-ethyl-3-(3-dimethylaminopropyl) carbodiimide hydrochloride
eq=equivalent(s)
Et=ethyl
EtOAc or EA=ethyl acetate
EtOH=ethanol
g=gram
h or hr(s)=hour
HOBt=hydroxybenzotriazole
HPLC=high pressure liquid chromatography
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min(s)=minute(s)
mL=milliliter
mmol=millimole
RP-HPLC=reverse phase-high pressure liquid chromatography
rt or RT=room temperature
THF=tetrahydrofuran
TLC=thin layer chromatography
UV=ultraviolet

Example 1 General Synthesis Schemes and Synthesis of Common Intermediates

General Scheme 1: Synthesis of alkenyl-methoxy substituted aniline intermediate.

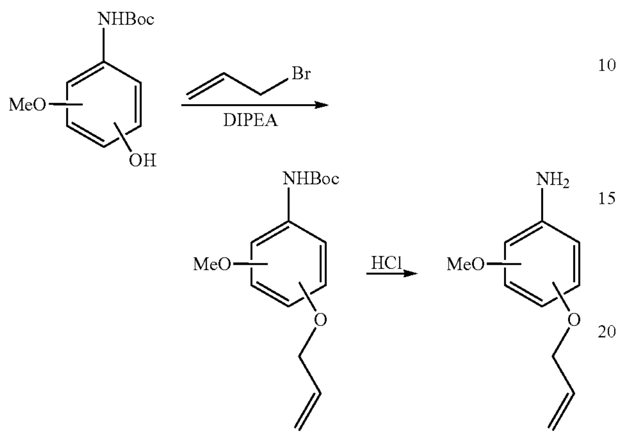

Method 1—General procedure for the synthesis of alkenyl-methoxy substituted aniline derivatives (shown in General Scheme 1). A solution of tert-butyl (hydroxy-methoxyphenyl)carbamate (1.0 equiv.) in acetonitrile was added potassium carbonate (3.0 equiv.) and allyl bromide (1.2 equiv.) and stirred at 80° C. The reaction mixture was cooled, filtered and then concentrated in vacuo. The crude product (tert-butyl ((allyloxy)-methoxyphenyl)carbamate) was purified by automated normal phase chromatography (Method 1a). The Boc amino protecting group of the substituted aniline (tert-butyl ((allyloxy)-methoxyphenyl)carbamate) was removed by treatment with a solution of hydrochloric acid in dioxane (4 M) for 1 hour at room temperature, then concentrated in vacuo. The corresponding hydrochloride salt was treated with aqueous sat. $NaHCO_3$ (10 mL) and stirred for 20 min. The aqueous reaction mixture was extracted with ethyl acetate (4×15 mL), dried over $Na_2SO_4$, and concentrated to afford the title compound (Method 1b).

General Scheme 2: Synthesis of alkenyl-methylamido substituted aniline intermediate.

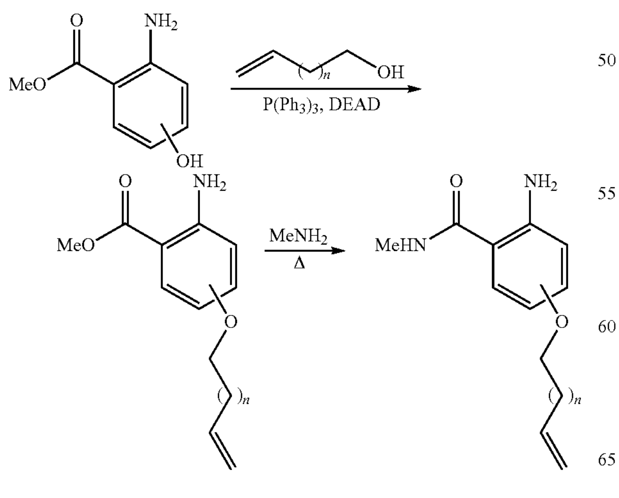

Method 2—General procedure for the synthesis of alkenyl-methylamido substituted aniline derivatives (shown in General Scheme 2). A solution of methyl 2-amino-hydroxybenzoate (1.0 equiv.) in THF was added triphenylphosphine (1.5 equiv.) and the corresponding alkenyl alcohol (1.5 equiv.) and set to stir at room temperature. Diethyl azodicarboxylate (DEAD) (1.5 equiv.) was added dropwise, and the reaction was stirred at room temperature for 4 hours. The reaction mixture was concentrated in vacuo and purified by automated normal phase chromatography (Method 2a). The ester was converted to the corresponding amide by treatment with methylamine (33% solution ethanol) at 85° C. for 24-72 hours in a sealed glass vessel. The reaction mixture was concentrated and purified by automated normal phase chromatography to afford the title compound (Method 2b).

General Scheme 3: Synthesis of macrocyclic ULK inhibitors.

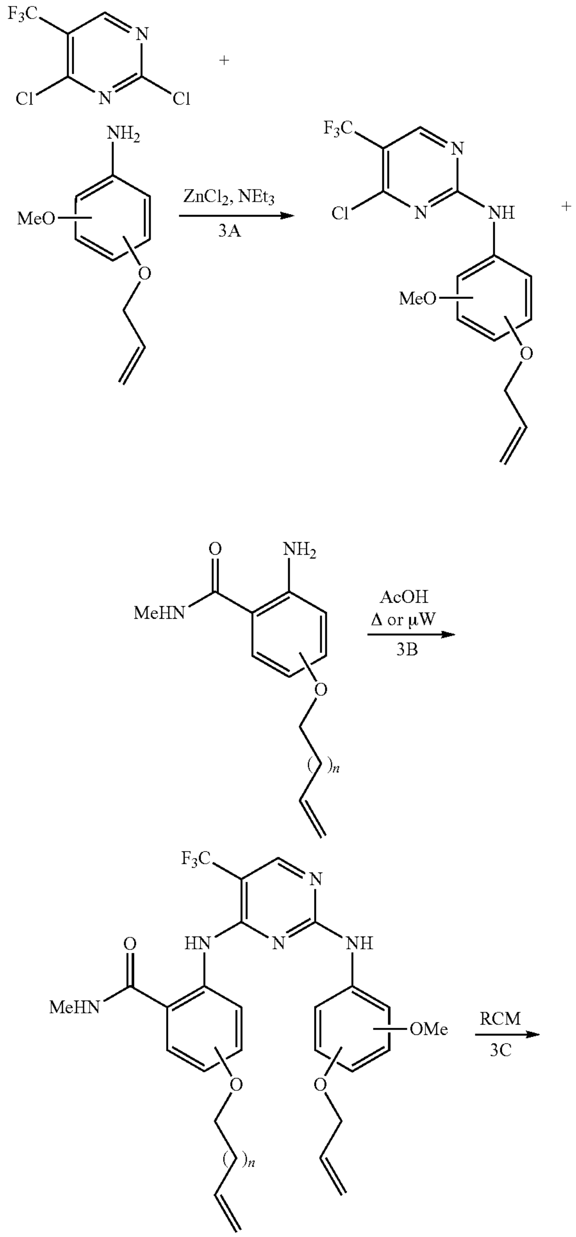

-continued

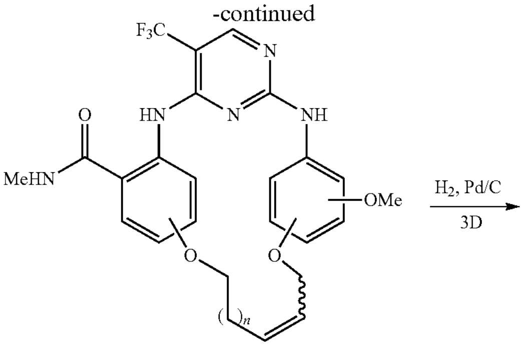

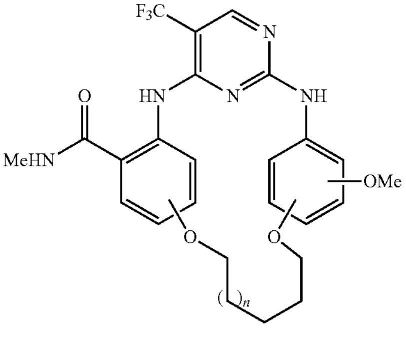

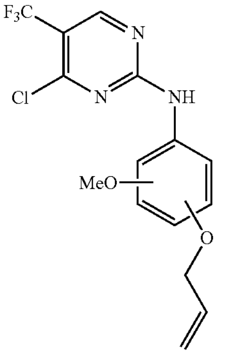

Method 3—General procedure for the synthesis of 4-chloro-5-trifluoromethyl-N-arylpyrimidin-2-amine derivatives (shown in General Scheme 3A). To a solution of 2,4-dichloro-5-(trifluoromethyl)pyrimidine (1.0 equiv.) in 1,2-dichloroethane: t-butanol (1:1) was added zinc chloride (1.2 equiv.) at 0° C. After 1 hour, the appropriate alkenyl-methoxy substituted aniline (1.0 equiv.) and triethylamine (1.2 equiv.) in 1,2-dichloroethane: t-butanol (1:1, 10 mL) was added to the reaction mixture. After 3 hours, the reaction mixture was concentrated in vacuo to obtain the crude product. The crude product was purified by automated normal phase chromatography to afford the desired 4-chloro-5-trifluoromethyl-N-arylpyrimidin-2-amine derivative.

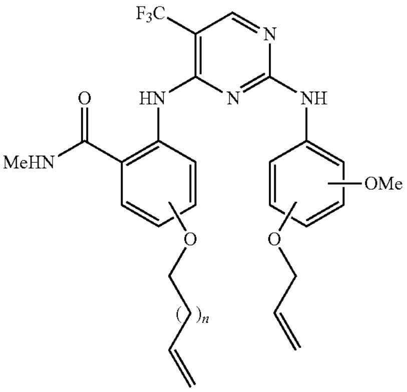

Method 4—General procedure for the synthesis of $N^2$,$N^4$-diaryl-5-(trifluoromethyl)pyrimidine-2,4-diamine derivatives (using reaction conditions 4a and 4b, shown in General Scheme 3B). To a solution of 4-chloro-5-trifluoromethyl-N-arylpyrimidin-2-amine derivative (1.0 equiv.) and the appropriate alkenyl-methylamido substituted aniline (1.1 equiv.) in acetic acid (2 mL) was microwaved at 120° C. for 10 minutes, and then concentrated in vacuo. The crude product was purified by automated normal phase chromatography (Method 4a). To a solution of 4-chloro-5-trifluoromethyl-N-arylpyrimidin-2-amine derivative (1.0 equiv.) and the appropriate amido aniline (1.1 equiv.) in acetic acid was heated at 60° C. The reaction mixture was then concentrated in vacuo and the crude product was purified by automated normal phase chromatography to afford the desired $N^2$,$N^4$-diaryl-5-(trifluoromethyl)pyrimidine-2,4-diamine derivative (Method 4b).

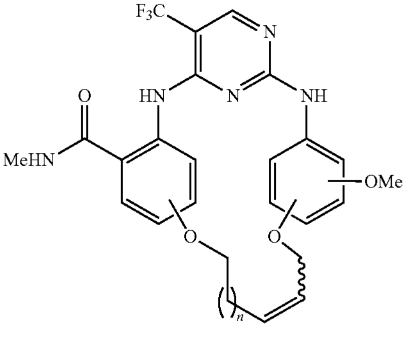

Method 5—General procedure for the synthesis of trans- and cis-(E/Z) unsaturated pyrimidinyl macrocyclic derivatives using Grubbs mediated ring-closing metathesis (shown in General Scheme 3C). A solution of $N^2$,$N^4$-diaryl-5-(trifluoromethyl)pyrimidine-2,4-diamine derivative (1.0 equiv.) in dichloromethane (10 mL) was added drop wise to a refluxing solution of Grubs I catalyst (0.10 equiv.) in dichloromethane (0.50 mM) at 45° C. After 16 hours, additional Grubs I catalyst (0.10 equiv.) was added to the reaction mixture. After an additional 8 hours, the reaction mixture was cooled to room temperature and concentrated in vacuo. The E/Z isomers were separated and purified by automated normal phase chromatography to afford the desired unsaturated pyrimidinyl macrocyclic derivatives.

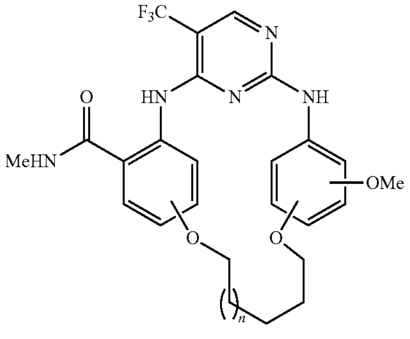

Method 6—General procedure for the synthesis of saturated pyrimidinyl macrocyclic derivatives (shown in General Scheme 3D). To a solution of E/Z unsaturated pyrimidinyl macrocyclic derivative (1.0 equiv.) in methanol was added palladium on carbon (Pd/C) and stirred at room temperature under an atmosphere of hydrogen for 2 hours. The reaction mixture was filtered through celite and subsequently washed with methanol. The filtrate was concentrated under reduced pressure and the crude product was purified by automated normal phase chromatography to afford the desired saturated pyrimidinyl macrocyclic derivative.

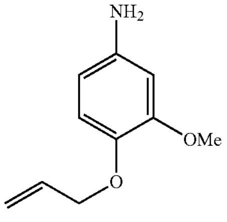

4-(Allyloxy)-3-methoxyaniline. The Boc protected aniline intermediate was prepared by reaction of tert-butyl (4-hydroxy-3-methoxyphenyl)carbamate (1.300 g, 5.43 mmol), allyl bromide (0.56 mL, 6.52 mmol), and potassium carbonate (2.253 g, 16.3 mmol) in acetonitrile (30 mL) for 20 hour according to Method 1a to provide tert-butyl (4-(allyloxy)-3-methoxyphenyl)carbamate as a white solid (1.490 g, 98%). $^1$H NMR (400 MHz, DMSO-$d_6$) δ 9.13 (s, 1H), 7.20 (s, 1H), 6.88 (s, 1H), 6.83 (d, J=8.7 Hz, 1H), 6.01 (ddt, J=17.3, 10.6, 5.4 Hz, 1H), 5.35 (dq, J=17.3, 1.7 Hz, 1H), 5.21 (dq, J=10.6, 1.9, 1.4 Hz, 1H), 4.45 (dt, J=5.4, 1.5 Hz, 2H), 3.71 (s, 3H), 1.46 (s, 9H).

The title compound was prepared by reaction of the Boc protected aniline intermediate tert-butyl (4-(allyloxy)-3-methoxyphenyl)carbamate (1.490 g, 5.33 mmol) and hydrochloric acid (10 mL, 40 mmol, 4 M in dioxane) for 1 hour and processed according to Method 2b to provide the title compound as a white solid (868 mg, 91%). LC-MS (ESI) calcd. for $C_{10}H_{14}NO_2$ [M+H]$^+$: 180.10. found: 180.40.

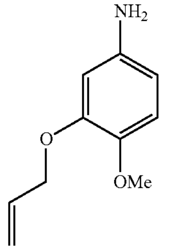

3-(Allyloxy)-4-methoxyaniline. The Boc protected aniline intermediate was prepared by reaction of tert-butyl (3-hydroxy-4-methoxyphenyl)carbamate (4.401 g, 18.4 mmol), allyl bromide (2.39 mL, 27.6 mmol), and potassium carbonate (7.626 g, 55.2 mmol) in acetonitrile (100 mL) for 3 hours according to Method 1a to provide tert-butyl (3-(allyloxy)-4-methoxyphenyl)carbamate as a white solid (3.397 g, 66%). LC-MS (ESI) calcd. for $C_{11}H_{14}NO_4$ [(M-$^t$Bu)+H]$^+$: 224.09. found: 224.35.

The hydrochloride salt was prepared by reaction of the Boc protected aniline intermediate tert-butyl (3-(allyloxy)-4-methoxyphenyl)carbamate (3.387 g, 12.13 mmol) and hydrochloric acid (8.0 mL, 32 mmol, 4 M in dioxane) for 1 hour and processed according to Method 2b to provide the hydrochloride salt of the title compound as a brown solid (2.384 mg, 91%). LC-MS (ESI) calcd. for $C_{10}H_{14}NO_2$ [M+H]$^+$: 180.10. found: 180.40. $^1$H NMR (400 MHz, DMSO-$d_6$) δ 10.18 (s, 2H), 7.05 (d, J=8.6 Hz, 1H), 7.00 (t, J=1.9 Hz, 1H), 6.93 (dd, J=8.3, 2.4 Hz, 1H), 6.04 (ddt, J=17.3, 10.6, 5.4 Hz, 1H), 5.41 (dq, J=17.3, 1.6 Hz, 1H), 5.28 (dq, J=10.5, 1.5 Hz, 1H), 4.54 (dt, J=5.4, 1.3 Hz, 2H), 3.77 (s, 3H).

The title compound was prepared by neutralization of the hydrochloride salt (257 mg, 1.19 mmol) according to Method 2b to afford a sticky brown solid (209 mg, 98%). LC-MS (ESI) calcd. for $C_{10}H_{14}NO_2$ [M+H]$^+$: 180.10. found: 180.00. $^1$H NMR (400 MHz, DMSO-$d_6$) δ 6.66 (d, J=8.5 Hz, 1H), 6.28 (d, J=2.6 Hz, 1H), 6.10 (dd, J=8.5, 2.5 Hz, 1H), 6.08-5.96 (m, 1H), 5.37 (dq, J=17.3, 1.7 Hz, 1H), 5.23 (dq, J=10.4, 1.7 Hz, 1H), 4.65 (s, 2H), 4.44 (dt, J=5.2, 1.7 Hz, 2H), 3.62 (s, 3H).

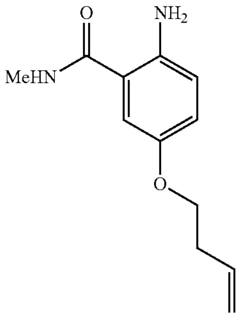 [SMILES: C=CCCOc1ccc(N)c(C(=O)NC)c1]

2-Amino-5-(but-3-en-1-yloxy)-N-methylbenzamide. The methyl ester intermediate was prepared by reaction of methyl 2-amino-5-hydroxybenzoate (1.200 g, 7.18 mmol), but-3-en-1-ol (0.93 mL, 10.8 mmol), triphenylphosphine (2.824 mg, 10.8 mmol), and DEAD (1.70 mL, 10.8 mmol) in THF (10 mL) according to Method 2a to provide methyl 2-amino-5-(but-3-en-1-yloxy)benzoate as a yellow solid (1.204 g, 76%). LC-MS (ESI) calcd. for $C_{12}H_{16}NO_3$ [M+H]$^+$: 222.11. found: 222.40. $^1$H NMR (400 MHz, $CDCl_3$-d) δ 7.35 (d, J=3.1 Hz, 1H), 6.95 (dd, J=8.7, 2.8 Hz, 1H), 6.61 (d, J=8.7 Hz, 1H), 5.89 (ddt, J=17.0, 10.2, 6.7 Hz, 1H), 5.21-5.05 (m, 2H), 3.95 (t, J=6.7 Hz, 2H), 3.86 (s, 3H), 2.52 (dt, J=6.9, 1.5 Hz, 1H), 2.48 (dt, J=6.7, 1.7 Hz, 1H).

The title compound was prepared by reaction of the methyl ester intermediate methyl 2-amino-5-(but-3-en-1-yloxy)benzoate (1.062 g, 4.80 mmol) and methylamine solution (10 mL, 81.6 mmol, 33% in ethanol) for 24 hours according to Method 2b to provide the title compound as a tan solid (747 mg, 71%). LC-MS (ESI) calcd. for $C_{12}H_{17}N_2O_2$ $[M+H]^+$: 221.13. found: 221.40. $^1H$ NMR (400 MHz, DMSO-$d_6$) δ 8.17 (q, J=4.6 Hz, 1H), 7.04 (d, J=2.8 Hz, 1H), 6.82 (dd, J=8.7, 2.8 Hz, 1H), 6.63 (d, J=8.8 Hz, 1H), 6.01 (s, 2H), 5.88 (ddt, J=17.0, 10.2, 6.6 Hz, 1H), 5.15 (dq, J=17.4, 1.6 Hz, 1H), 5.10-5.03 (m, 1H), 3.92 (t, J=6.7 Hz, 2H), 2.71 (d, J=4.5 Hz, 3H), 2.45 (dt, J=6.5, 1.5 Hz, 1H), 2.41 (dt, J=6.7, 1.5 Hz, 1H).

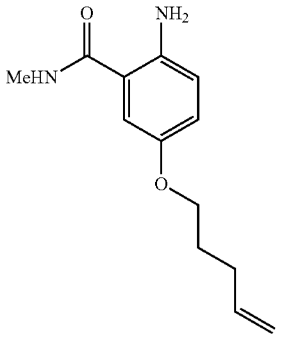 [SMILES: C=CCCCOc1ccc(N)c(C(=O)NC)c1]

2-Amino-N-methyl-5-(pent-4-en-1-yloxy)benzamide. The methyl ester intermediate was prepared by reaction of methyl 2-amino-5-hydroxybenzoate (500 mg, 2.99 mmol), pent-4-en-1-ol (0.46 mL, 4.49 mmol), triphenylphosphine (1.185 mg, 4.52 mmol), and DEAD (0.71 mL, 4.49 mmol) in THF (5 mL) according to Method 2a to provide methyl 2-amino-5-(pent-4-en-1-yloxy)benzoate as a white solid (570 mg, 81%). LC-MS (ESI) calcd. for $C_{13}H_{18}NO_3$ $[M+H]^+$: 236.13. found: 236.45.

The title compound was prepared by reaction of the methyl ester intermediate methyl 2-amino-5-(pent-4-en-1-yloxy)benzoate (560 mg, 2.38 mmol) and methylamine solution (5 mL, 40 mmol, 33% in ethanol) for 48 hours according to Method 2b to provide the title compound as a white solid (286 mg, 51%). LC-MS (ESI) calcd. for $C_{13}H_{19}N_2O_2$ $[M+H]^+$: 235.14. found: 235.45.

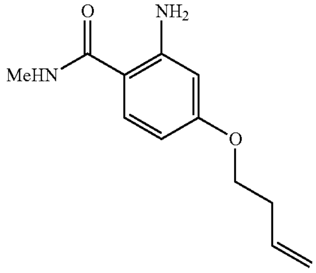 [SMILES: C=CCCOc1ccc(C(=O)NC)c(N)c1]

2-Amino-4-(but-3-en-1-yloxy)-N-methylbenzamide. The methyl ester intermediate was prepared by reaction of methyl 2-amino-4-hydroxybenzoate (1.200 g, 7.18 mmol), but-3-en-1-ol (0.93 mL, 10.8 mmol), triphenylphosphine (2.824 mg, 10.8 mmol), and DEAD (1.70 mL, 10.8 mmol) in THF (12 mL) according to Method 2a to provide methyl 2-amino-4-(but-3-en-1-yloxy)benzoate as a white solid (1.374 mg, 87%). LC-MS (ESI) calcd. for $C_{12}H_{16}NO_3$ $[M+H]^+$: 222.11. found: 222.40. $^1H$ NMR (400 MHz, $CDCl_3$-d) δ 7.74 (d, J=8.8 Hz, 1H), 6.18 (dd, J=8.9, 2.5 Hz, 1H), 6.05 (d, J=2.4 Hz, 1H), 5.89-5.77 (m, 1H), 5.17-5.03 (m, 2H), 3.90 (t, J=6.7 Hz, 2H), 3.78 (s, 3H), 2.56-2.40 (m, 2H).

The title compound was prepared by reaction of the methyl ester intermediate methyl 2-amino-4-(but-3-en-1-yloxy)benzoate (1.187 g, 5.37 mmol) and methylamine solution (8 mL, 64.4 mmol, 33% in ethanol) for 72 hours according to Method 2b to provide the title compound as a white solid (446 mg, 38%). LC-MS (ESI) calcd. for $C_{12}H_{17}N_2O_2$ $[M+H]^+$: 221.13. found: 221.40. $^1H$ NMR (400 MHz, $CDCl_3$-d) δ 7.18 (d, J=9.3 Hz, 1H), 6.56 (q, J=4.8 Hz, 1H), 6.04 (dq, J=5.3, 2.4 Hz, 2H), 5.86-5.70 (m, 1H), 5.10-4.97 (m, 2H), 3.83 (t, J=6.7 Hz, 2H), 2.77 (d, J=4.6 Hz, 3H), 2.48-2.33 (m, 2H).

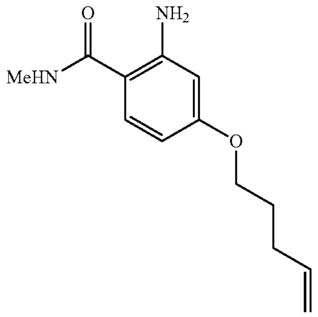 [SMILES: C=CCCCOc1ccc(C(=O)NC)c(N)c1]

2-Amino-N-methyl-4-(pent-4-en-1-yloxy)benzamide. The methyl ester intermediate was prepared by reaction of methyl 2-amino-4-hydroxybenzoate (1.100 g, 6.58 mmol), pent-4-en-1-ol (1.0 mL, 9.87 mmol), triphenylphosphine (2.598 mg, 9.87 mmol), and DEAD (1.55 mL, 9.87 mmol) in THF (11 mL) according to Method 2a to provide methyl 2-amino-4-(pent-4-en-1-yloxy)benzoate as a yellow solid (1.302 mg, 84%). LC-MS (ESI) calcd. for $C_{13}H_{18}NO_3$ $[M+H]^+$: 236.13. found: 236.45.

The title compound was prepared by reaction of the methyl ester intermediate methyl 2-amino-4-(pent-4-en-1-yloxy)benzoate (1.291 g, 5.49 mmol) and methylamine solution (8 mL, 64.2 mmol, 33% in ethanol) for 72 hours according to Method 2b to provide the title compound as a yellow solid (319 mg, 25%). LC-MS (ESI) calcd. for $C_{13}H_{19}N_2O_2$ $[M+H]^+$: 235.14. found: 235.45. $^1H$ NMR (400 MHz, $CDCl_3$-d) δ 7.20 (d, J=8.4 Hz, 1H), 6.42 (d, J=4.8 Hz, 1H), 6.12-6.07 (m, 2H), 5.79 (ddt, J=16.9, 10.3, 6.6 Hz, 1H), 5.04-4.92 (m, 2H), 3.83 (t, J=6.4 Hz, 2H), 2.82 (d, J=4.7 Hz, 3H), 2.15 (q, J=7.0 Hz, 2H), 1.78 (p, J=6.6 Hz, 2H).

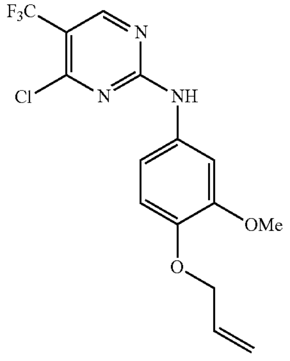 [SMILES: C=CCOc1ccc(Nc2ncc(C(F)(F)F)c(Cl)n2)cc1OC]

N-(4-(Allyloxy)-3-methoxyphenyl)-4-chloro-5-(trifluoromethyl)pyrimidin-2-amine. The title compound was prepared by reaction of 2,4-dichloro-5-(trifluoromethyl)pyrimidine (628 mg, 2.90 mmol), 4-(allyloxy)-3-methoxyaniline (540 mg, 3.01 mmol), zinc chloride (474 mg, 3.48 mmol), and triethylamine (0.48 mL, 3.48 mmol) in 1,2-dichloroethane: t-butanol (1:1, 30 mL) according to Method 3 to provide the title compound as a yellow solid (939 mg, 90%). LC-MS (ESI) calcd. for $C_{15}H_{14}ClF_3N_3O_2$ $[M+H]^+$: 360.07. found: 360.10. $^1H$ NMR (400 MHz, $CD_3OD$-$d_4$) δ 8.58 (s, 1H), 7.39 (s, 1H), 7.13 (dd, J=8.7, 2.5 Hz, 1H), 6.98-6.86 (m, 1H), 6.07 (ddt, J=17.6, 10.7, 5.4 Hz, 1H), 5.38 (dq, J=17.2, 1.8 Hz, 1H), 5.24 (dq, J=10.4, 1.6 Hz, 1H), 4.59-4.51 (m, 2H), 3.85 (s, 3H).

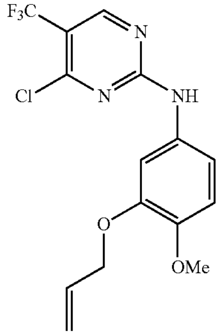 [SMILES: C=CCOc1cc(Nc2ncc(C(F)(F)F)c(Cl)n2)ccc1OC]

N-(3-(Allyloxy)-4-methoxyphenyl)-4-chloro-5-(trifluoromethyl)pyrimidin-2-amine. The title compound was prepared by reaction of 2,4-dichloro-5-(trifluoromethyl)pyrimidine (1.316 g, 6.07 mmol), 3-(allyloxy)-4-methoxyaniline (1.130 g, 6.31 mmol), zinc chloride (0.992 g, 7.28 mmol), and triethylamine (1.0 mL, 7.28 mmol) in 1,2-dichloroethane: t-butanol (1:1, 60 mL) according to Method 3 to provide the title compound as a yellow solid (1.985 g, 91%). LC-MS (ESI) calcd. for $C_{15}H_{14}C_1F_3N_3O_2$ $[M+H]^+$: 360.07. found: 360.40. $^1H$ NMR (400 MHz, $CD_3OD$-$d_4$) δ 10.48 (s, 1H), 8.74 (s, 1H), 7.38 (s, 1H), 7.19 (d, J=8.9 Hz, 1H), 6.95 (d, J=8.8 Hz, 1H), 6.05 (ddt, J=16.0, 10.6, 5.4 Hz, 1H), 5.42 (dq, J=17.0, 1.8 Hz, 1H), 5.27 (dd, J=10.5, 1.8 Hz, 1H), 4.52 (d, J=5.5 Hz, 2H), 3.75 (s, 3H).

Example 2 Synthesis of Compound 2

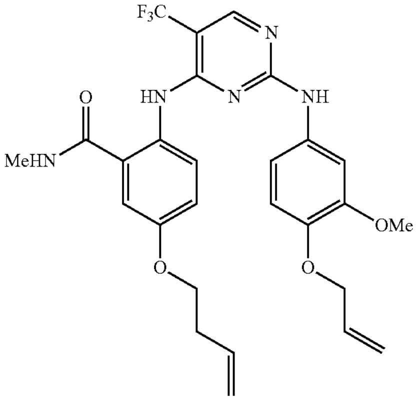 [SMILES: C=CCCOc1ccc(Nc2nc(Nc3ccc(OCC=C)c(OC)c3)ncc2C(F)(F)F)c(C(=O)NC)c1]

2-((2-((4-(Allyloxy)-3-methoxyphenyl)amino)-5-(trifluoromethyl)pyrimidin-4-yl)amino)-5-(but-3-en-1-yloxy)-N-methylbenzamide (Compound 2). The title compound was prepared by reaction of N-(4-(allyloxy)-3-methoxyphenyl)-4-chloro-5-(trifluoromethyl)pyrimidin-2-amine (240 mg, 0.67 mmol) and 2-amino-5-(but-3-en-1-yloxy)-N-methylbenzamide (169 mg, 0.77 mmol) in acetic acid (2 mL) according to Method 4a to provide the title compound as a yellow solid (339 mg, 94%). LC-MS (ESI) calcd. for $C_{27}H_{29}F_3N_5O_4[M+H]^+$: 544.22. found: 544.80. $^1H$ NMR (400 MHz, DMSO-$d_6$) δ 11.03 (s, 1H), 9.19 (s, 1H), 8.73 (q, J=4.6 Hz, 1H), 8.50 (d, J=7.6 Hz, 1H), 8.20 (s, 1H), 7.28 (d, J=3.0 Hz, 1H), 7.26-7.10 (m, 2H), 7.00 (dd, J=9.2, 2.9 Hz, 1H), 6.85 (d, J=8.7 Hz, 1H), 6.03 (ddt, J=17.3, 10.5, 5.3 Hz, 1H), 5.91 (ddt, J=17.0, 10.3, 6.6 Hz, 1H), 5.42-5.32 (m, 1H), 5.26-5.06 (m, 3H), 4.56-4.43 (m, 2H), 4.07 (t, J=6.6 Hz, 2H), 3.64 (s, 3H), 2.79 (d, J=4.5 Hz, 3H), 2.55-2.46 (m, 1H).

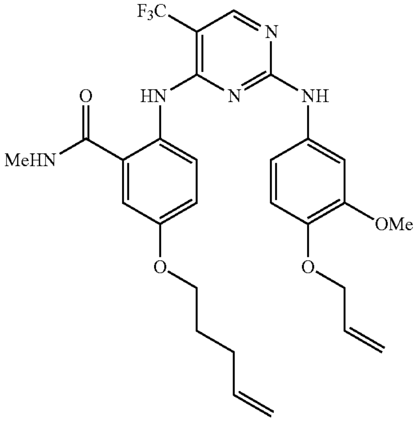 [SMILES: C=CCCCOc1ccc(Nc2nc(Nc3ccc(OCC=C)c(OC)c3)ncc2C(F)(F)F)c(C(=O)NC)c1]

Example 3 Synthesis of Compound 5

2-((2-((4-(Allyloxy)-3-methoxyphenyl)amino)-5-(trifluoromethyl)pyrimidin-4-yl)amino)-N-methyl-5-(pent-4-en-1-yloxy)benzamide (Compound 5). The title compound was prepared by reaction of N-(4-(allyloxy)-3-methoxyphenyl)-4-chloro-5-(trifluoromethyl)pyrimidin-2-amine (183 mg, 0.51 mmol) and 2-amino-N-methyl-5-(pent-4-en-1-yloxy)benzamide (137 mg, 0.58 mmol) in acetic acid (2 mL)

according to Method 4a to provide the title compound as a yellow solid (82 mg, 29%). LC-MS (ESI) calcd. for $C_{28}H_{31}F_3N_5O_4[M+H]^+$: 558.23. found: 558.75. $^1H$ NMR (400 MHz, DMSO-$d_6$) δ 10.94 (s, 1H), 9.57 (s, 1H), 8.71 (q, J=4.7 Hz, 1H), 8.40 (s, 1H), 8.36 (s, 1H), 7.25 (d, J=3.0 Hz, 1H), 7.17 (d, J=32.6 Hz, 2H), 6.96 (s, 1H), 6.86 (d, J=8.6 Hz, 1H), 6.04 (ddt, J=16.9, 10.7, 5.7 Hz, 1H), 5.88 (ddt, J=16.8, 10.2, 6.5 Hz, 1H), 5.38 (dq, J=17.6, 1.9 Hz, 1H), 5.24 (dq, J=10.7, 1.7 Hz, 1H), 5.07 (dq, J=17.2, 1.8 Hz, 1H), 5.05-4.97 (m, 1H), 4.51 (dt, J=5.4, 1.5, 1.3 Hz, 2H), 4.02 (t, J=6.4 Hz, 2H), 3.60 (s, 3H), 2.77 (d, J=4.4 Hz, 3H), 2.20 (q, J=7.1 Hz, 2H), 1.83 (p, J=6.5 Hz, 2H).

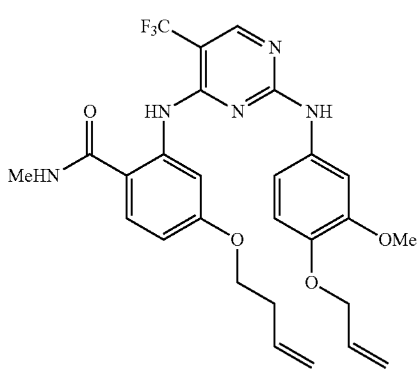 [SMILES: C=CCCOc1ccc(C(=O)NC)c(Nc2nc(Nc3ccc(OCC=C)c(OC)c3)ncc2C(F)(F)F)c1]

2-((2-((4-(Allyloxy)-3-methoxyphenyl)amino)-5-(trifluoromethyl)pyrimidin-4-yl)amino)-4-(but-3-en-1-yloxy)-N-methylbenzamide. The title compound was prepared by reaction of N-(4-(allyloxy)-3-methoxyphenyl)-4-chloro-5-(trifluoromethyl)pyrimidin-2-amine (158 mg, 0.44 mmol) and 2-amino-4-(but-3-en-1-yloxy)-N-methylbenzamide (111 mg, 0.50 mmol) in acetic acid (5 mL) for 4 hours according to Method 4b to provide the title compound as a yellow solid (113 mg, 47%). LC-MS (ESI) calcd. for $C_{27}H_{29}F_3N_5O_4[M+H]^+$: 544.22. found: 545.00.

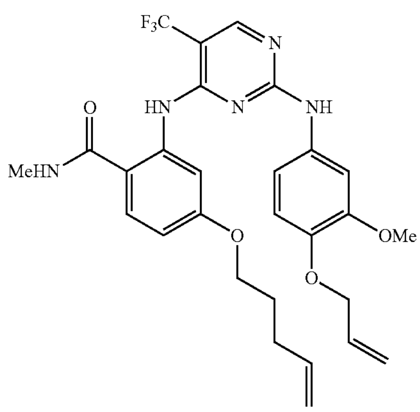 [SMILES: C=CCCCOc1ccc(C(=O)NC)c(Nc2nc(Nc3ccc(OCC=C)c(OC)c3)ncc2C(F)(F)F)c1]

2-((2-((4-(Allyloxy)-3-methoxyphenyl)amino)-5-(trifluoromethyl)pyrimidin-4-yl)amino)-N-methyl-4-(pent-4-en-1-yloxy)benzamide. The title compound was prepared by reaction of N-(4-(allyloxy)-3-methoxyphenyl)-4-chloro-5-(trifluoromethyl)pyrimidin-2-amine (215 mg, 0.60 mmol) and 2-amino-N-methyl-4-(pent-4-en-1-yloxy)benzamide (154 mg, 0.66 mmol) in acetic acid (2 mL) for 4 hours according to Method 4b to provide the title compound as a white solid (279 mg, 84%). LC-MS (ESI) calcd. for $C_{28}H_{31}F_3N_5O_4[M+H]^+$: 558.23. found: 559.15. $^1H$ NMR (400 MHz, DMSO-$d_6$) δ 11.94 (s, 1H), 9.78 (s, 1H), 8.61 (q, J=4.4 Hz, 1H), 8.43 (s, 1H), 7.98 (s, 1H), 7.69 (d, J=8.8 Hz, 1H), 7.27 (s, 1H), 7.04 (d, J=6.4 Hz, 1H), 6.84 (d, J=8.6 Hz, 1H), 6.68 (dd, J=9.0, 2.6 Hz, 1H), 6.03 (ddt, J=22.4, 10.5, 5.4 Hz, 1H), 5.78 (ddt, J=16.8, 10.8, 6.5 Hz, 1H), 5.37 (dd, J=17.9, 1.6 Hz, 1H), 5.24 (dd, J=10.5, 1.6 Hz, 1H), 5.03-4.90 (m, 2H), 4.47 (d, J=5.2 Hz, 2H), 3.49 (s, 3H), 2.76 (d, J=4.4 Hz, 3H), 2.03-1.99 (m, 2H), 1.67-1.63 (m, 2H).

Example 4 Synthesis of Compound 8

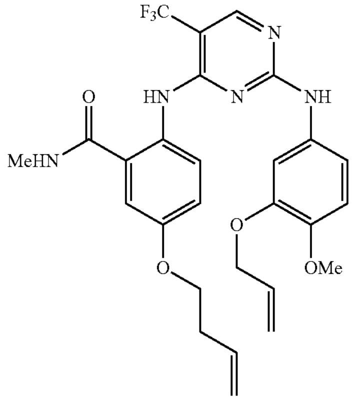 [SMILES: C=CCCOc1ccc(Nc2nc(Nc3ccc(OC)c(OCC=C)c3)ncc2C(F)(F)F)c(C(=O)NC)c1]

2-((2-((3-(Allyloxy)-4-methoxyphenyl)amino)-5-(trifluoromethyl)pyrimidin-4-yl)amino)-5-(but-3-en-1-yloxy)-N-methylbenzamide (Compound 8). The title compound was prepared by reaction of N-(3-(allyloxy)-4-methoxyphenyl)-4-chloro-5-(trifluoromethyl)pyrimidin-2-amine (284 mg, 0.79 mmol) and 2-amino-5-(but-3-en-1-yloxy)-N-methylbenzamide (200 mg, 0.91 mmol) in acetic acid (2 mL) for 1 hours according to Method 4b. The crude reaction mixture was crystalized using diethyl ether/dichloromethane (9:1) to provide the title compound as a yellow solid (401 mg, 93%). LC-MS (ESI) calcd. for $C_{27}H_{29}F_3N_5O_4[M+H]^+$: 544.22. found: 544.80.

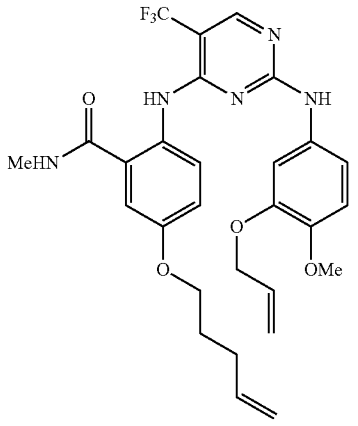 [SMILES: C=CCCCOc1ccc(Nc2nc(Nc3ccc(OC)c(OCC=C)c3)ncc2C(F)(F)F)c(C(=O)NC)c1]

2-((2-((3-(Allyloxy)-4-methoxyphenyl)amino)-5-(trifluoromethyl)pyrimidin-4-yl)amino)-N-methyl-5-(pent-4-en-1-yloxy)benzamide. The title compound was prepared by reaction of N-(3-(allyloxy)-4-methoxyphenyl)-4-chloro-5-(trifluoromethyl)pyrimidin-2-amine (183 mg, 0.51 mmol) and 2-amino-N-methyl-5-(pent-4-en-1-yloxy)benzamide (131 mg, 0.56 mmol) in acetic acid (2 mL) at 45° C. for 2 hours according to Method 4b to provide the title compound as a yellow solid (143 mg, 51%). LC-MS (ESI) calcd. for $C_{28}H_{31}F_3N_5O_4[M+H]^+$: 558.23. found: 558.70. $^1$H NMR (400 MHz, DMSO-$d_6$) δ 11.00 (s, 1H), 9.56 (s, 1H), 8.71 (q, J=4.6 Hz, 1H), 8.35 (s, 1H), 7.26 (d, J=3.1 Hz, 1H), 7.15-7.11 (m, 1H), 6.99-6.94 (m, 1H), 6.86 (d, J=8.7 Hz, 1H), 6.05-5.81 (m, 2H), 5.33 (d, J=17.2 Hz, 1H), 5.21 (d, J=10.5 Hz, 1H), 5.07 (dq, J=17.4, 1.8 Hz, 1H), 5.05-4.96 (m, 1H), 4.35-4.31 (m, 2H), 4.01 (t, J=6.3 Hz, 2H), 3.74 (s, 3H), 2.77 (d, J=4.5 Hz, 3H), 2.20 (qd, J=6.5, 1.5 Hz, 2H), 1.84 (dt, J=8.5, 6.5 Hz, 2H).

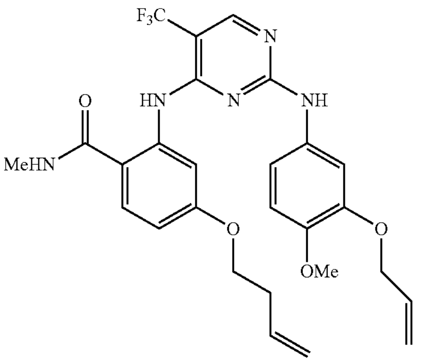 [SMILES: C=CCCOc1ccc(C(=O)NC)c(Nc2nc(Nc3ccc(OC)c(OCC=C)c3)ncc2C(F)(F)F)c1]

2-((2-((3-(Allyloxy)-4-methoxyphenyl)amino)-5-(trifluoromethyl)pyrimidin-4-yl)amino)-4-(but-3-en-1-yloxy)-N-methylbenzamide. The title compound was prepared by reaction of N-(3-(allyloxy)-4-methoxyphenyl)-4-chloro-5-(trifluoromethyl)pyrimidin-2-amine (378 mg, 1.05 mmol) and 2-amino-4-(but-3-en-1-yloxy)-N-methylbenzamide (153 mg, 0.70 mmol) in acetic acid (2 mL) at 50° C. for 4 hours according to Method 4b to provide the title compound as a tan solid (146 mg, 39%). LC-MS (ESI) calcd. for $C_{27}H_{29}F_3N_5O_4[M+H]^+$: 544.22. found: 545.00. $^1$H NMR (400 MHz, DMSO-$d_6$) δ 11.94 (s, 1H), 9.72 (s, 1H), 8.59 (q, J=4.5 Hz, 1H), 8.42 (s, 1H), 8.01 (s, 1H), 7.69 (d, J=9.0 Hz, 1H), 7.26 (s, 1H), 7.08 (d, J=11.2 Hz, 1H), 6.84 (d, J=8.7 Hz, 1H), 6.67 (dd, J=8.7, 2.5 Hz, 1H), 5.94-5.89 (m, 1H), 5.75-5.70 (m, 1H), 5.26 (d, J=12.3 Hz, 1H), 5.17 (d, J=10.3 Hz, 1H), 5.07 (d, J=17.3 Hz, 1H), 5.01 (d, J=10.2 Hz, 1H), 4.23 (s, 3H), 3.75 (d, J=3.4 Hz, 1H), 2.76 (d, J=4.4 Hz, 3H), 2.33 (s, 2H).

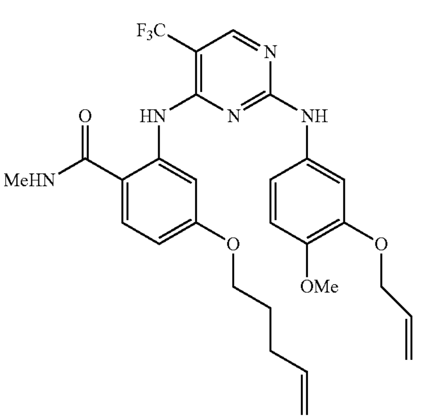 [SMILES: C=CCCCOc1ccc(C(=O)NC)c(Nc2nc(Nc3ccc(OC)c(OCC=C)c3)ncc2C(F)(F)F)c1]

2-((2-((3-(Allyloxy)-4-methoxyphenyl)amino)-5-(trifluoromethyl)pyrimidin-4-yl)amino)-N-methyl-4-(pent-4-en-1-yloxy)benzamide. The title compound was prepared by reaction of N-(3-(allyloxy)-4-methoxyphenyl)-4-chloro-5-(trifluoromethyl)pyrimidin-2-amine (215 mg, 0.60 mmol) and 2-amino-N-methyl-4-(pent-4-en-1-yloxy)benzamide (154 mg, 0.66 mmol) in acetic acid (2 mL) at 85° C. for 5 hours according to Method 4b to provide the title compound as a white solid (254 mg, 76%). LC-MS (ESI) calcd. for $C_{28}H_{31}F_3N_5O_4[M+H]^+$: 558.23. found: 558.75.

Example 5 Synthesis of Compounds 3 and 4

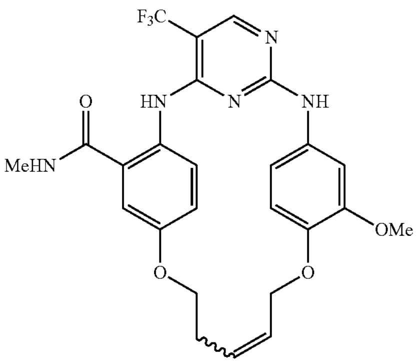 [SMILES: CNC(=O)c1cc2ccc1Nc1nc(ncc1C(F)(F)F)Nc1ccc(c(OC)c1)OCC=CCCO2]

(E/Z)-1$^3$-Methoxy-N-methyl-3$^5$-(trifluoromethyl)-6,12-dioxa-2,4-diaza-3(2,4)-pyrimidina-1,5(1,4)-dibenzenacyclododecaphan-9-ene-5$^2$-carboxamide (Compounds 3 and 4). The title compound was prepared by reaction of 2-((2-((4-(allyloxy)-3-methoxyphenyl)amino)-5-(trifluoromethyl)pyrimidin-4-yl)amino)-5-(but-3-en-1-yloxy)-N-methylbenzamide (73.5 mg, 135 μmol) with catalytic Grubs I catalyst (11 mg, 14 μmol) in dichloromethane (270 mL) for a total of 36 hours according to Method 5 to provide: (E)-1$^3$-methoxy-N-methyl-3$^5$-(trifluoromethyl)-6,12-dioxa-2,4-diaza-3(2,4)-pyrimidina-1,5(1,4)-dibenzenacyclododecaphan-9-ene-5$^2$-carboxamide (white solid, 16 mg, 23%), LC-MS (ESI) calcd. for $C_{25}H_{25}F_3N_5O_4[M+H]^+$: 516.19. found: 516.65 (ret. time 1.8 min). $^1$H NMR (400 MHz, DMSO-$d_6$) δ 9.58 (s, 1H), 9.38 (s, 1H), 8.42 (q, J=4.6 Hz, 1H), 8.28 (s, 1H), 7.51 (d, J=8.9 Hz, 1H), 7.15 (d, J=2.9 Hz, 1H), 7.00 (dd, J=8.9, 2.9 Hz, 1H), 6.86 (dd, J=8.8, 2.4 Hz, 1H), 6.75-6.64 (m, 2H), 5.90 (dt, J=14.4, 6.8 Hz, 1H), 5.59 (dt, J=15.7, 5.6 Hz, 1H), 4.60 (d, J=5.5 Hz, 2H), 4.20 (t, J=5.3 Hz, 2H), 3.66 (s, 3H), 2.70 (d, J=4.4 Hz, 3H), 2.40 (q, J=5.9 Hz, 2H); and (Z)-1$^3$-methoxy-N-methyl-3$^5$-(trifluoromethyl)-6,12-dioxa-2,4-diaza-3(2,4)-pyrimidina-1,5(1,4)-dibenzenacyclododecaphan-9-ene-5$^2$-carboxamide (white solid, 16 mg, 22%). LC-MS (ESI) calcd. for $C_{25}H_{25}F_3N_5O_4[M+H]^+$: 516.19. found: 516.65 (ret. time 1.9 min). $^1$H NMR (400 MHz, DMSO-$d_6$) δ 10.10 (s, 1H), 9.46 (s, 1H), 8.49 (q, J=4.5 Hz, 1H), 8.29 (s, 1H), 7.65 (d, J=9.1 Hz, 1H), 7.17 (d, J=2.8 Hz, 1H), 6.90 (dd, J=8.7, 2.4 Hz, 1H), 6.84 (dd, J=9.1, 2.9 Hz, 1H), 6.79 (d, J=2.4 Hz, 1H), 6.73 (d, J=8.7 Hz, 1H), 5.86-5.71 (m, 2H), 4.53 (d, J=6.0 Hz, 2H), 4.26 (t, J=7.3 Hz, 2H), 3.66 (s, 3H), 2.70 (d, J=4.5 Hz, 3H), 2.56-2.52 (m, 2H).

Example 6 Synthesis of Compound 1

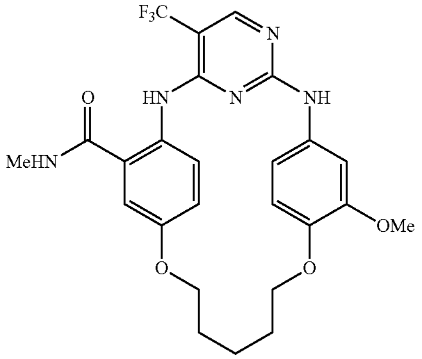 [SMILES: CNC(=O)c1cc2ccc1Nc1nc(ncc1C(F)(F)F)Nc1ccc(c(OC)c1)OCCCCCO2]

$1^3$-Methoxy-N-methyl-$3^5$-(trifluoromethyl)-6,12-dioxa-2,4-diaza-3(2,4)-pyrimidina-1,5(1,4)-dibenzenacyclododecaphane-$5^2$-carboxamide (Compound 1). The title compound was prepared by reaction of (E/Z)-$1^3$-methoxy-N-methyl-$3^5$-(trifluoromethyl)-6,12-dioxa-2,4-diaza-3(2,4)-pyrimidina-1,5(1,4)-dibenzenacyclododecaphan-9-ene-$5^2$-carboxamide (41 mg, 80 μmol) with catalytic Pd/C (5 mg, 47 μmol) in methanol (5 mL) according to Method 6 to provide the title compound as a white solid (26 mg, 63%). LC-MS (ESI) calcd. for $C_{25}H_{27}F_3N_5O_4[M+H]^+$: 518.20. found: 518.60 (ret. time 1.9 min). $^1H$ NMR (400 MHz, DMSO-$d_6$) δ 10.07 (s, 1H), 9.39 (s, 1H), 8.50 (q, J=4.5 Hz, 1H), 8.29 (s, 1H), 7.66 (d, J=9.0 Hz, 1H), 7.13 (d, J=2.8 Hz, 1H), 6.92-6.79 (m, 2H), 6.75 (s, 2H), 4.13-4.06 (m, 2H), 4.04-3.99 (m, 2H), 3.73 (s, 3H), 2.70 (d, J=4.5 Hz, 3H), 1.63-1.58 (m, 2H), 1.56-1.53 (m, 4H).

Example 7 Synthesis of Compound 6

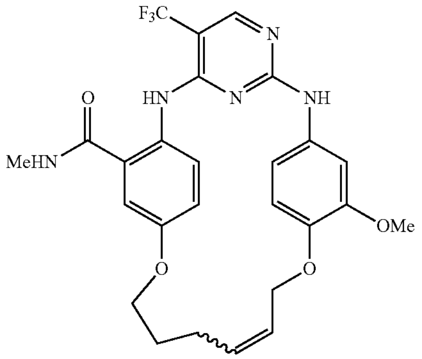 [SMILES: CNC(=O)c1cc2ccc1Nc1nc(ncc1C(F)(F)F)Nc1ccc(c(OC)c1)OCC=CCCCO2]

(E/Z)-$1^3$-Methoxy-N-methyl-$3^5$-(trifluoromethyl)-6,13-dioxa-2,4-diaza-3(2,4)-pyrimidina-1,5(1,4)-dibenzenacyclotridecaphan-10-ene-$5^2$-carboxamide (Compound 6). The title compound was prepared by reaction of 2-((2-((4-(allyloxy)-3-methoxyphenyl)amino)-5-(trifluoromethyl)pyrimidin-4-yl)amino)-N-methyl-5-(pent-4-en-1-yloxy)benzamide (70 mg, 125 mol) with catalytic Grubs I catalyst (10 mg, 13 μmol) in dichloromethane (250 mL) for a total of 22 hours according to Method 5 to provide: (E)-$1^3$-methoxy-N-methyl-$3^5$-(trifluoromethyl)-6,13-dioxa-2,4-diaza-3(2,4)-pyrimidina-1,5(1,4)-dibenzenacyclotridecaphan-10-ene-$5^2$-carboxamide (white solid, 12 mg, 19%), LC-MS (ESI) calcd. for $C_{26}H_{27}F_3N_5O_4[M+H]^+$: 530.20. found: 530.75 (ret. time 2.0 min). $^1H$ NMR (400 MHz, DMSO-$d_6$) δ 10.29 (s, 1H), 9.49 (s, 1H), 8.58 (q, J=4.6 Hz, 1H), 8.31 (s, 1H), 7.97 (d, J=9.0 Hz, 1H), 7.19 (d, J=2.8 Hz, 1H), 7.11 (dd, J=8.7, 2.4 Hz, 1H), 7.03 (dd, J=9.2, 2.8 Hz, 1H), 6.84 (d, J=8.8 Hz, 1H), 6.77 (d, J=2.5 Hz, 1H), 5.86 (dt, J=14.4, 6.7 Hz, 1H), 5.59 (dt, J=15.9, 5.5 Hz, 1H), 4.62 (d, J=5.5 Hz, 2H), 4.12 (t, J=6.7 Hz, 2H), 3.67 (s, 3H), 2.72 (d, J=4.5 Hz, 3H), 2.15 (q, J=6.6, 6.2 Hz, 2H), 1.79 (p, J=6.3 Hz, 2H); and a mixture of isomers (E/Z)-$1^3$-methoxy-N-methyl-$3^5$-(trifluoromethyl)-6,13-dioxa-2,4-diaza-3(2,4)-pyrimidina-1,5(1,4)-dibenzenacyclotridecaphan-10-ene-$5^2$-carboxamide (white solid, 30 mg, 46%).

Example 8 Synthesis of Compound 7

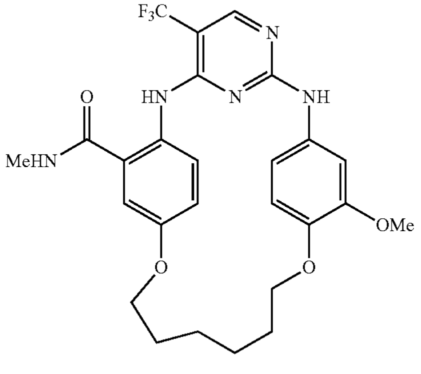 [SMILES: CNC(=O)c1cc2ccc1Nc1nc(ncc1C(F)(F)F)Nc1ccc(c(OC)c1)OCCCCCCO2]

$1^3$-Methoxy-N-methyl-$3^5$-(trifluoromethyl)-6,13-dioxa-2,4-diaza-3(2,4)-pyrimidina-1,5(1,4)-dibenzenacyclotridecaphane-$5^2$-carboxamide (Compound 7). The title compound was prepared by reaction of (E/Z)-$1^3$-methoxy-N-methyl-$3^5$-(trifluoromethyl)-6,13-dioxa-2,4-diaza-3(2,4)-pyrimidina-1,5(1,4)-dibenzenacyclotridecaphan-10-ene-$5^2$-carboxamide (30 mg, 57 μmol) with Pd/C (10 mg, 94 μmol) in methanol (10 mL) according to Method 6 to provide the title compound as a yellow solid (20 mg, 67%). LC-MS (ESI) calcd. for $C_{26}H_{29}F_3N_5O_4[M+H]^+$: 532.22. found: 532.30 (ret. time 2.0 min). $^1H$ NMR (400 MHz, DMSO-$d_6$) δ 10.49 (s, 1H), 9.52 (s, 1H), 8.63 (q, J=4.6 Hz, 1H), 8.32 (s, 1H), 8.01 (d, J=9.0 Hz, 1H), 7.18 (d, J=2.8 Hz, 1H), 7.15 (dd, J=8.7, 2.4 Hz, 1H), 7.04 (dd, J=9.2, 2.8 Hz, 1H), 6.90-6.82 (m, 2H), 4.16 (t, J=7.1 Hz, 2H), 4.09 (t, J=6.4 Hz, 2H), 3.65 (s, 3H), 2.72 (d, J=4.5 Hz, 3H), 1.71-1.56 (m, 4H), 1.48-1.43 (m, 4H).

Example 9 Synthesis of Compounds 15 and 16

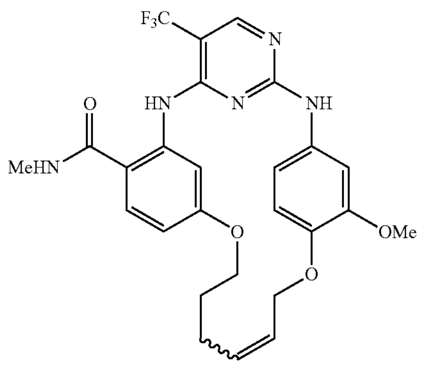 [SMILES: CNC(=O)c1ccc2cc1Nc1nc(ncc1C(F)(F)F)Nc1ccc(c(OC)c1)OCC=CCCCO2]

(E/Z)-$5^3$-Methoxy-N-methyl-$3^5$-(trifluoromethyl)-6,13-dioxa-2,4-diaza-3(4,2)-pyrimidina-1(1,3),5(1,4)-dibenzenacyclotridecaphan-8-ene-$1^6$-carboxamide (Compounds 15 and 16). The title compound was prepared by reaction of 2-((2-((4-(allyloxy)-3-methoxyphenyl)amino)-5-(trifluoromethyl)pyrimidin-4-yl)amino)-N-methyl-4-(pent-4-en-1-yloxy)benzamide (100 mg, 179 μmol) with catalytic Grubs I catalyst (15 mg, 18 μmol) in dichloromethane (359 mL) for a total of 40 hours according to Method 5 to provide: (E)-$5^3$-methoxy-N-methyl-$3^5$-(trifluoromethyl)-6,13-dioxa-2,4-diaza-3(4,2)-pyrimidina-1(1,3),5(1,4)-dibenzenacyclotridecaphan-8-ene-$1^6$-carboxamide (white solid, 12 mg, 13%), LC-MS (ESI) calcd. for $C_{26}H_{27}F_3N_5O_4[M+H]^+$: 530.20. found: 530.60 (ret. time 2.4 min). $^1H$ NMR (400 MHz, DMSO-$d_6$) δ 11.92 (s, 1H), 9.85 (s, 1H), 8.60 (q, J=4.6 Hz, 1H), 8.44 (s, 1H), 7.86 (d, J=2.6 Hz, 1H), 7.64 (d, J=8.8 Hz, 1H), 7.24 (d, J=2.5 Hz, 1H), 7.17 (dd, J=8.7, 2.4 Hz, 1H), 6.73 (d, J=8.7 Hz, 1H), 6.64 (dd, J=8.9, 2.5 Hz, 1H), 5.52 (dt, J=15.4, 5.7 Hz, 1H), 5.33 (dt, J=15.0, 7.0 Hz, 1H), 4.51 (d, J=5.8 Hz, 2H), 3.42 (s, 3H), 3.38 (t, J=5.5 Hz, 2H), 2.76 (d, J=4.5 Hz, 3H), 2.17 (q, J=6.9 Hz, 2H), 1.64-1.54 (m, 1H); (Z)-$5^3$-methoxy-N-methyl-$3^5$-(trifluoromethyl)-6,13-dioxa-2,4-diaza-3(4,2)-pyrimidina-1(1,3),5(1,4)-dibenzenacyclotridecaphan-8-ene-$1^6$-carboxamide (white solid, 6 mg, 6%), LC-MS (ESI) calcd. for $C_{26}H_{27}F_3N_5O_4[M+H]^+$: 530.20. found: 530.65 (ret. time 2.3 min). $^1H$ NMR (400 MHz, DMSO-$d_6$) δ 11.85 (s, 1H), 9.78 (s, 1H), 8.60 (q, J=4.4 Hz, 1H), 8.41 (s, 1H), 7.93 (d, J=2.3 Hz, 1H), 7.68 (d, J=8.9 Hz, 1H), 7.20 (d, J=2.4 Hz, 1H), 7.06 (dd, J=8.7, 2.4 Hz, 1H), 6.81 (d, J=8.5 Hz, 1H), 6.71 (dd, J=8.8, 2.4 Hz, 1H), 5.60 (t, J=4.5 Hz, 2H), 4.58 (d, J=4.5 Hz, 2H), 3.76 (t, J=5.0 Hz, 2H), 3.46 (s, 3H), 2.76 (d, J=4.4 Hz, 3H), 2.16 (q, J=6.5 Hz, 2H), 1.70 (p, J=6.3 Hz, 2Hf).; and a mixture of isomers (E/Z)-$5^3$-methoxy-N-methyl-$3^5$-(trifluoromethyl)-6,13-dioxa-2,4-diaza-3(4,2)-pyrimidina-1(1,3),5 (1,4)-dibenzenacyclotridecaphan-8-ene-$1^6$-carboxamide (white solid, 73 mg, 77%).

Example 10 Synthesis of Compound 17

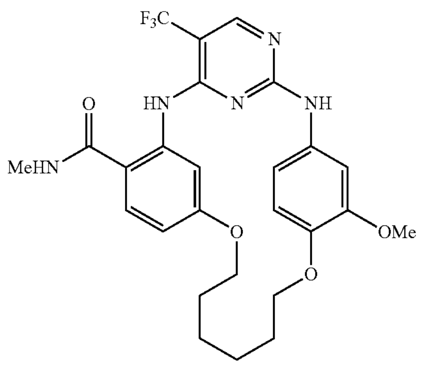 [SMILES: CNC(=O)c1ccc2cc1Nc1nc(ncc1C(F)(F)F)Nc1ccc(c(OC)c1)OCCCCCCO2]

$5^3$-Methoxy-N-methyl-$3^5$-(trifluoromethyl)-6,13-dioxa-2,4-diaza-3(4,2)-pyrimidina-1(1,3),5 (1,4)-dibenzenacyclotridecaphane-16-carboxamide (Compound 17). The title compound was prepared by reaction of (E/Z)-$5^3$-methoxy-N-methyl-$3^5$-(trifluoromethyl)-6,13-dioxa-2,4-diaza-3(4,2)-pyrimidina-1(1,3),5 (1,4)-dibenzenacyclotridecaphan-8-ene-$1^6$-carboxamide (68 mg, 129 μmol) with catalytic Pd/C (5 mg, 50 μmol) in methanol (10 mL) according to Method 6 to provide the title compound as a yellow solid (58 mg, 84%). LC-MS (ESI) calcd. for $C_{26}H_{29}F_3N_5O_4[M+H]^+$: 532.22. found: 532.20 (ret. time 2.3 min). $^1H$ NMR (400 MHz, DMSO-$d_6$) δ 11.93 (s, 1H), 9.79 (s, 1H), 8.60 (q, J=4.6 Hz, 1H), 8.41 (s, 1H), 7.90 (d, J=2.6 Hz, 1H), 7.69 (d, J=8.7 Hz, 1H), 7.28 (d, J=2.2 Hz, 1H), 6.95-6.84 (m, 2H), 6.69 (dd, J=8.8, 2.5 Hz, 1H), 4.16 (t, J=4.9 Hz, 2H), 3.71 (t, J=5.5 Hz, 2H), 3.35 (s, 3H), 2.76 (d, J=4.5 Hz, 3H), 1.67-1.52 (m, 4H), 1.48-1.35 (m, 4H).

Example 11 Synthesis of Compounds 18 and 19

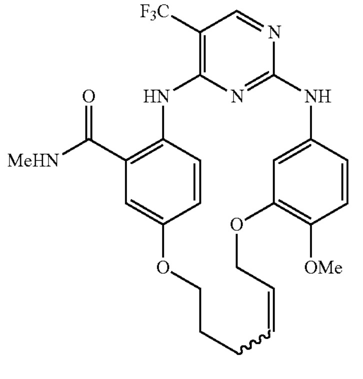 [SMILES: CNC(=O)c1cc2ccc1Nc1nc(ncc1C(F)(F)F)Nc1ccc(OC)c(c1)OCC=CCCCO2]

(E/Z)-$1^4$-Methoxy-N-methyl-$3^5$-(trifluoromethyl)-6,13-dioxa-2,4-diaza-3(2,4)-pyrimidina-1(1,3),5(1,4)-dibenzenacyclotridecaphan-10-ene-$5^2$-carboxamide (Compounds 18 and 19). The title compound was prepared by reaction of 2-((2-((3-(allyloxy)-4-methoxyphenyl)amino)-5-(trifluoromethyl)pyrimidin-4-yl)amino)-N-methyl-5-(pent-4-en-1-yloxy)benzamide (61 mg, 110 μmol) with catalytic Grubs I catalyst (9 mg, 11 μmol) in dichloromethane (220 mL) according to Method 5 to provide: (E)-$1^4$-methoxy-N-methyl-$3^5$-(trifluoromethyl)-6,13-dioxa-2,4-diaza-3(2,4)-pyrimidina-1(1,3),5(1,4)-dibenzenacyclotridecaphan-10- ene-$5^2$-carboxamide (yellow solid, 12 mg, 21%), LC-MS (ESI) calcd. for $C_{26}H_{27}F_3N_5O_4[M+H]^+$: 530.20. found: 530.70 (ret. time 2.3 min). $^1$H NMR (400 MHz, DMSO-$d_6$) δ 10.77 (s, 1H), 9.71 (s, 1H), 8.72 (q, J=4.6 Hz, 1H), 8.32 (s, 1H), 7.87 (d, J=9.1 Hz, 1H), 7.74 (d, J=2.6 Hz, 1H), 7.16 (d, J=2.8 Hz, 1H), 6.87 (d, J=8.7 Hz, 1H), 6.84 (dd, J=9.0, 2.9 Hz, 1H), 6.76 (dd, J=8.7, 2.7 Hz, 1H), 5.72 (dt, J=15.1, 7.4 Hz, 1H), 5.35 (dt, J=15.5, 5.4 Hz, 1H), 4.11 (t, J=4.8 Hz, 2H), 3.98 (dd, J=5.1, 1.7 Hz, 2H), 3.70 (s, 3H), 2.75 (d, J=4.5 Hz, 3H), 2.19 (q, J=6.5 Hz, 2H), 1.83 (dq, J=9.6, 5.1 Hz, 2H); and (Z)-$1^4$-methoxy-N-methyl-$3^5$-(trifluoromethyl)-6,13-dioxa-2,4-diaza-3(2,4)-pyrimidina-1(1,3),5(1,4)-dibenzenacyclotridecaphan-10-ene-$5^2$-carboxamide (yellow solid, 3 mg, 5%), LC-MS (ESI) calcd. for $C_{26}H_{27}F_3N_5O_4[M+H]^+$: 530.20. found: 530.65 (ret. time 2.2 min). $^1$H NMR (400 MHz, DMSO-$d_6$) δ 10.77 (s, 1H), 9.69 (s, 1H), 8.72 (q, J=4.9 Hz, 1H), 8.36 (s, 1H), 7.89 (d, J=8.8 Hz, 1H), 7.49 (d, J=2.4 Hz, 1H), 7.29 (d, J=2.8 Hz, 1H), 6.97 (dd, J=9.1, 2.7 Hz, 1H), 6.89 (d, J=8.8 Hz, 1H), 6.76 (dd, J=8.7, 2.6 Hz, 1H), 5.61 (q, J=7.4, 6.7 Hz, 2H), 4.14 (t, J=5.1 Hz, 2H), 3.99 (d, J=5.7 Hz, 2H), 3.71 (s, 3H), 2.77 (d, J=4.5 Hz, 3H), 2.20 (d, J=7.1 Hz, 2H), 1.75 (d, J=6.4 Hz, 2H).; and a mixture of isomers (E/Z)-$1^4$-methoxy-N-methyl-$3^5$-(trifluoromethyl)-6,13-dioxa-2,4-diaza-3(2,4)-pyrimidina-1(1,3),5(1,4)-dibenzenacyclotridecaphan-10-ene-$5^2$-carboxamide (yellow solid, 42 mg, 72%).

Example 12 Synthesis of Compound 20

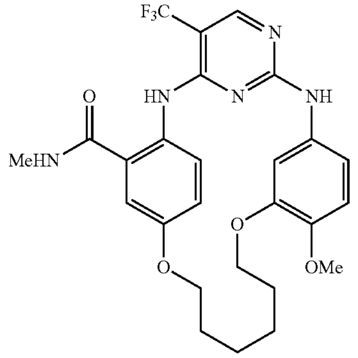 [SMILES: CNC(=O)c1cc2ccc1Nc1nc(ncc1C(F)(F)F)Nc1ccc(OC)c(c1)OCCCCCCO2]

$1^4$-Methoxy-N-methyl-$3^5$-(trifluoromethyl)-6,13-dioxa-2,4-diaza-3(2,4)-pyrimidina-1(1,3),5 (1,4)-dibenzenacyclotridecaphane-52-carboxamide (Compound 20). The title compound was prepared by reaction of (E/Z)-$1^4$-methoxy-N-methyl-$3^5$-(trifluoromethyl)-6,13-dioxa-2,4-diaza-3(2,4)-pyrimidina-1(1,3),5(1,4)-dibenzenacyclotridecaphan-10-ene-$5^2$-carboxamide (42 mg, 79 μmol) with catalytic Pd/C (4 mg, 40 μmol) in methanol (10 mL) for 6 hours according to Method 6 to provide the title compound as a white solid (22 mg, 52%). LC-MS (ESI) calcd. for $C_{26}H_{29}F_3N_5O_4$ $[M+H]^+$: 532.22. found: 532.20 (ret. time 2.3 min). $^1$H NMR (400 MHz, DMSO-$d_6$) δ 11.19 (s, 1H), 9.71 (s, 1H), 8.77 (q, J=4.5 Hz, 1H), 8.36 (s, 1H), 8.09 (d, J=9.1 Hz, 1H), 7.49 (d, J=2.4 Hz, 1H), 7.35 (d, J=2.8 Hz, 1H), 6.88 (d, J=8.7 Hz, 1H), 6.84 (dd, J=9.1, 2.8 Hz, 1H), 6.70 (dd, J=8.6, 2.4 Hz, 1H), 4.28 (t, J=5.2 Hz, 2H), 3.73 (s, 3H), 3.36 (t, J=5.7 Hz, 2H), 2.80 (d, J=4.4 Hz, 3H), 1.69-1.61 (m, 2H), 1.60-1.51 (m, 2H), 1.50-1.37 (m, 4H).

Example 13 Synthesis of Compound 9

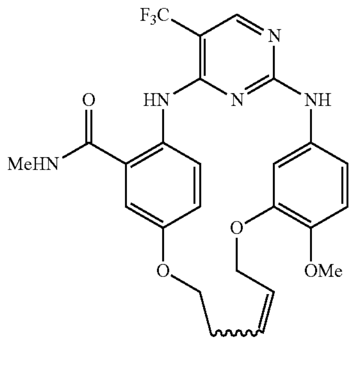 [SMILES: CNC(=O)c1cc2ccc1Nc1nc(ncc1C(F)(F)F)Nc1ccc(OC)c(c1)OCC=CCCO2]

(E/Z)-$1^4$-Methoxy-N-methyl-$3^5$-(trifluoromethyl)-6,12-dioxa-2,4-diaza-3(2,4)-pyrimidina-1(1,3),5(1,4)-dibenzenacyclododecaphan-9-ene-$5^2$-carboxamide (Compound 9). The title compound was prepared by reaction of 2-((2-((3-(allyloxy)-4-methoxyphenyl)amino)-5-(trifluoromethyl)pyrimidin-4-yl)amino)-5-(but-3-en-1-yloxy)-N-methylbenzamide (102 mg, 188 mol) with catalytic Grubs I catalyst (15 mg, 19 μmol) in dichloromethane (375 mL) according to Method 5 to provide: (E)-$1^4$-methoxy-N-methyl-$3^5$-(trifluoromethyl)-6,12-dioxa-2,4-diaza-3(2,4)-pyrimidina-1(1,3),5 (1,4)-dibenzenacyclododecaphan-9-ene-$5^2$-carboxamide (white solid, 32 mg, 33%), LC-MS (ESI) calcd. for $C_{25}H_{25}F_3N_5O_4[M+H]^+$: 516.19. found: 516.70 (ret. time 2.2 min) $^1$H NMR (400 MHz, DMSO-$d_6$) δ 10.71 (s, 1H), 9.79 (s, 1H), 8.74 (q, J=4.7 Hz, 1H), 8.36 (s, 1H), 7.94 (d, J=2.6 Hz, 1H), 7.89 (d, J=8.8 Hz, 1H), 7.26 (d, J=2.8 Hz, 1H), 7.09 (dd, J=9.0, 2.9 Hz, 1H), 6.99-6.87 (m, 2H), 5.74 (dt, J=15.2, 7.4 Hz, 1H), 5.53 (dt, J=15.5, 5.2 Hz, 1H), 4.37 (t, J=5.2 Hz, 2H), 4.28 (d, J=5.0 Hz, 2H), 3.74 (s, 3H), 2.77 (d, J=4.4 Hz, 3H), 2.49-2.40 (m, 2H); and (E/Z)-$1^4$-methoxy-N-methyl-$3^5$-(trifluoromethyl)-6,12-dioxa-2,4-diaza-3(2,4)-pyrimidina-1(1,3),5(1,4)-dibenzenacyclododecaphan-9-ene-$5^2$-carboxamide (white solid, 47 mg, 48%).

Example 14 Synthesis of Compound 10

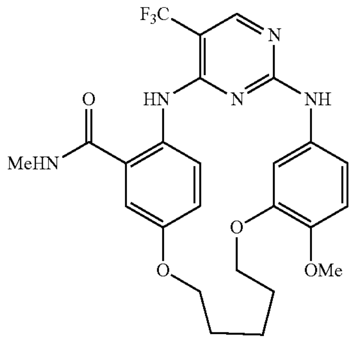 [SMILES: CNC(=O)c1cc2ccc1Nc1nc(ncc1C(F)(F)F)Nc1ccc(OC)c(c1)OCCCCCO2]

$1^4$-Methoxy-N-methyl-$3^5$-(trifluoromethyl)-6,12-dioxa-2,4-diaza-3(2,4)-pyrimidina-1(1,3), 5(1,4)-dibenzenacyclododecaphane-$5^2$-carboxamide (Compound 10). The title compound was prepared by reaction of (E/Z)-$1^4$-methoxy-N-methyl-$3^5$-(trifluoromethyl)-6,12-dioxa-2,4-diaza-3(2,4)-pyrimidina-1(1,3),5(1,4)-dibenzenacyclododecaphan-9-ene-$5^2$-carboxamide (30 mg, 58 μmol) with catalytic Pd/C (5 mg, 45 μmol) in methanol (10 mL) according to Method 6 to provide the title compound as a white solid (10 mg, 33%). LC-MS (ESI) calcd. for $C_{25}H_{27}F_3N_5O_4[M+H]^+$: 518.20. found: 518.15 (ret. time 2.1 min). $^1H$ NMR (400 MHz, DMSO-$d_6$) δ 10.76 (s, 1H), 9.65 (s, 1H), 8.73 (d, J=4.7 Hz, 1H), 8.35 (s, 1H), 7.83 (d, J=8.8 Hz, 1H), 7.36 (dd, J=5.2, 2.7 Hz, 2H), 6.91 (d, J=9.0 Hz, 1H), 6.89 (d, J=8.5 Hz, 1H), 6.74 (dd, J=8.7, 2.4 Hz, 1H), 4.28 (t, J=5.2 Hz, 2H), 3.74 (s, 3H), 3.38 (t, J=5.0 Hz, 2H), 2.78 (d, J=4.5 Hz, 3H), 1.66-1.56 (m, 6H).

Example 15 Synthesis of Compound 24

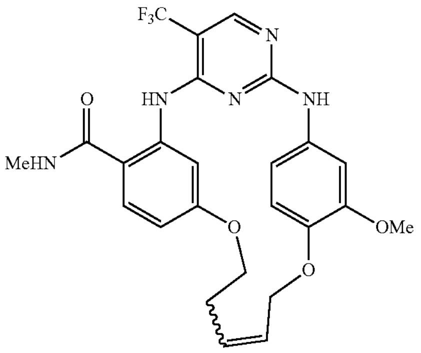 [SMILES: CNC(=O)c1ccc2cc1Nc1nc(ncc1C(F)(F)F)Nc1ccc(c(OC)c1)OCC=CCCO2]

(E/Z)-$5^3$-Methoxy-N-methyl-$3^5$-(trifluoromethyl)-6,12-dioxa-2,4-diaza-3(4,2)-pyrimidina-1(1,3),5(1,4)-dibenzenacyclododecaphan-8-ene-$1^6$-carboxamide (Compound 24). The title compound was prepared by reaction of 2-((2-((4-(allyloxy)-3-methoxyphenyl)amino)-5-(trifluoromethyl) pyrimidin-4-yl)amino)-4-(but-3-en-1-yloxy)-N-methylbenzamide (40 mg, 74 μmol) with catalytic Grubs I catalyst (6 mg, 7.4 μmol) in dichloromethane (147 mL) according to Method 5 to provide: (E)-$5^3$-methoxy-N-methyl-$3^5$-(trifluoromethyl)-6,12-dioxa-2,4-diaza-3(4,2)-pyrimidina-1(1,3),5 (1,4)-dibenzenacyclododecaphan-8-ene-$1^6$-carboxamide (white solid, 33 mg, 87%), LC-MS (ESI) calcd. for $C_{25}H_{25}F_3N_5O_4[M+H]^+$: 516.19. found: 516.15 (ret. time 2.1 min). $^1H$ NMR (400 MHz, DMSO-$d_6$) δ 12.02 (s, 1H), 9.68 (s, 1H), 8.57 (d, J=4.7 Hz, 1H), 8.36 (s, 1H), 8.09 (d, J=2.6 Hz, 1H), 7.70 (d, J=8.8 Hz, 1H), 7.30 (dd, J=8.7, 2.4 Hz, 1H), 6.93 (d, J=2.5 Hz, 1H), 6.79 (d, J=8.7 Hz, 1H), 6.73 (dd, J=8.8, 2.6 Hz, 1H), 5.78 (dt, J=14.1, 6.3 Hz, 1H), 5.43 (td, J=15.1, 6.1 Hz, 1H), 4.63 (d, J=5.6 Hz, 2H), 4.07 (q, J=5.3 Hz, 1H), 4.01 (t, J=5.3 Hz, 2H), 3.59 (s, 2H), 3.13 (d, J=5.2 Hz, 2H), 2.73 (d, J=4.4 Hz, 3H); and (Z)-$5^3$-methoxy-N-methyl-$3^5$-(trifluoromethyl)-6,12-dioxa-2,4-diaza-3(4,2)-pyrimidina-1(1,3),5(1,4)-dibenzenacyclododecaphan-8-ene-$1^6$-carboxamide (white solid, 1 mg, 2%).

Example 16 Synthesis of Compound 25

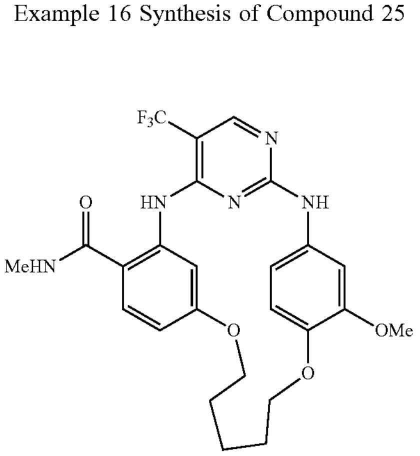

$5^3$-Methoxy-N-methyl-$3^5$-(trifluoromethyl)-6,12-dioxa-2,4-diaza-3(4,2)-pyrimidina-1(1,3), 5(1,4)-dibenzenacyclododecaphane-$1^6$-carboxamide (Compound 25). The title compound was prepared by reaction of (E/Z)-$5^3$-methoxy-N-methyl-$3^5$-(trifluoromethyl)-6,12-dioxa-2,4-diaza-3(4,2)-pyrimidina-1(1,3),5(1,4)-dibenzenacyclododecaphan-8-ene-$1^6$-carboxamide (21 mg, 41 μmol) with catalytic Pd/C (3 mg, 20 μmol) in methanol (5 mL) according to Method 6 to provide the title compound as a white solid (10 mg, 47%). LC-MS (ESI) calcd. for $C_{25}H_{27}F_3N_5O_4[M+H]^+$: 518.20. found: 518.65 (ret. time 2.1 min). $^1H$ NMR (400 MHz, DMSO-$d_6$) δ 12.08 (s, 1H), 9.68 (s, 1H), 8.57 (q, J=4.9 Hz, 1H), 8.39 (s, 1H), 8.15 (d, J=2.4 Hz, 1H), 7.69 (d, J=8.8 Hz, 1H), 7.02 (d, J=1.9 Hz, 1H), 7.01-6.92 (m, 2H), 6.66 (dd, J=8.8, 2.6 Hz, 1H), 4.20 (t, J=5.2 Hz, 2H), 3.77 (t, J=5.0 Hz, 2H), 3.54 (s, 3H), 2.76 (d, J=4.4 Hz, 3H), 1.70-1.59 (m, 4H), 1.56-1.48 (m, 2H).

Example 17 Synthesis of Compounds 12 and 13

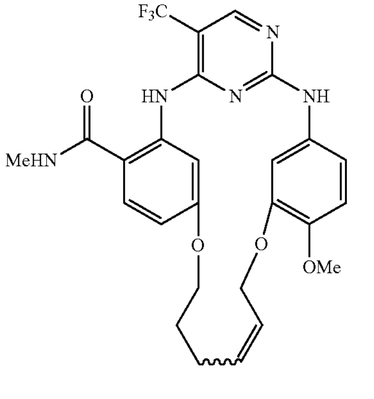 [SMILES: CNC(=O)c1ccc2cc1Nc1nc(ncc1C(F)(F)F)Nc1ccc(OC)c(c1)OCC=CCCCO2]

(E/Z)-$1^4$-Methoxy-N-methyl-$3^5$-(trifluoromethyl)-6,13-dioxa-2,4-diaza-3(2,4)-pyrimidina-1,5(1,3)-dibenzenacyclotridecaphan-10-ene-$5^6$-carboxamide (Compounds 12 and 13). The title compound was prepared by reaction of 2-((2-((3-(allyloxy)-4-methoxyphenyl)amino)-5-(trifluoromethyl) pyrimidin-4-yl)amino)-N-methyl-4-(pent-4-en-1-yloxy) benzamide (100 mg, 179 μmol) with catalytic Grubs I catalyst (15 mg, 18 μmol) in dichloromethane (359 mL) for 40 hours according to Method 5 to provide: (E)-$1^4$-methoxy-N-methyl-35-(trifluoromethyl)-6,13-dioxa-2,4-diaza-3(2, 4)-pyrimidina-1,5(1,3)-dibenzenacyclotridecaphan-10-ene- $5^6$-carboxamide (white solid, 7 mg, 7%), LC-MS (ESI) calcd. for $C_{26}H_{27}F_3N_5O_4[M+H]^+$: 530.20. found: 530.25 (ret. time 2.2 min). $^1H$ NMR (400 MHz, DMSO-$d_6$) δ 11.74 (s, 1H), 9.55 (s, 1H), 8.53 (q, J=4.6 Hz, 1H), 8.39 (s, 1H), 7.88 (d, J=2.4 Hz, 1H), 7.64 (d, J=8.8 Hz, 1H), 7.20 (d, J=2.4 Hz, 1H), 6.85 (d, J=8.5 Hz, 1H), 6.73 (d, J=8.6 Hz, 1H), 6.67 (dd, J=8.8, 2.6 Hz, 1H), 5.86-5.76 (m, 1H), 5.65 (dt, J=11.1, 8.1 Hz, 1H), 4.50 (d, J=6.9 Hz, 2H), 3.90 (t, J=5.8 Hz, 2H), 3.71 (s, 3H), 2.73 (d, J=4.5 Hz, 3H), 2.17 (q, J=7.0, 6.4 Hz, 2H), 1.72 (p, J=5.8 Hz, 2H); and (Z)-$1^4$-methoxy-N-methyl-35-(trifluoromethyl)-6,13-dioxa-2,4-diaza-3(2,4)-pyrimidina-1,5(1,3)-dibenzenacyclotridecaphan-10-ene-$5^6$-carboxamide (white solid, 6 mg, 6%), LC-MS (ESI) calcd. for $C_{26}H_{27}F_3N_5O_4[M+H]^+$: 530.20. found: 530.60 (ret. time 2.3 min). $^1H$ NMR (400 MHz, DMSO-$d_6$) δ 11.89 (s, 1H), 9.63 (s, 1H), 8.55 (q, J=4.3 Hz, 1H), 8.42 (s, 1H), 7.78 (d, J=2.6 Hz, 1H), 7.60 (d, J=8.8 Hz, 1H), 7.22 (dd, J=8.8, 2.5 Hz, 1H), 6.85 (d, J=2.5 Hz, 1H), 6.68 (d, J=8.8 Hz, 1H), 6.58 (dd, J=8.7, 2.6 Hz, 1H), 5.58-5.39 (m, 2H), 4.59 (d, J=5.8 Hz, 2H), 3.71 (s, 3H), 3.21-3.18 (m, 2H), 2.76 (d, J=4.5 Hz, 3H), 2.03-1.99 (m, 2H), 1.69-1.65 (m, 2H); and a mixture of (E/Z)-$1^4$-methoxy-N-methyl-35-(trifluoromethyl)-6,13-dioxa-2,4-diaza-3(2,4)-pyrimidina-1,5(1,3)-dibenzenacyclotridecaphan-10-ene-$5^6$-carboxamide (white solid, 62 mg, 65%).

Example 18 Synthesis of Compound 14

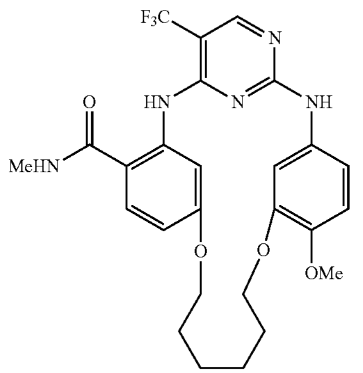 [SMILES: CNC(=O)c1ccc2cc1Nc1nc(ncc1C(F)(F)F)Nc1ccc(OC)c(c1)OCCCCCCO2]

$1^4$-Methoxy-N-methyl-$3^5$-(trifluoromethyl)-6,13-dioxa-2,4-diaza-3(2,4)-pyrimidina-1,5(1,3)-dibenzenacyclotridecaphane-$5^6$-carboxamide (Compound 14). The title compound was prepared by reaction of (E/Z)-$1^4$-methoxy-N-methyl-35-(trifluoromethyl)-6,13-dioxa-2,4-diaza-3(2,4)-pyrimidina-1,5(1,3)-dibenzenacyclotridecaphan-10-ene-$5^6$-carboxamide (62 mg, 117 μmol) with catalytic Pd/C (6 mg, 58 μmol) in methanol (10 mL) according to Method 6 to provide the title compound as a white solid (48 mg, 77%). LC-MS (ESI) calcd. for $C_{26}H_{29}F_3N_5O_4[M+H]^+$: 532.22. found: 532.70 (ret. time 2.3 min). $^1H$ NMR (400 MHz, DMSO-$d_6$) δ 12.00 (s, 1H), 9.53 (s, 1H), 8.53 (q, J=4.5 Hz, 1H), 8.38 (s, 1H), 7.97 (d, J=2.5 Hz, 1H), 7.64 (d, J=8.9 Hz, 1H), 7.06 (d, J=2.2 Hz, 1H), 6.89-6.78 (m, 2H), 6.62 (dd, J=8.7, 2.6 Hz, 1H), 4.04 (t, J=5.5 Hz, 2H), 3.83 (t, J=6.2 Hz, 2H), 3.74 (s, 3H), 2.75 (d, J=4.5 Hz, 3H), 1.70-1.56 (m, 4H), 1.50 (p, J=6.5 Hz, 2H), 1.26 (p, J=6.7 Hz, 2H).

Example 19 Synthesis of Compounds 21 and 22

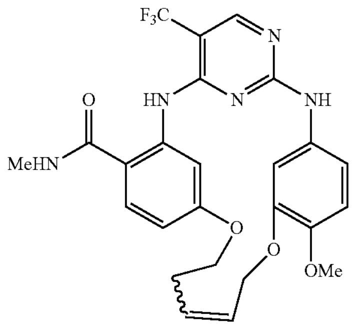 [SMILES: CNC(=O)c1ccc2cc1Nc1nc(ncc1C(F)(F)F)Nc1ccc(OC)c(c1)OCC=CCCO2]

(E/Z)-$1^4$-Methoxy-N-methyl-$3^5$-(trifluoromethyl)-6,12-dioxa-2,4-diaza-3(2,4)-pyrimidina-1,5(1,3)-dibenzenacyclododecaphan-9-ene-$5^6$-carboxamide (Compounds 21 and 22). The title compound was prepared by reaction of 2-((2-((3-(allyloxy)-4-methoxyphenyl)amino)-5-(trifluoromethyl)pyrimidin-4-yl)amino)-4-(but-3-en-1-yloxy)-N-methylbenzamide (98 mg, 181 μmol) with catalytic Grubs I catalyst (15 mg, 18 μmol) in dichloromethane (362 mL) according to Method 5 to provide: (E)-$1^4$-methoxy-N-methyl-$3^5$-(trifluoromethyl)-6,12-dioxa-2,4-diaza-3(2,4)-pyrimidina-1,5(1,3)-dibenzenacyclododecaphan-9-ene-$5^6$-carboxamide (white solid, 16 mg, 17%), LC-MS (ESI) calcd. for $C_{25}H_{25}F_3N_5O_4$ $[M+H]^+$: 516.19. found: 516.55 (ret. time 2.1 min). $^1H$ NMR (400 MHz, DMSO-$d_6$) δ 11.92 (s, 1H), 9.51 (s, 1H), 8.56 (d, J=4.8 Hz, 1H), 8.40 (s, 1H), 7.96 (d, J=2.4 Hz, 1H), 7.65 (d, J=8.7 Hz, 1H), 6.97-6.88 (m, 2H), 6.78 (d, J=8.7 Hz, 1H), 6.60 (dd, J=8.7, 2.6 Hz, 1H), 5.58 (dt, J=15.5, 6.7 Hz, 1H), 5.47 (dt, J=15.2, 6.3 Hz, 1H), 4.62 (d, J=6.4 Hz, 2H), 3.72 (s, 3H), 3.66 (t, J=6.0 Hz, 2H), 2.76 (d, J=4.5 Hz, 3H), 2.28 (q, J=6.1 Hz, 2H); and (Z)-$1^4$-methoxy-N-methyl-$3^5$-(trifluoromethyl)-6,12-dioxa-2,4-diaza-3(2,4)-pyrimidina-1,5(1,3)-dibenzenacyclododecaphan-9-ene-$5^6$-carboxamide (white solid, 10 mg, 11%), LC-MS (ESI) calcd. for $C_{25}H_{25}F_3N_5O_4[M+H]^+$: 516.19. found: 516.60 (ret. time 2.2 min). $^1H$ NMR (400 MHz, DMSO-$d_6$) δ 11.90 (s, 1H), 9.61 (s, 1H), 8.54 (d, J=5.2 Hz, 1H), 8.41 (s, 1H), 7.96 (d, J=2.6 Hz, 1H), 7.61 (d, J=8.8 Hz, 1H), 7.05 (dd, J=8.7, 2.7 Hz, 1H), 6.79 (d, J=9.1 Hz, 1H), 6.69 (d, J=2.7 Hz, 1H), 6.55 (dd, J=8.8, 2.6 Hz, 1H), 5.74 (dt, J=11.0, 7.6 Hz, 1H), 5.65 (dt, J=11.1, 7.8 Hz, 1H), 4.61 (d, J=7.7 Hz, 2H), 3.77 (s, 3H), 2.83 (t, J=7.8 Hz, 2H), 2.76 (d, J=4.4 Hz, 3H), 2.28 (q, J=7.8 Hz, 2H); and the mixture of (E/Z)-$1^4$-methoxy-N-methyl-$3^5$-(trifluoromethyl)-6,12-dioxa-2,4-diaza-3(2,4)-pyrimidina-1,5(1,3)-dibenzenacyclododecaphan-9-ene-$5^6$-carboxamide (white solid, 32 mg, 34%).

Example 20 Synthesis of Compound 23

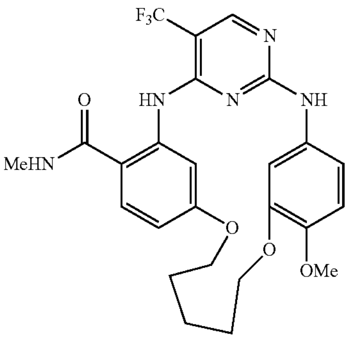 [SMILES: CNC(=O)c1ccc2cc1Nc1nc(ncc1C(F)(F)F)Nc1ccc(OC)c(c1)OCCCCCO2]

$1^4$-methoxy-N-methyl-$3^5$-(trifluoromethyl)-6,12-dioxa-2,4-diaza-3(2,4)-pyrimidina-1,5(1,3)-dibenzenacyclododecaphane-$5^6$-carboxamide (Compound 23). The title compound was prepared by reaction of (E/Z)-$1^4$-methoxy-N-methyl-$3^5$-(trifluoromethyl)-6,12-dioxa-2,4-diaza-3(2,4)-pyrimidina-1,5(1,3)-dibenzenacyclododecaphan-9-ene-$5^6$-carboxamide (31 mg, 60 μmol) with catalytic Pd/C (3 mg, 30 μmol) in methanol (5 mL) according to Method 6 to provide the title compound as a white solid (29 mg, 93%). LC-MS (ESI) calcd. for $C_{25}H_{27}F_3N_5O_4[M+H]^+$: 518.20. found: 518.25 (ret. time 2.1 min). $^1H$ NMR (400 MHz, DMSO-$d_6$) δ 11.75 (s, 1H), 9.50 (s, 1H), 8.52 (q, J=4.5 Hz, 1H), 8.38 (s, 1H), 7.81 (d, J=2.6 Hz, 1H), 7.63 (d, J=8.8 Hz, 1H), 7.14 (d, J=2.5 Hz, 1H), 6.85 (d, J=8.7 Hz, 1H), 6.69 (dd, J=8.7, 2.4 Hz, 1H), 6.62 (dd, J=8.9, 2.5 Hz, 1H), 4.12 (t, J=5.5 Hz, 2H), 3.80 (t, J=5.6 Hz, 2H), 3.72 (s, 3H), 2.74 (d, J=4.4 Hz, 3H), 1.83-1.73 (m, 2H), 1.73-1.66 (m, 2H), 1.65-1.58 (m, 2H).

Compounds for which synthesis protocols were not supplied were prepared using analogous methods to those provided above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound or a pharmaceutically acceptable salt, solvate, or stereoisomer thereof wherein the compound is selected from:

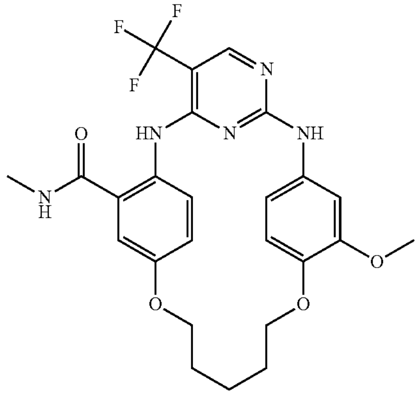
,

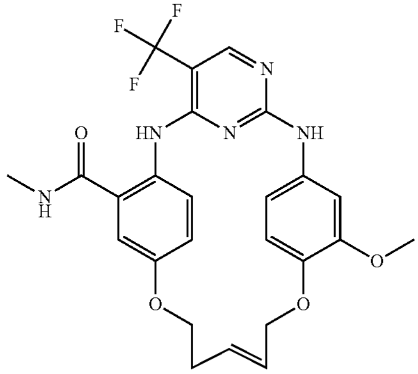
,

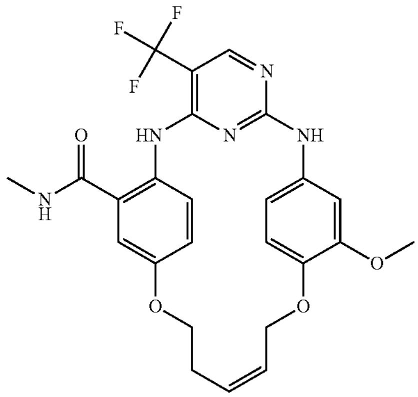
,

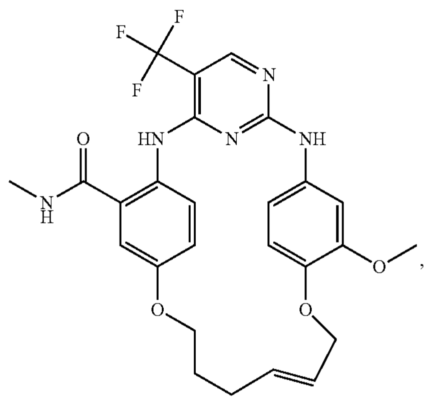
,

-continued
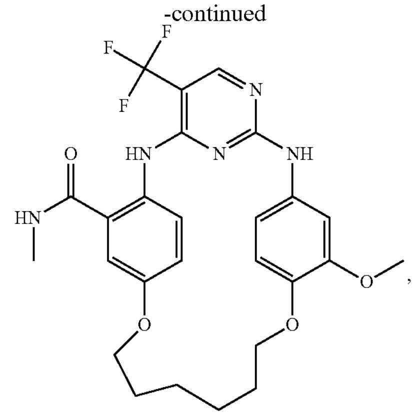
,
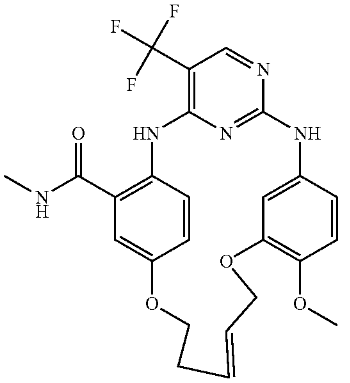
,
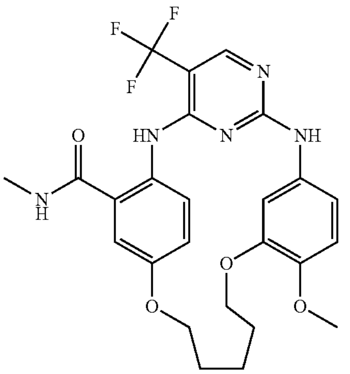
,
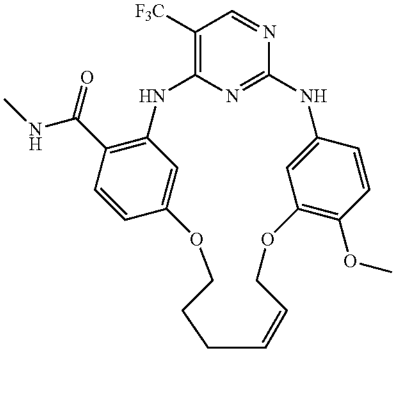
,
-continued
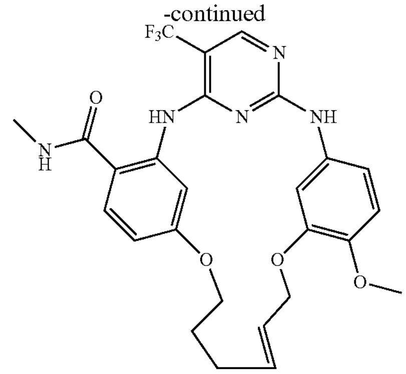
,
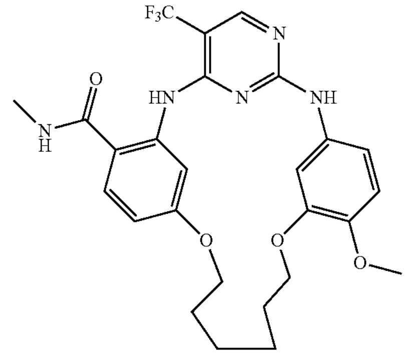
,
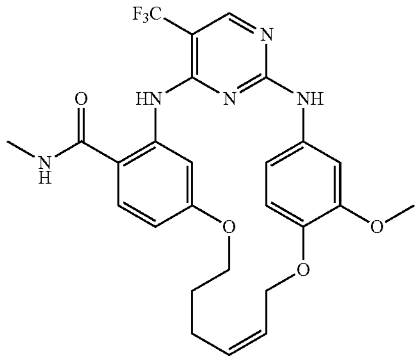
,
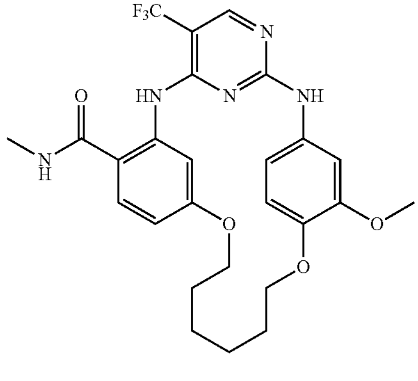
, -continued

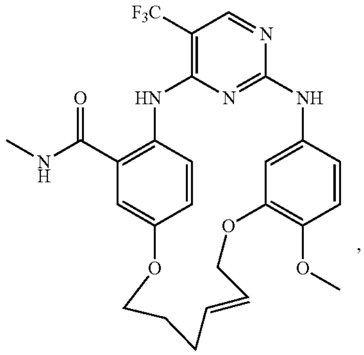

,

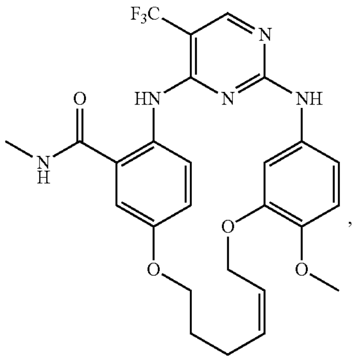

,

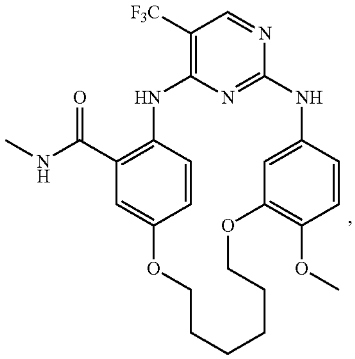

,

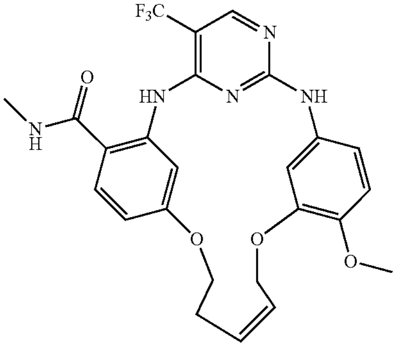

,

-continued

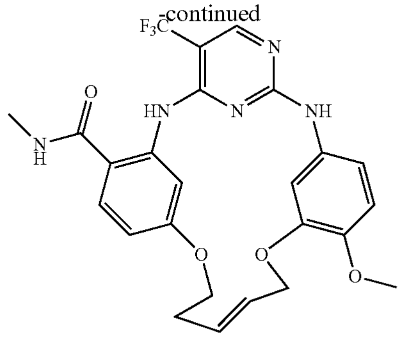

,

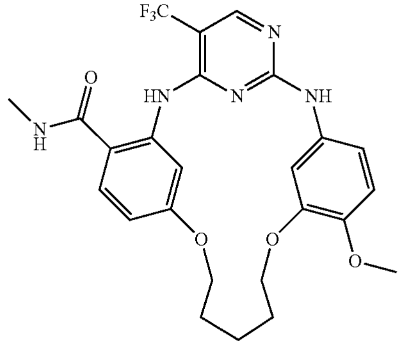

,

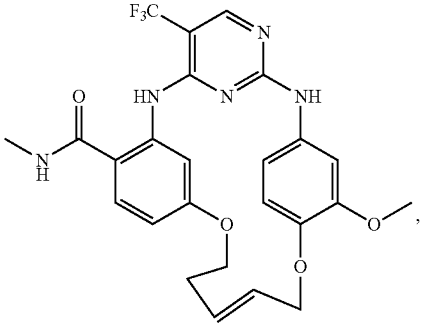

, and

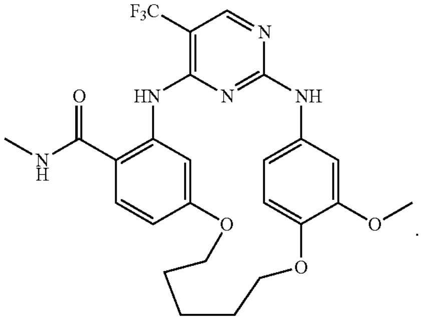

.

2. A pharmaceutical composition comprising the compound or pharmaceutically acceptable salt thereof of claim 1 and a pharmaceutically acceptable carrier.

3. A method of treating a ULK mediated disease in a subject in need thereof, the method comprising administering to the subject a compound according to claim 1, or a pharmaceutically acceptable salt thereof, or a pharmaceutical composition comprising the compound or pharmaceutically acceptable salt thereof of claim 1 and a pharmaceutically acceptable carrier.

4. The method of claim 3, wherein the ULK mediated disease is characterized by abnormal autophagy.

5. The method of claim 3, wherein the disease is cancer, tuberous sclerosis complex (TSC) or lymphangioleiomyomatosis (LAM).

6. The method of claim 5, wherein the cancer is lung cancer, breast cancer, or pancreatic cancer.

7. The method of claim 3, wherein the compound is co-administered with an additional therapeutic agent.

8. The method of claim 7, wherein the additional therapeutic agent is selected from the group consisting of: an mTOR inhibitor, carboplatin, an MEK inhibitor, and a PARP inhibitor.

* * * * *